United States Patent
Fellman et al.

(10) Patent No.: US 12,226,344 B2
(45) Date of Patent: Feb. 18, 2025

(54) SURGICAL INSTRUMENTS FOR ANTERIOR GONIOTOMY

(71) Applicants: RAICO International LLC, Westmont, IL (US); Innovative Glaucoma Consulting LLC, Dallas, TX (US); EyeInnovate LLC, Dallas, TX (US)

(72) Inventors: Ronald L. Fellman, Dallas, TX (US); Davinder S. Grover, Dallas, TX (US); Sebastian S. Grover, Dallas, TX (US); Ravi Nallakrishnan, Willowbrook, IL (US)

(73) Assignees: RAICO International LLC, Westmont, IL (US); Innovative Glaucoma Consulting LLC, Dallas, TX (US); EyeInnovate LLC, Dallas, TX (US)

( * ) Notice: Subject to any disclaimer, the term of this patent is extended or adjusted under 35 U.S.C. 154(b) by 0 days.

(21) Appl. No.: 18/780,833

(22) Filed: Jul. 23, 2024

(65) Prior Publication Data
US 2024/0407949 A1 Dec. 12, 2024

Related U.S. Application Data

(63) Continuation of application No. 18/637,133, filed on Apr. 16, 2024, now Pat. No. 12,102,563, which is a continuation of application No. PCT/US2023/018590, filed on Apr. 14, 2023.

(60) Provisional application No. 63/341,485, filed on May 13, 2022.

(51) Int. Cl.
| | |
|---|---|
| A61F 9/007 | (2006.01) |
| A61B 17/00 | (2006.01) |
| A61B 17/3211 | (2006.01) |

(52) U.S. Cl.
CPC .............. *A61F 9/00781* (2013.01); *A61B 2017/00738* (2013.01); *A61B 17/3211* (2013.01); *A61B 2217/007* (2013.01)

(58) Field of Classification Search
CPC .............. A61F 9/00736; A61F 9/00754; A61F 9/00781; A61B 17/3211; A61B 2017/00738; A61B 2217/007
See application file for complete search history.

(56) References Cited

U.S. PATENT DOCUMENTS

| | | |
|---|---|---|
| 10,123,905 B2 | 11/2018 | Mittelstein |
| 10,327,947 B2 | 6/2019 | Kahook |
| 10,639,195 B1 | 5/2020 | Mackool |
| 10,682,254 B2 | 6/2020 | Kahook |

(Continued)

FOREIGN PATENT DOCUMENTS

| | | |
|---|---|---|
| WO | 2021242861 A1 | 12/2021 |
| WO | 2022086754 A1 | 4/2022 |

*Primary Examiner* — Ryan J. Severson
(74) *Attorney, Agent, or Firm* — Wood, Phillips, Katz, Clark & Mortimer

(57) ABSTRACT

A surgical instrument (40, 40A) for performing a goniotomy procedure includes a hand grip (44, 44A) having an elongated configuration with proximal and distal ends. The instrument (40, 40A) includes a tip (52, 52A) connected to the distal end (48, 48A) of the hand grip (44, 44A) which has a cutting means for creating a trabecular cleavage plane resulting in a remaining trabecular leaflet directly below Schwalbe's line in an eye to enhance drainage of aqueous humor from the eye. In one form, the cutting means includes a pair of sloping, arcuate cutting surfaces (70, 70A) that join to define an arcuate cutting edge (74, 74A).

11 Claims, 31 Drawing Sheets

(56) References Cited

U.S. PATENT DOCUMENTS

| | | |
|---|---|---|
| 10,779,991 B2 | 9/2020 | Kahook |
| 11,266,527 B2 | 3/2022 | Baerveldt |
| 2015/0045820 A1 | 2/2015 | Kahook |
| 2016/0106589 A1 | 4/2016 | Mittelstein |
| 2017/0181892 A1 | 6/2017 | Kahook |
| 2018/0133056 A1 | 5/2018 | Kahook |
| 2018/0289544 A1 | 10/2018 | Baerveldt |
| 2020/0107961 A1 | 4/2020 | Kahook |
| 2021/0000648 A1 | 1/2021 | Nallakrishnan |
| 2021/0212859 A1 | 7/2021 | Koontz |
| 2021/0322216 A1 | 10/2021 | Akahoshi |
| 2022/0087864 A1 | 3/2022 | Yokoyama |
| 2023/0000682 A1 | 1/2023 | Nallakrishnan |
| 2023/0190527 A1 | 6/2023 | Espaillat |
| 2023/0363943 A1 | 11/2023 | Tanito |

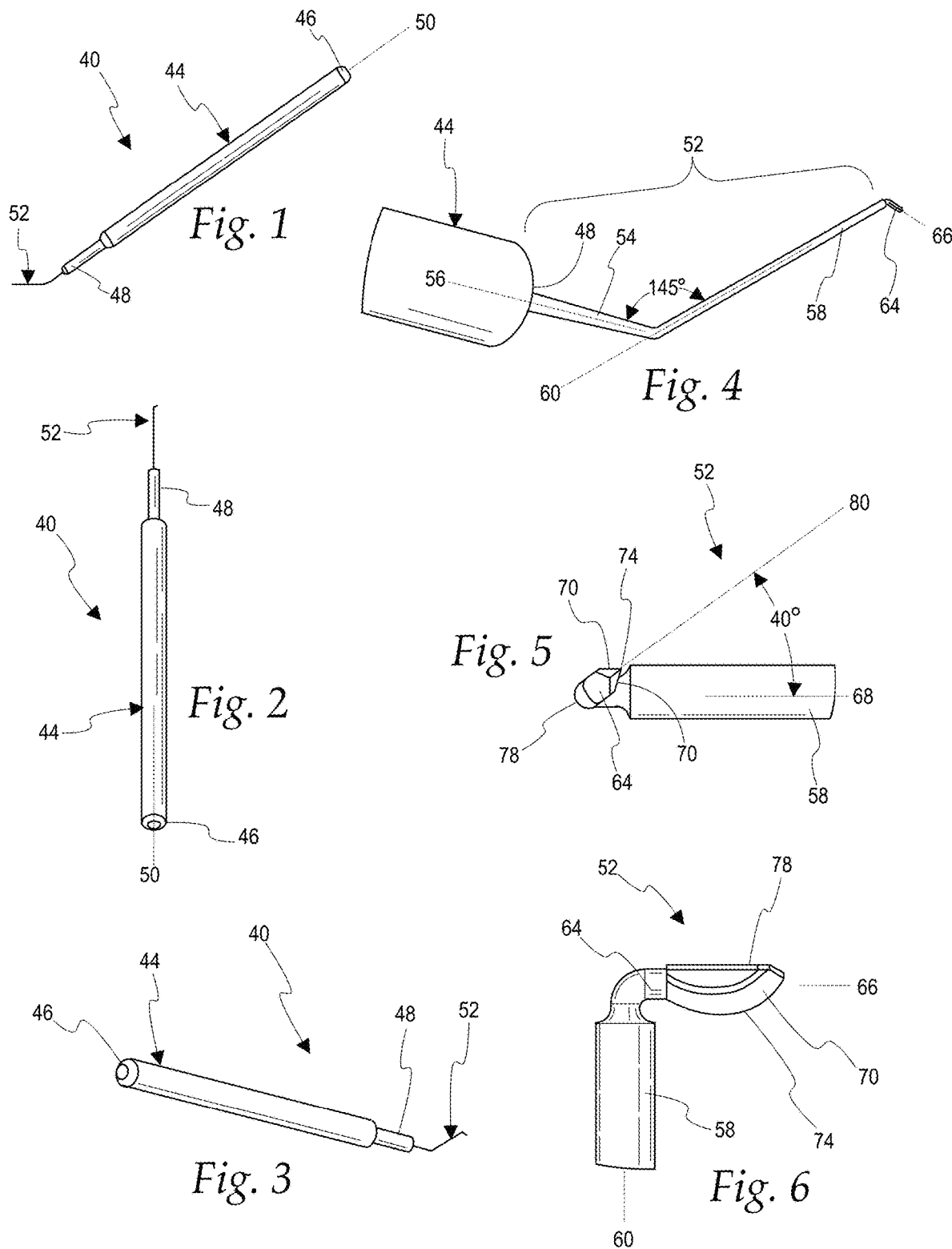

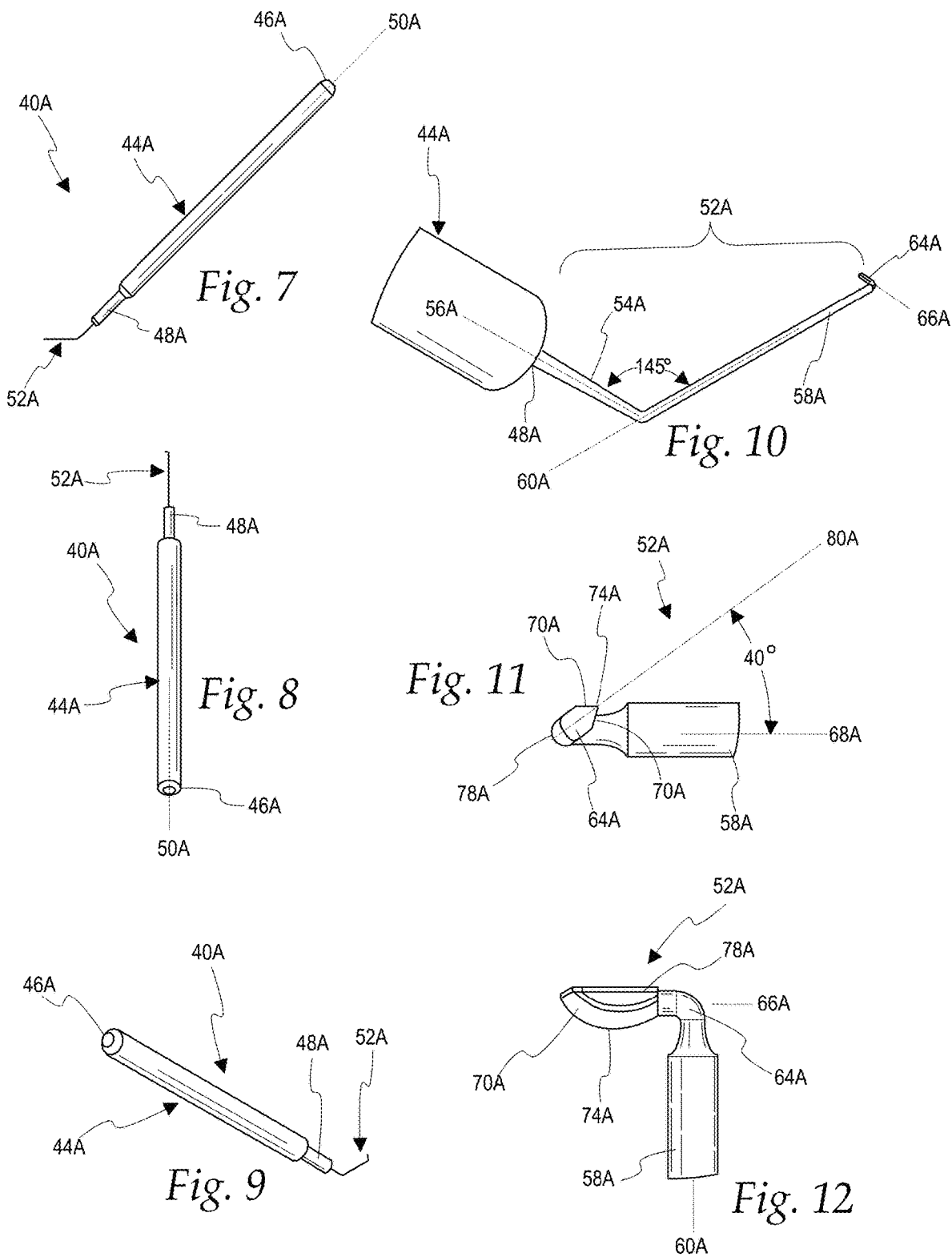

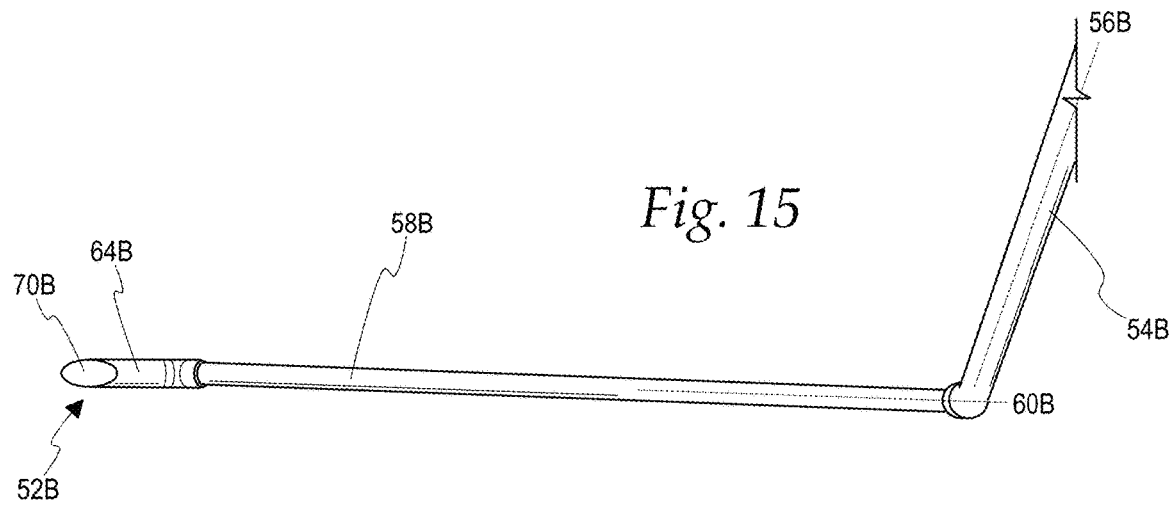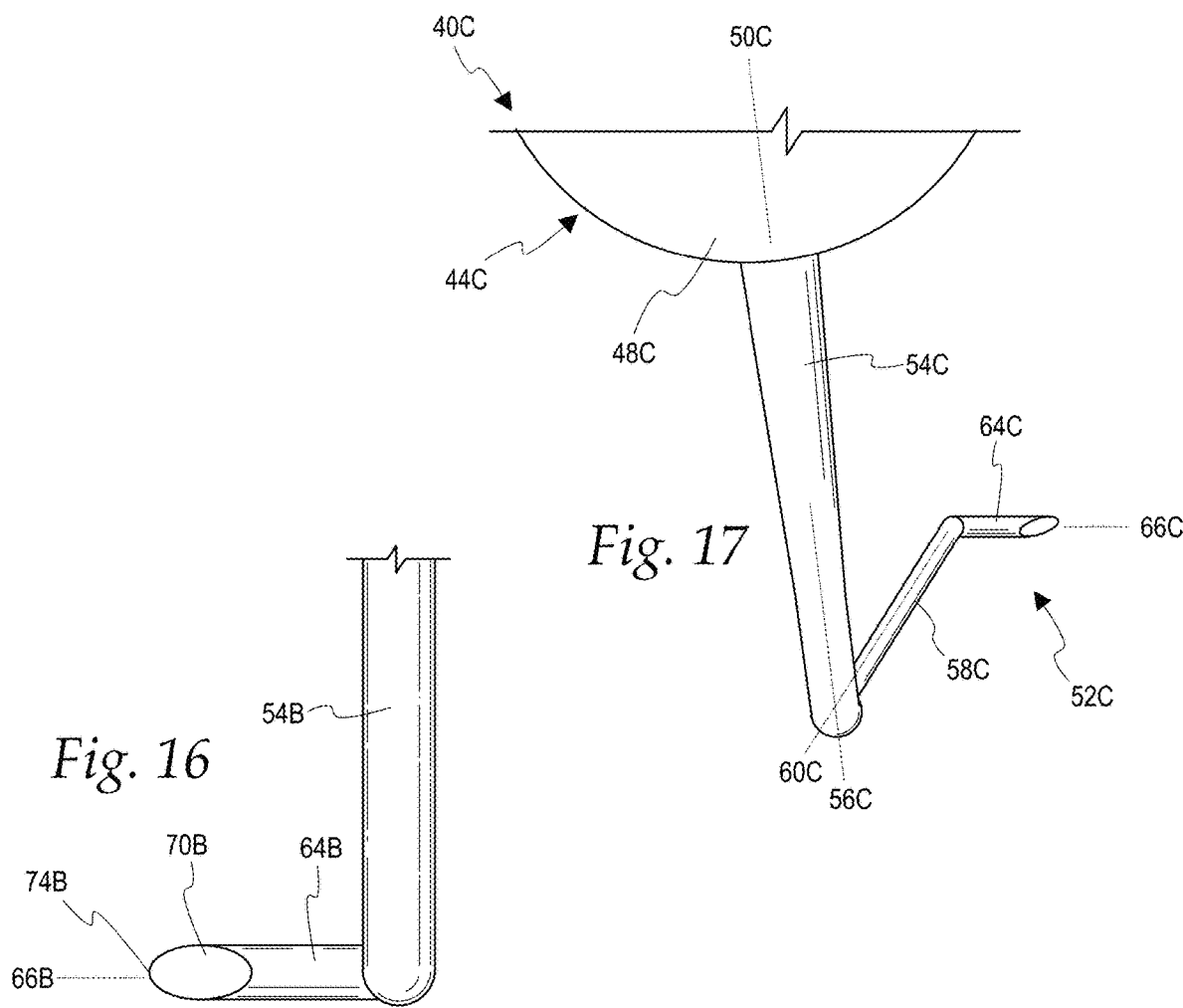

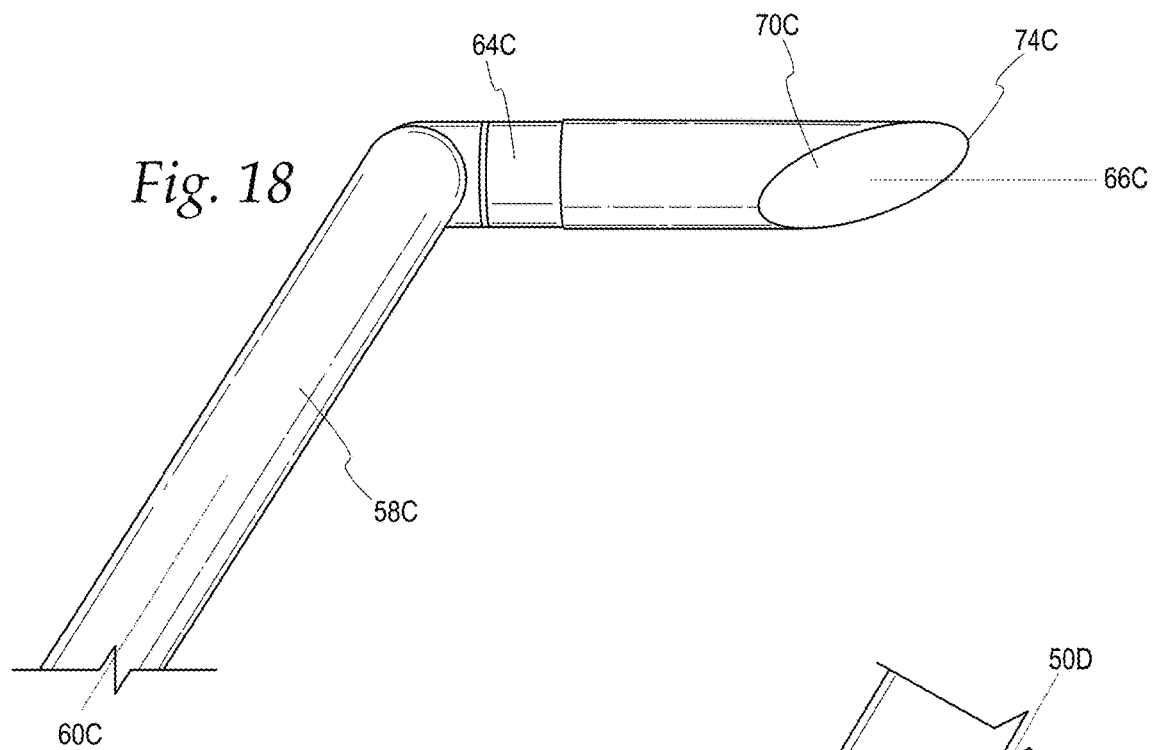
Fig. 18
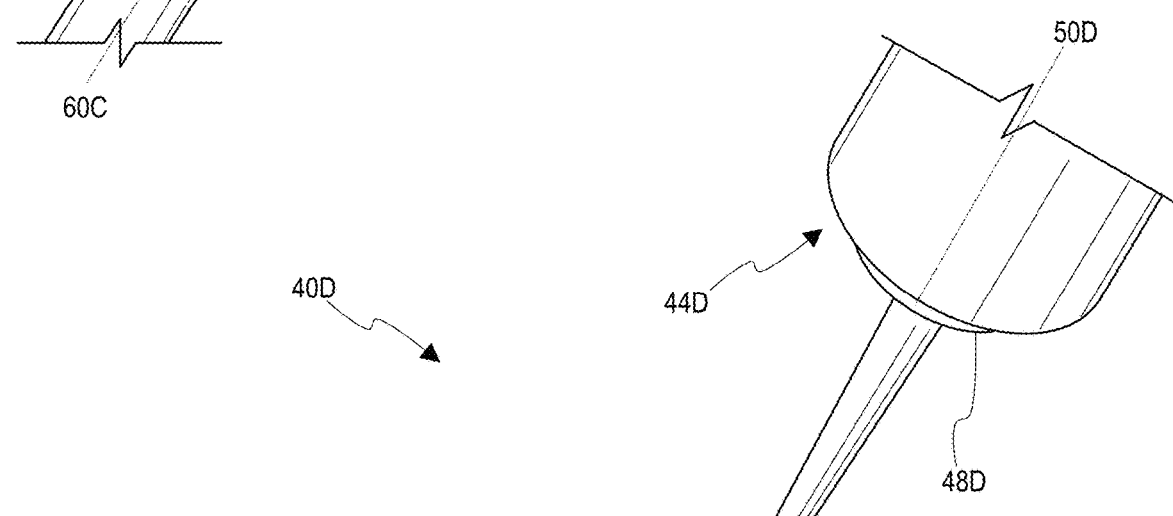
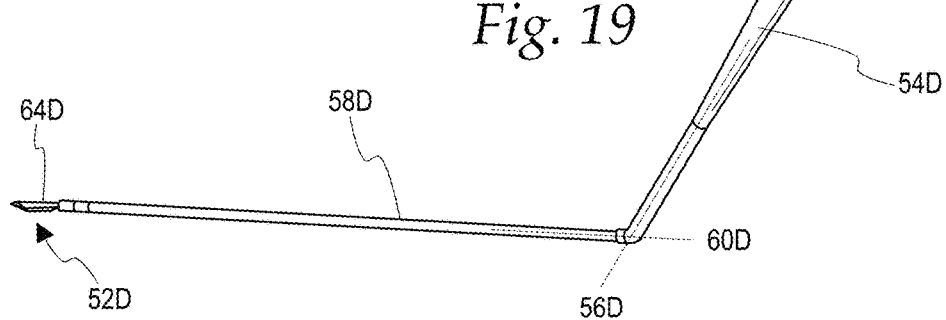
Fig. 19

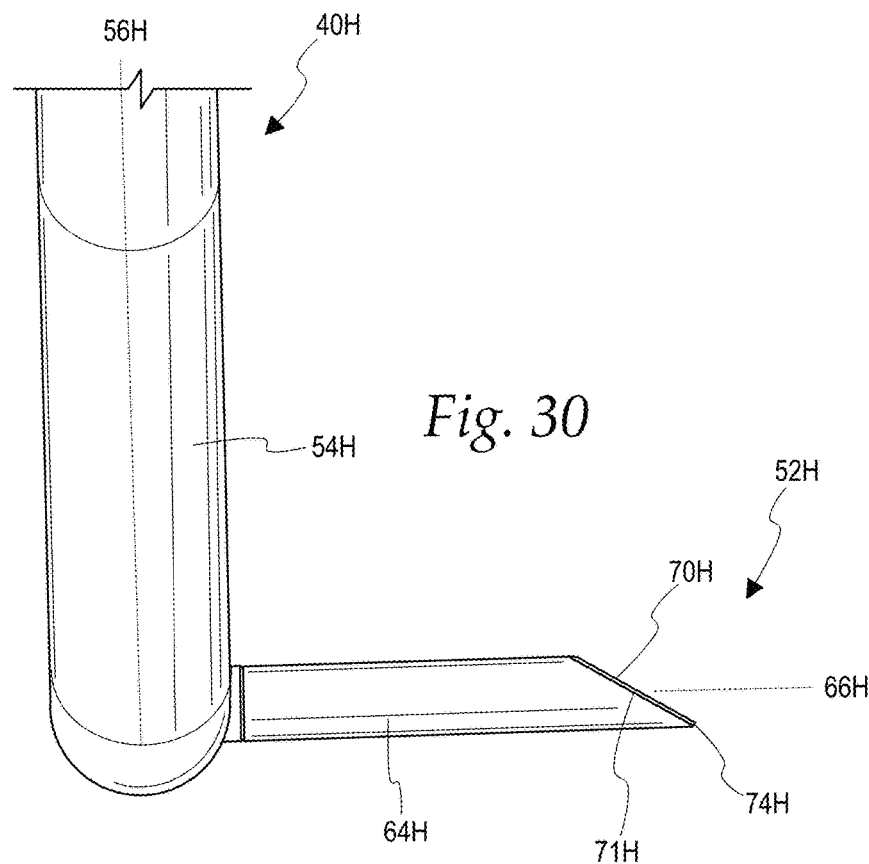
Fig. 30
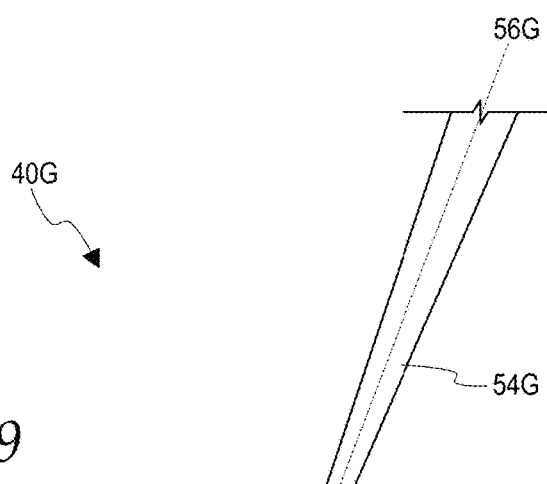
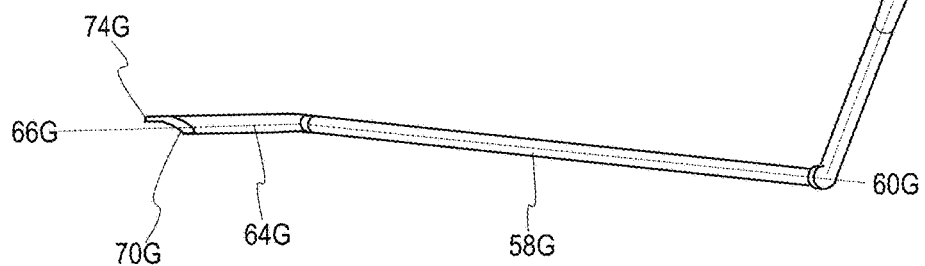
Fig. 29

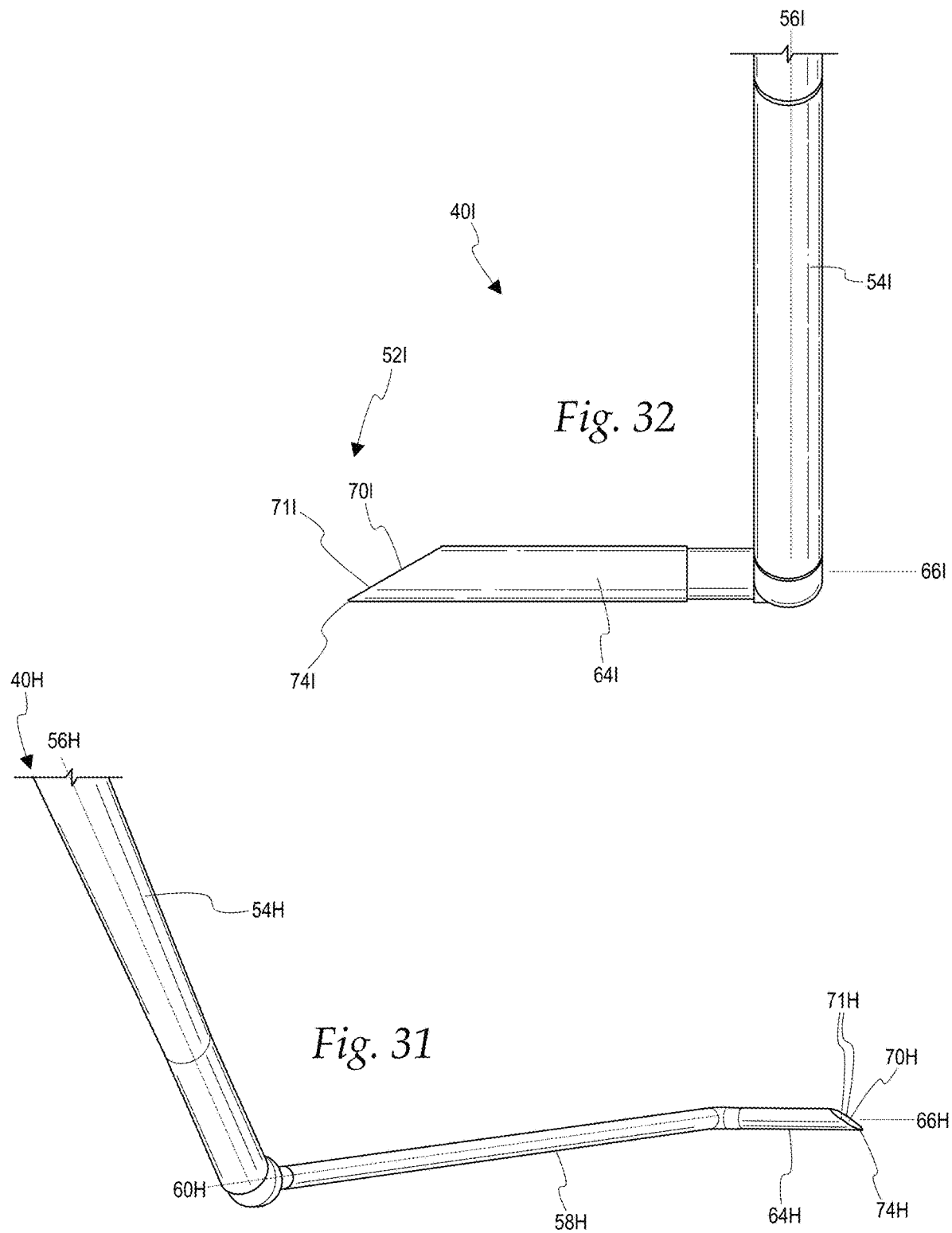

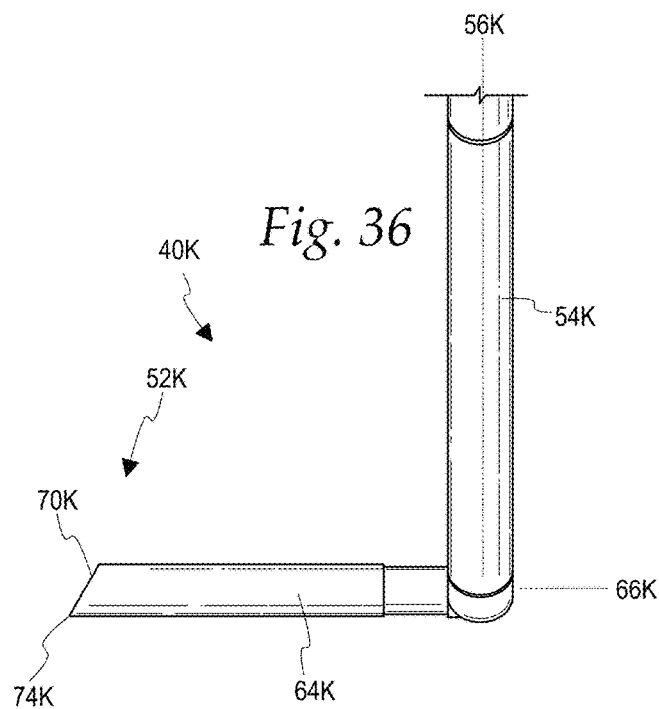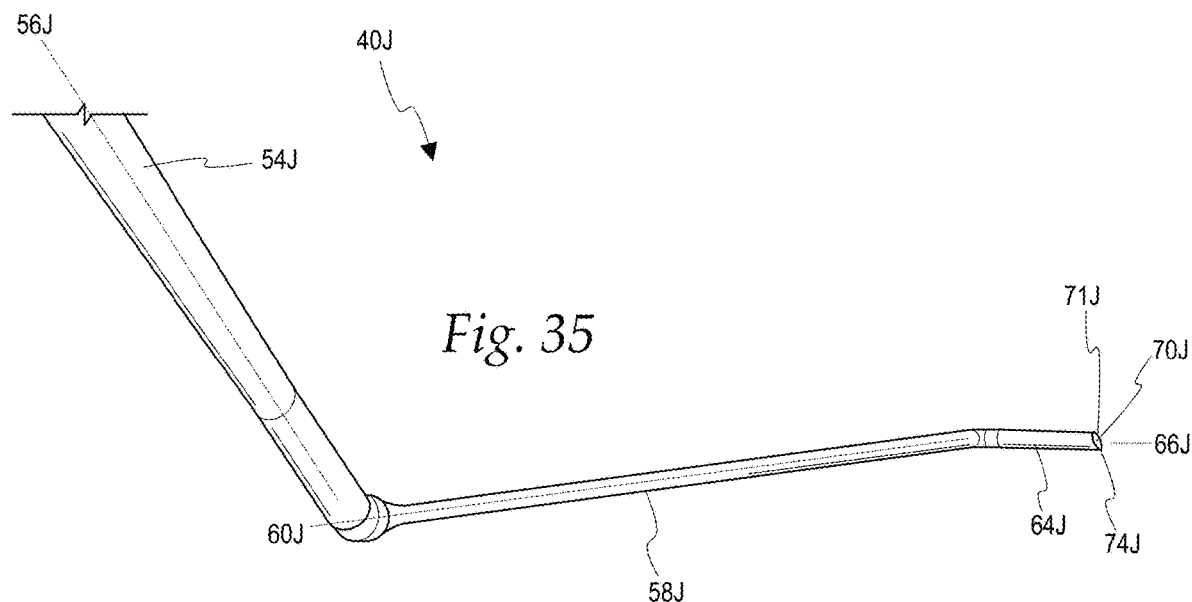

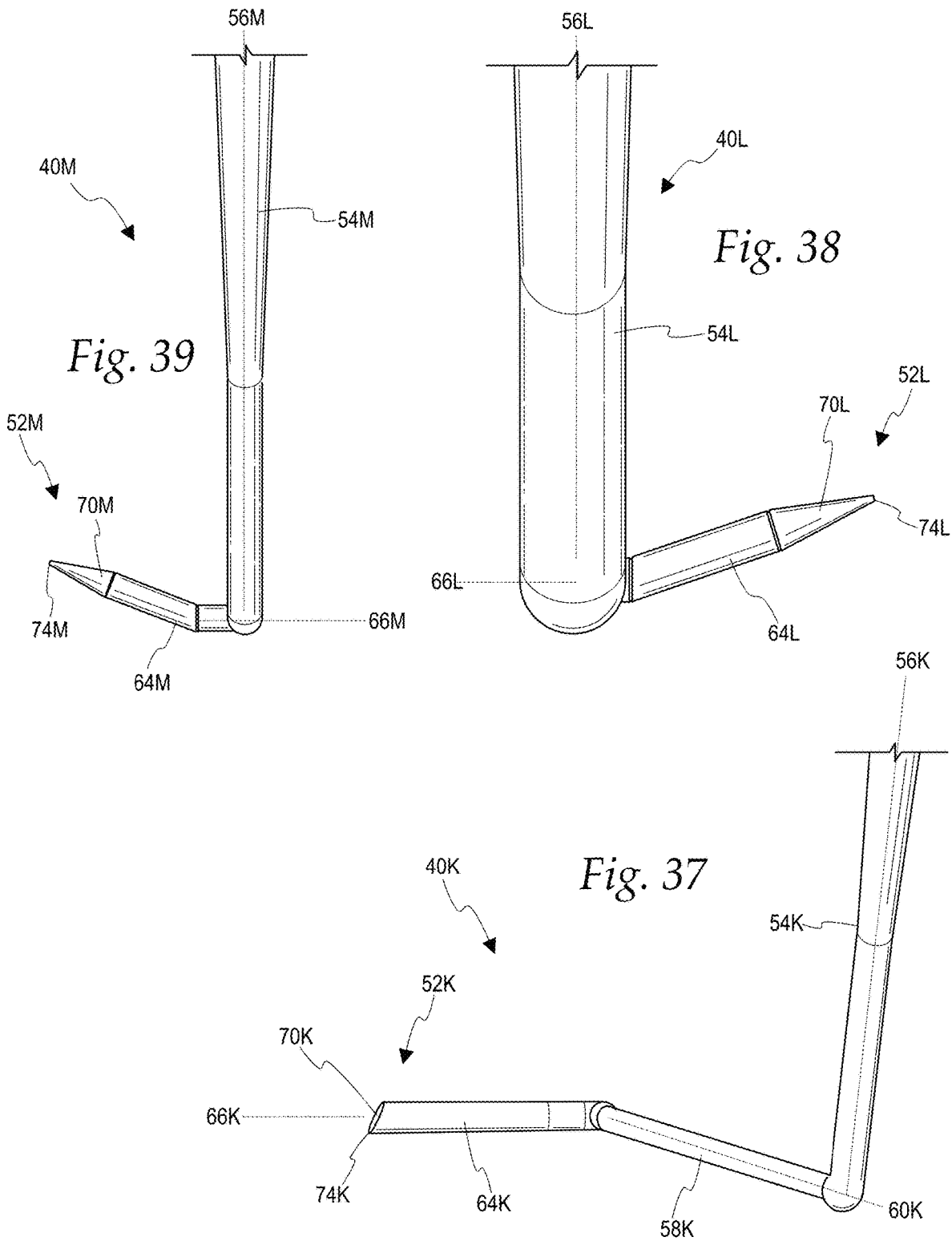

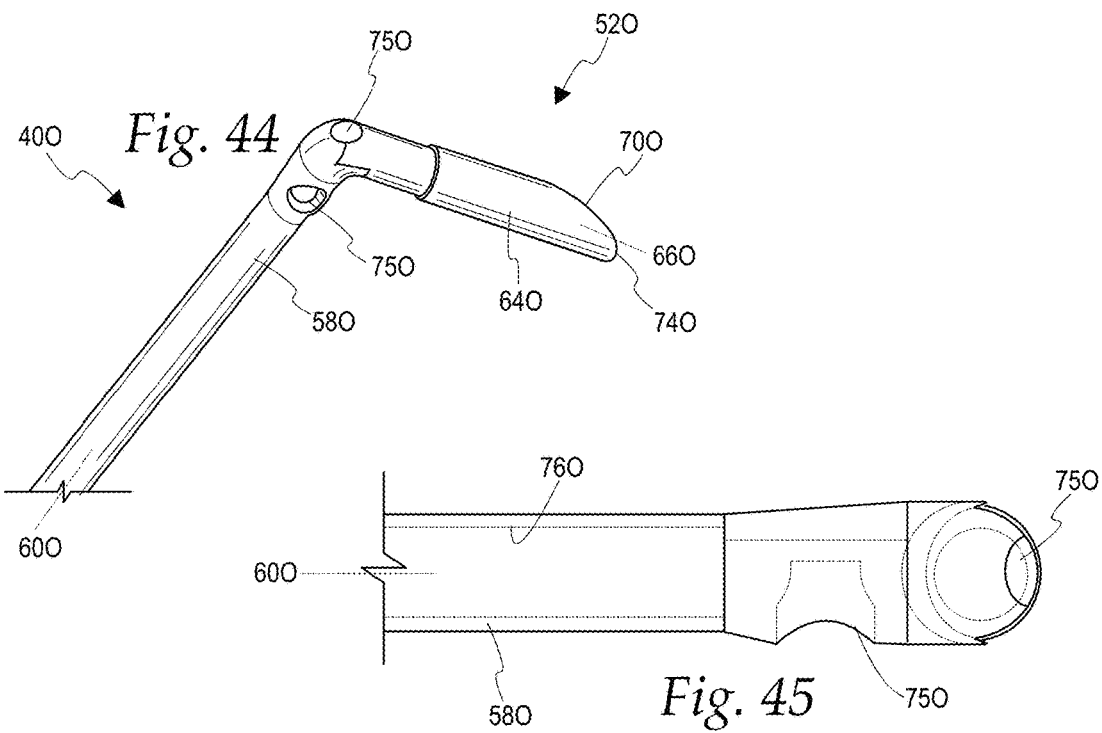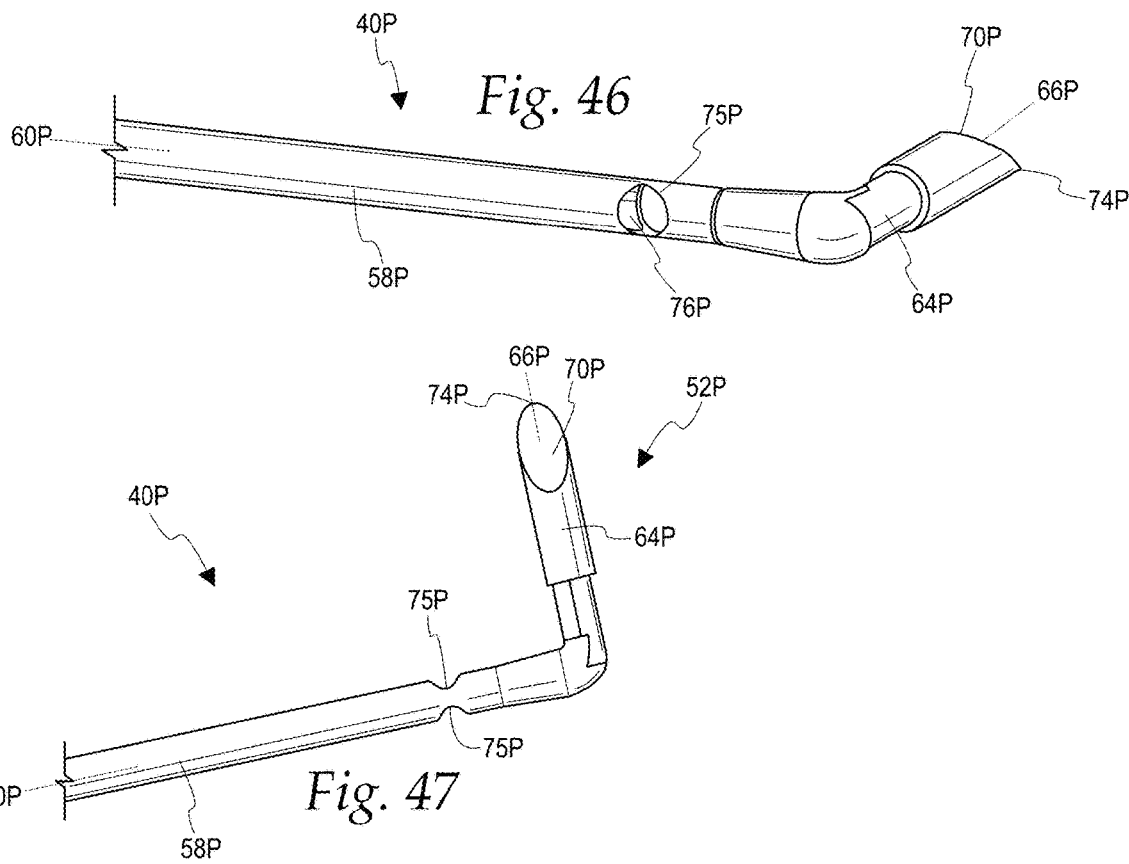

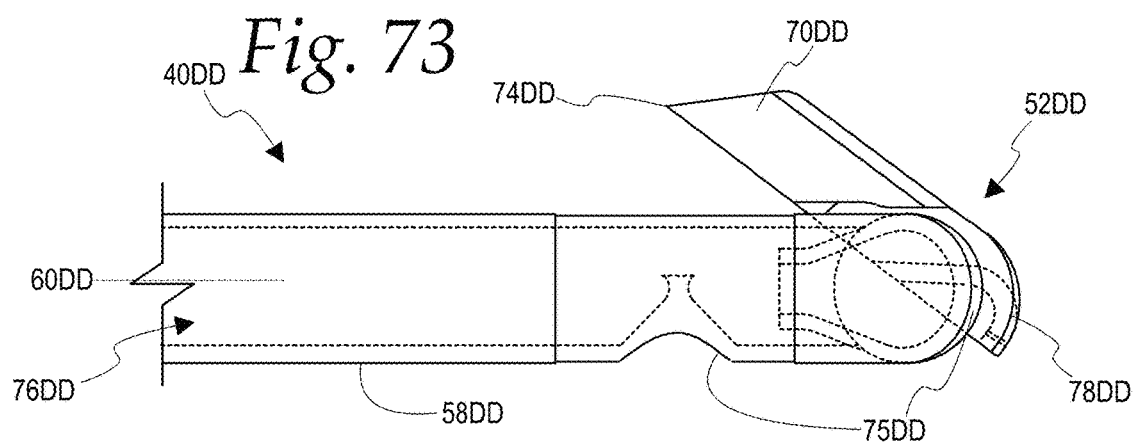
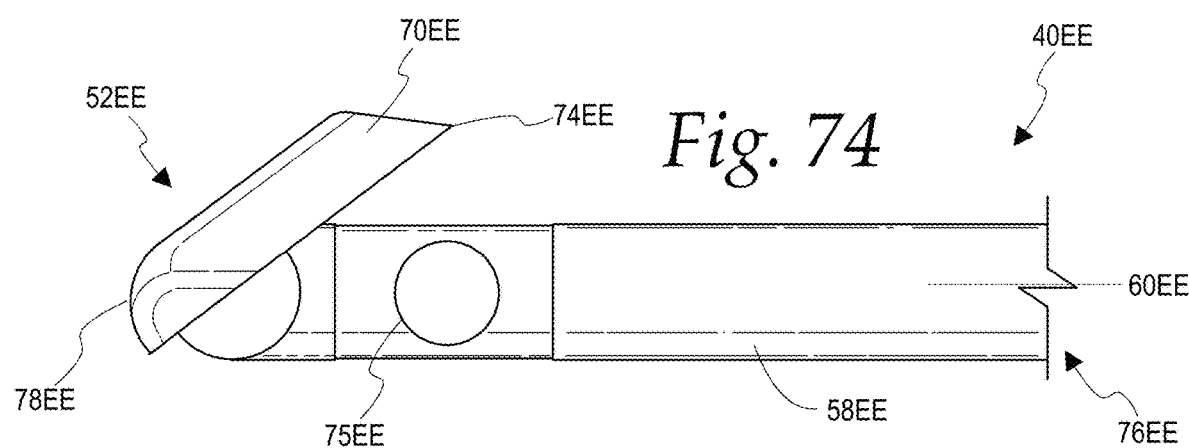
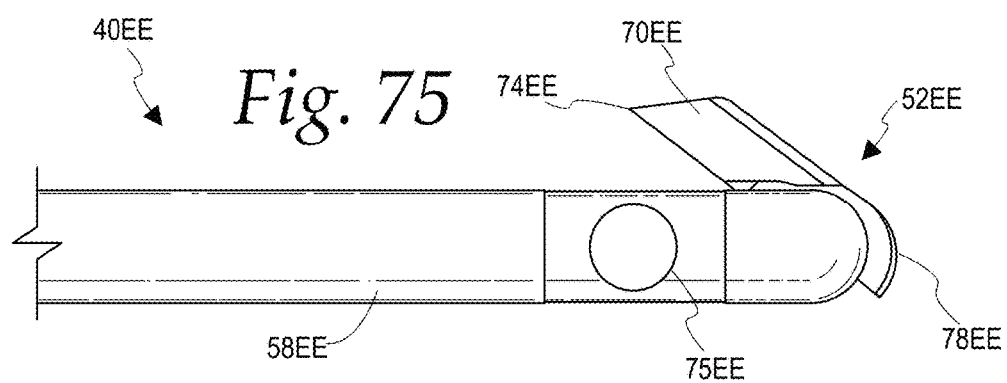

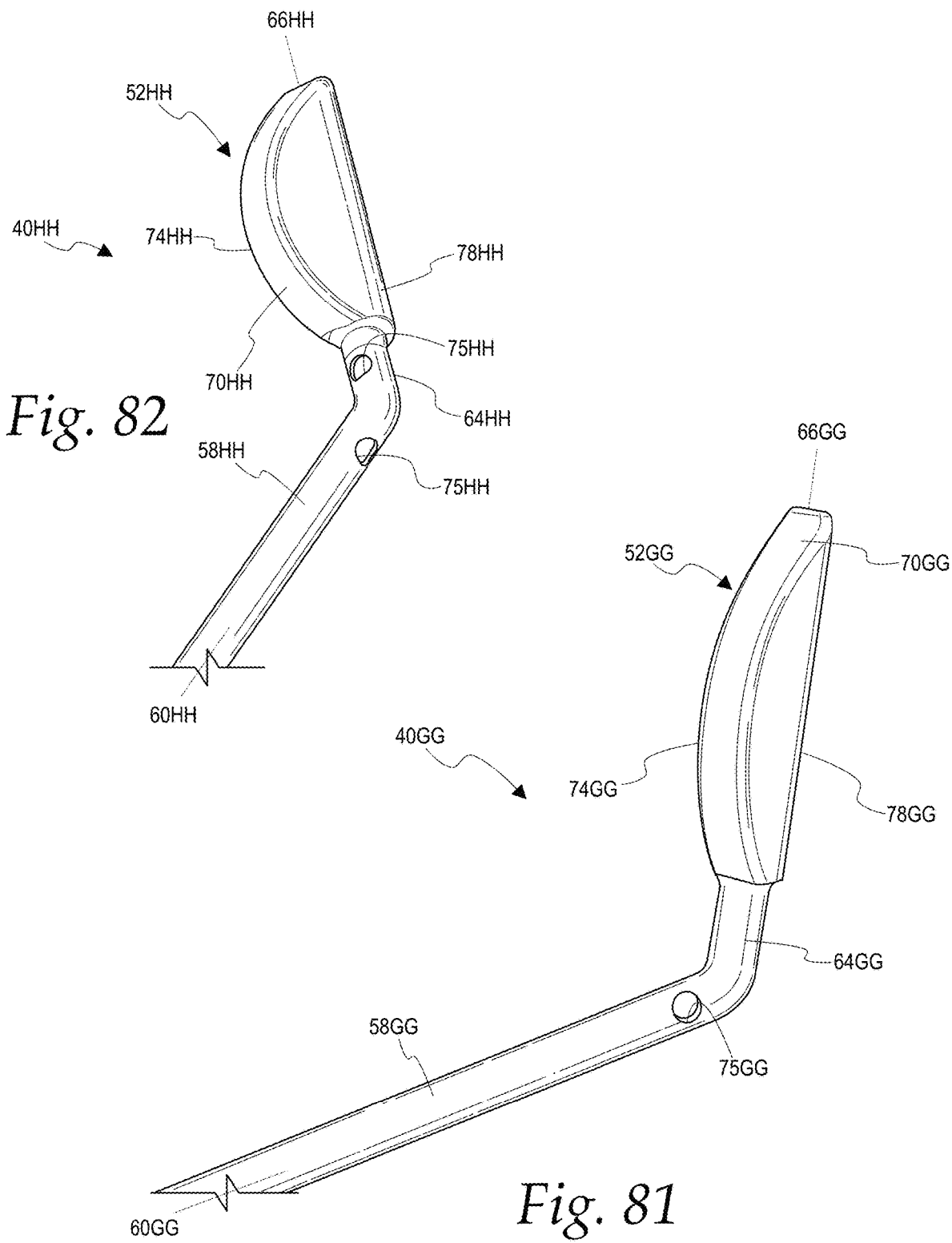

SURGICAL INSTRUMENTS FOR ANTERIOR GONIOTOMY

PRIORITY

The present application claims priority to, and is a continuation of, U.S. patent application Ser. No. 18/637,133, filed on Apr. 16, 2024, which is a bypass continuation of PCT Application No. PCT/US2023/018590, filed on Apr. 14, 2023, which claims the benefit of U.S. Provisional Patent Application No. 63/341,485, filed on May 13, 2022, the entire contents of all patents and applications referred to herein are incorporated herein by reference in their entireties.

FIELD OF THE INVENTION

The present invention relates to micro-surgical instruments for performing ophthalmological procedures for treatment of eye diseases, such as glaucoma, and more particularly to surgical instruments to facilitate an anterior goniotomy procedure.

BACKGROUND OF THE INVENTION

Goniotomy was initially described as a surgical procedure to treat congenital and developmental glaucomas that are caused by a developmental abnormality in the trabecular outflow system. As a result of this abnormality, the trabecular meshwork itself becomes thicker and these changes lead to elevated intraocular pressure that can damage the internal structures of the eye, including the optic nerve leading to the development of glaucoma. Later, goniotomy was found to lower eye pressure in adults.

The purpose of a goniotomy is to selectively cleave the abnormal trabecular tissue in order to improve the flow of aqueous from the eye, which in turn lowers the intraocular pressure (IOP). Lowering the IOP helps to stabilize the enlargement of the cornea and the distension and stretching of the eye that often occur in congenital/developmental glaucoma. Importantly, once the aqueous outflow improves, damage to the optic nerve is halted and may be reversed. The patient's visual acuity may improve after surgery. In adults, goniotomy cleaves open diseased outflow tissues similar to its effect of decreasing outflow resistance in the childhood glaucomas.

The goniotomy procedure can restore normal drainage of aqueous humor from the eye by cleaving a segment of the trabecular meshwork, thus allowing the aqueous humor to drain through the open area from which the strip of trabecular meshwork has been cleaved. The goniotomy procedure and certain prior art instruments useable to perform such procedure are described in U.S. Pat. No. 6,979,328, hereby incorporated by reference in its entirety.

At present there remains a need in the art for the development of improved, easy to use, inexpensive, minimally invasive instruments useable to perform the goniotomy procedure, or other similar procedures, to reduce intraocular pressure.

BRIEF SUMMARY OF THE INVENTION

In accordance with one broad form of the present invention, a micro-surgical instrument is disclosed which is particularly configured to facilitate performing an anterior goniotomy for the treatment of glaucoma. The instrument includes a specifically configured tip portion which facilitates formation of a specific, unique cleavage plane directly below Schwalbe's line to enhance drainage of aqueous humor from the eye.

In one preferred form of the invention, the instrument includes a hand grip having an elongated configuration, with proximal and distal ends. The instrument includes a tip connected to the distal end of the hand grip. The tip has a cutting means for creating a trabecular cleavage plane just below Schwalbe's line.

In one preferred form of the invention, the tip includes a base portion extending from the distal end of the hand grip portion and extending along a base portion axis. The tip includes an intermediate portion extending from the base portion along an intermediate portion axis that is transverse to the base portion axis. The tip further includes a terminal portion extending from the intermediate portion along a terminal portion axis that is transverse to the intermediate portion axis. The terminal portion includes the cutting means.

In yet another form of the invention, the cutting means has the form of a pair of sloping, arcuate cutting surfaces that join to define an arcuate cutting edge. Preferably, the arcuate cutting edge defines an edge axis that is angled between about 30 degrees and about 50 degrees relative to a plane containing the terminal portion axis and the intermediate portion axis. More preferably, the edge axis is angled about 40 degrees relative to the plane containing the terminal portion axis and the intermediate portion axis.

According to one preferred form of the invention, the terminal of the tip includes a blunted surface located opposite (forward of, relative to the hand grip) the cutting means.

According to another preferred form of the invention, the base portion axis extends generally parallel to a hand grip axis, and the intermediate portion axis is angled between about 130 and about 160 degrees relative to the base portion axis.

According to another preferred form of the invention, the cutting means faces rearward toward the hand grip.

In still another form of the present invention, the terminal portion of the tip includes a blunted surface opposite the cutting means, and the cutting means is located closer to the hand grip than the blunted surface.

In another form of the present invention, the cutting means has a beveled configuration that defines a semi-circular, arcuate cutting edge.

In another form of the present invention, the hand grip includes either: (i) a reservoir for accommodating an irrigating fluid; or (ii) a connection for communicating with an external irrigation fluid supply source.

In accordance with one broad form of the present invention, a method of using a surgical instrument to treat the trabecular meshwork of the eye is disclosed. The method includes a first step of obtaining an inventive surgical instrument having at least a hand grip with an elongated configuration, with proximal and distal ends. The instrument includes a tip connected to the distal end of the hand grip. The tip has a cutting means for creating a cleavage plane just below (posterior of along the optical axis) Schwalbe's line in an eye. The method includes the further step of gripping the hand grip to bring the cutting means into contact with the trabecular meshwork at or below Schwalbe's line. The method includes the further step of incising the trabecular meshwork anteriorly, so that the tissue separates from Schwalbe's line to varying degrees.

In one form of the present invention, the cutting means of the instrument is an elliptical, planar, sloping surface that terminates in a distal, arcuate cutting edge.

In another form of the present invention, the cutting means of the instrument is a conical surface which terminates in a distal, pointed cutting edge. Preferably, the pointed cutting edge or point is angled about forty degrees relative to the axis of the terminal portion of the tip.

In another form of the present invention, the cutting means of the instrument has a tapering configuration defining faces that converge and terminate in a blunted, rounded distal edge.

According to yet another form of the present invention, the cutting means has a tapering configuration defining a concave face that terminates in a spatulated distal edge.

In one broad form of the present invention, the instrument may include an internal passage that terminates in at least one irrigation port to direct a flow of an irrigation fluid generally from the distal end of the instrument.

In another form of the present invention, the terminal portion axis of the instrument is angled between about 90 and about 140 degrees relative to the intermediate portion axis, and more preferably angled about 120 degrees.

BRIEF DESCRIPTION OF THE DRAWINGS

In the accompanying drawings forming part of the specification, in which like numerals are employed to designate like parts throughout the same, FIG. 1 is a left-side elevation view of a first embodiment of a surgical instrument according to the present invention;

FIG. 2 is a top plan view of the instrument of FIG. 1;

FIG. 3 is an isometric view, taken from above and the right side, of the instrument of FIG. 1;

FIG. 4 is an enlarged, isometric view, of the operative, distal tip portion of the instrument of FIG. 3;

FIG. 5 is a greatly enlarged, fragmentary, left-side elevation view of the distal tip portion of the instrument shown in FIG. 1;

FIG. 6 is a greatly enlarged, fragmentary, top plan view of the distal tip portion of the instrument shown in FIG. 1;

FIG. 7 is a left-side elevation view of a second embodiment of a surgical instrument according to the present invention;

FIG. 8 is a top plan view of the instrument of FIG. 7;

FIG. 9 is an isometric view, taken from above and the right side, of the instrument of FIG. 7;

FIG. 10 is an enlarged, isometric view, of the distal portion of the instrument of FIG. 7;

FIG. 11 is a greatly enlarged, fragmentary, left-side elevation view of the distal tip portion of the instrument shown in FIG. 7;

FIG. 12 is a greatly enlarged, fragmentary, top plan view of the distal tip portion of the instrument shown in FIG. 7;

FIG. 12A shows the formation of a trabecular leaflet or flap at 1-month post operation;

FIG. 12B shows the formation of a trabecular leaflet or flap at 12-months post operation;

FIG. 12C shows the formation of a trabecular leaflet or flap at 17-months post operation;

FIG. 12D shows the classic formation of a trabecular leaflet or flap;

FIG. 15 is an enlarged, isometric view, of the operative, distal tip portion of the instrument of FIG. 14;

FIG. 16 is a greatly enlarged, fragmentary, front elevation view of the operative, distal tip portion of the instrument of FIG. 14;

FIG. 17 is a fragmentary, isometric view of a fourth embodiment of a surgical instrument according to the present invention, wherein the instrument is configured as a right-angled instrument;

FIG. 18 is a greatly enlarged, fragmentary, isometric view, of the operative, distal tip portion of the instrument of FIG. 17;

FIG. 19 is a fragmentary, isometric view of a fifth embodiment of a surgical instrument according to the present invention, wherein the instrument is configured as a left-angled instrument;

FIG. 29 is a fragmentary, isometric view from the left and front of the instrument of FIG. 28;

FIG. 30 is a fragmentary, front elevation view of a ninth embodiment of a surgical instrument according to the present invention, wherein the instrument is configured as a right-angled instrument and only the tip portion is visible;

FIG. 31 is a fragmentary, isometric view from the right and front of the instrument of FIG. 30;

FIG. 32 is a fragmentary, front elevation view of a tenth embodiment of a surgical instrument according to the present invention, wherein the instrument is configured as a left-angled instrument and only the tip portion is visible;

FIG. 35 is a fragmentary, isometric view from the right and front of the instrument of FIG. 34;

FIG. 36 is a fragmentary, front elevation view of a twelfth embodiment of a surgical instrument according to the present invention, wherein the instrument is configured as a left-angled instrument and only the tip portion is visible;

FIG. 37 is a fragmentary, isometric view from the front and left side of the instrument of FIG. 36;

FIG. 38 is a fragmentary, front elevation view of a thirteenth embodiment of a surgical instrument according to the present invention, wherein the instrument is configured as a right-angled instrument and only the tip portion is visible;

FIG. 39 is a fragmentary, front elevation view of a fourteenth embodiment of a surgical instrument according to the present invention, wherein the instrument is configured as a left-angled instrument and only the tip portion is visible;

FIG. 44 is a fragmentary, isometric view from below of a sixteenth embodiment of a surgical instrument according to the present invention, wherein the instrument is configured as a left-angled instrument and only part of the tip portion is visible;

FIG. 45 is a right side elevation view of the instrument of FIG. 44 showing the interior of the instrument;

FIG. 46 is a fragmentary, isometric view from below of a seventeenth embodiment of a surgical instrument according to the present invention, wherein the instrument is configured as a left-angled instrument and only part of the tip portion is visible;

FIG. 47 is a fragmentary, top plan view of the instrument of FIG. 46;

FIG. 71 shows the internal features of the instrument;

FIG. 73 is a greatly enlarged, fragmentary, right elevation view of the instrument of FIG. 70, and FIG. 73 shows the internal features of the instrument;

FIG. 74 is a greatly enlarged, fragmentary, left elevation view of a thirty-second embodiment of a surgical instrument according to the present invention, wherein the instrument is configured as a left-angled instrument and only part of the tip portion is visible;

FIG. 75 is a greatly enlarged, fragmentary, right elevation view of the instrument of FIG. 74;

FIG. 78 shows the internal features of the instrument;

FIG. 81 is a fragmentary, top plan view of the portion of the instrument shown in FIG. 80;

FIG. 82 is a greatly enlarged, fragmentary, isometric view from above of a thirty-fifth embodiment of a surgical instrument according to the present invention, wherein the instrument is configured as a left-angled instrument and only part of the tip portion is visible;

DETAILED DESCRIPTION OF THE PREFERRED EMBODIMENTS

Figure 12A:
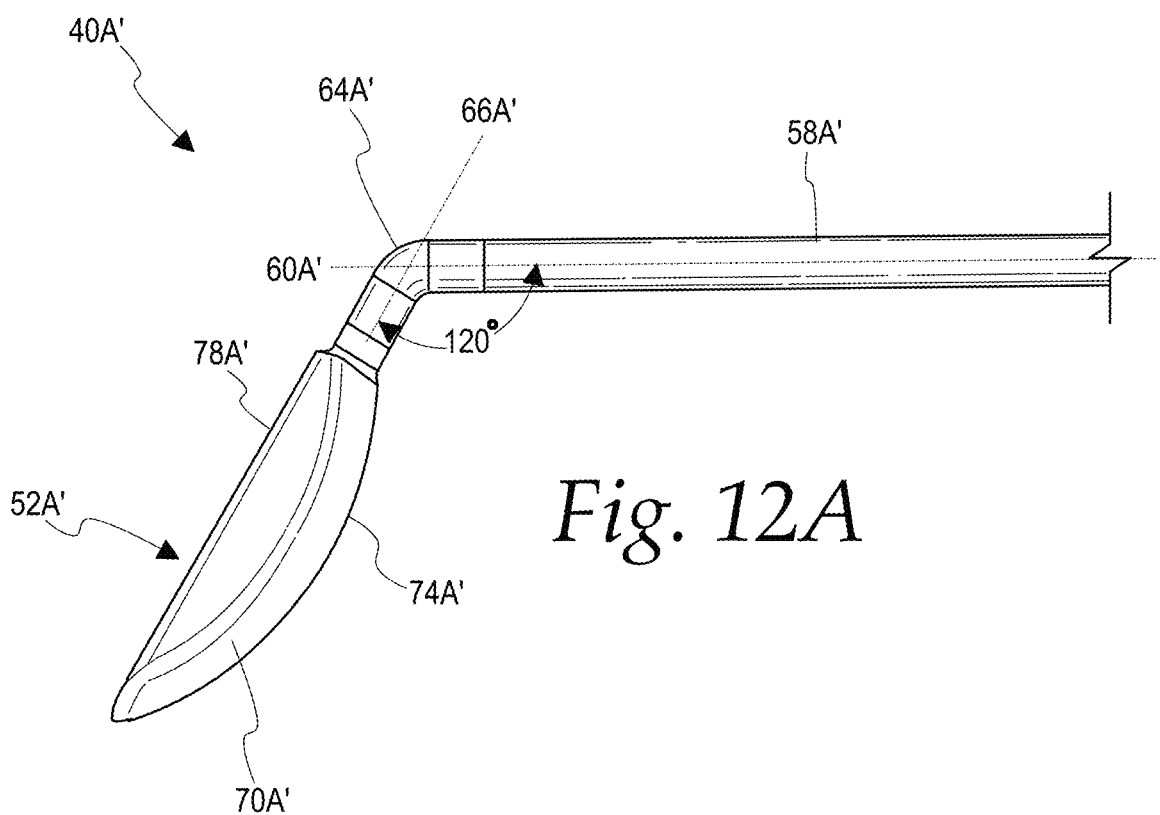
FIG. 12A is a greatly enlarged, fragmentary, top plan view, of a distal portion of a variation of the second embodiment of a surgical instrument according to the present invention.

With reference to FIGS. 1-6, in accordance with first illustrated embodiment of the present invention, a present goniotomy surgical instrument 40 includes a hand piece or hand grip 44 for being gripped by a user of the instrument 40. The grip 44 has an elongated configuration, including a proximal end 46 and a distal end 48 defining a hand grip axis 50 extending therebetween. FIGS. 1-6 show a first variation of the instrument 40 for use as a right-angled instrument. FIGS. 7-12 show a left-angled variation of the instrument 40A, which will be discussed in greater detail below. It is further contemplated that this embodiment of the instrument 40 may also be configured as a non-angled, straight instrument. Each of these variations of the instrument 40 and 40A are configured to contact specific angles, arcs, or portions of the trabecular meshwork of a patient's eyes, as will be discussed in detail below. The hand grip 44 can be provided with either a rounded or a flattened configuration and is preferably knurled for ease of grip. Furthermore, the hand grip 44 may be a cannula hub or fitting with means for being attached to a larger machine, irrigation system, or commercial irrigating handpiece (e.g., screw threading, snap-fit connection, luer lock connection, friction fit, locked, etc.). The numbered features of the embodiments of the instruments 40 and 40A illustrated and discussed herein are designated generally with a number where such features are analogous in structure and function.

With reference now to FIG. 4, the instrument 40 includes a tip 52 that extends, either directly from the distal end 48 of the hand grip 44, or indirectly from the distal end 48 of the hand grip 44 via one or more straight or angled shank portions depending on the right, left, or straight designed use of the instrument 40.

In the illustrated first preferred embodiment of the instrument 40, the tip 52 includes a base portion 54 that extends from the distal end 48 of the hand grip 44 and defines a base portion axis 56 through its geometric center. The base portion axis 56 is substantially parallel to, and coincident with, the central axis 50 of the hand grip 44. The tip 52 further includes an intermediate portion 58 extending from the base portion 54 along an intermediate portion axis 60 that is transverse or angled relative to the base portion axis 56. Preferably, the intermediate portion axis 60 is angled between about 130 degrees and 160 degrees relative to the base portion axis 56, and more preferably angled about 145 degrees. The tip 52 includes a terminal portion 64 extending from the intermediate portion 58 along a terminal portion axis 66 that is transverse to the intermediate portion axis 60. Preferably, the terminal portion axis 66 is angled between about 90 degrees and about 140 degrees relative to the intermediate portion axis 60, and more preferably is angled about 120 degrees. The terminal portion 64 includes cutting means for creating a trabecular leaflet at, or just minimally posterior to or below, Schwalbe's line in an eye. The inventors have found that increasing the angle between axes 66 and 60 from about 90 degrees to about 120 degrees greatly improves the user's ability to perform the surgical operation of creating the leaflet.

Figure 13A:
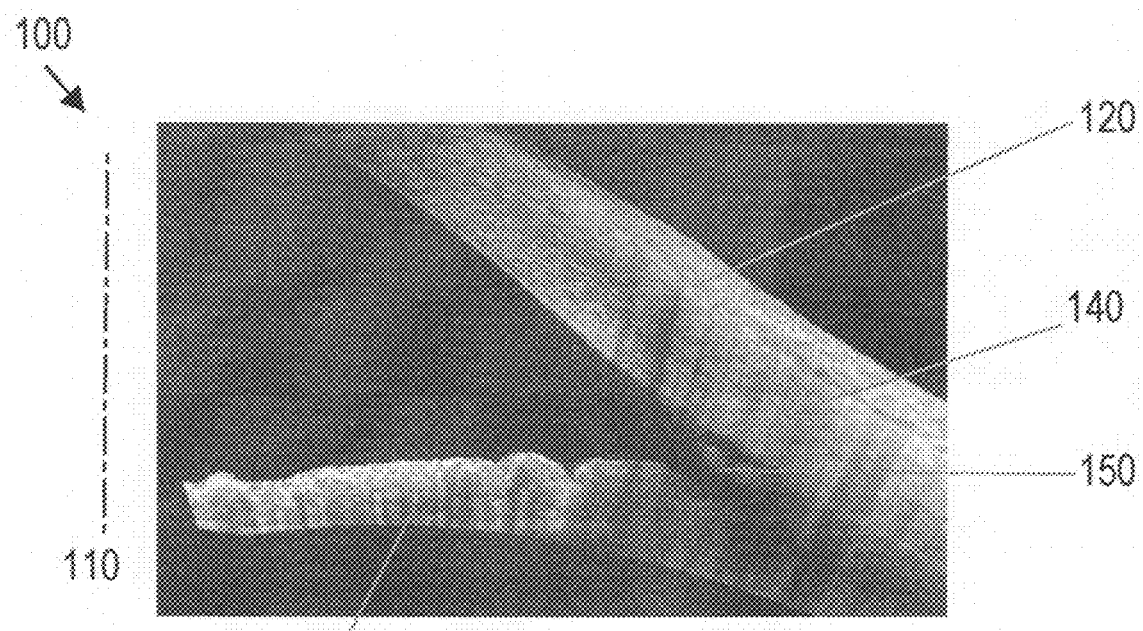
FIG. 13A is an optical coherence tomography image of an eye subsequent to an operation with an instrument according to the present invention.
Figure 13B:
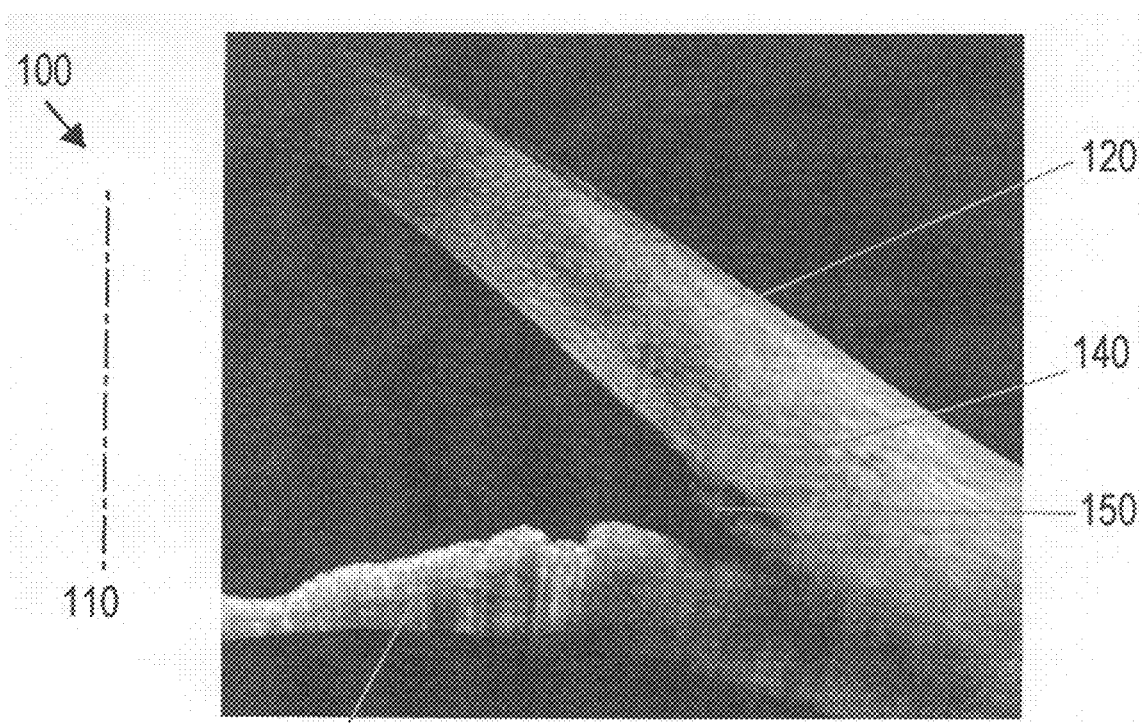
FIG. 13B is an optical coherence tomography image of an eye subsequent to an operation with an instrument according to the present invention.
Figure 13C:
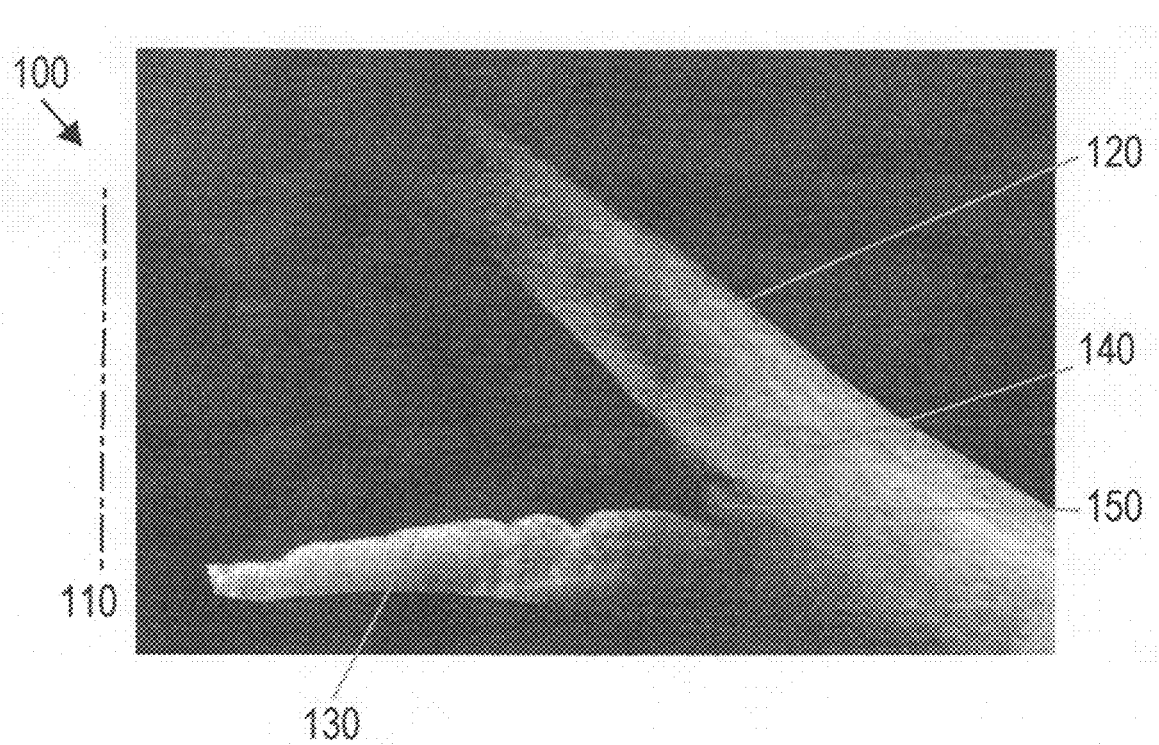
FIG. 13C is an optical coherence tomography image of an eye subsequent to an operation with an instrument according to the present invention.
Figure 13D:
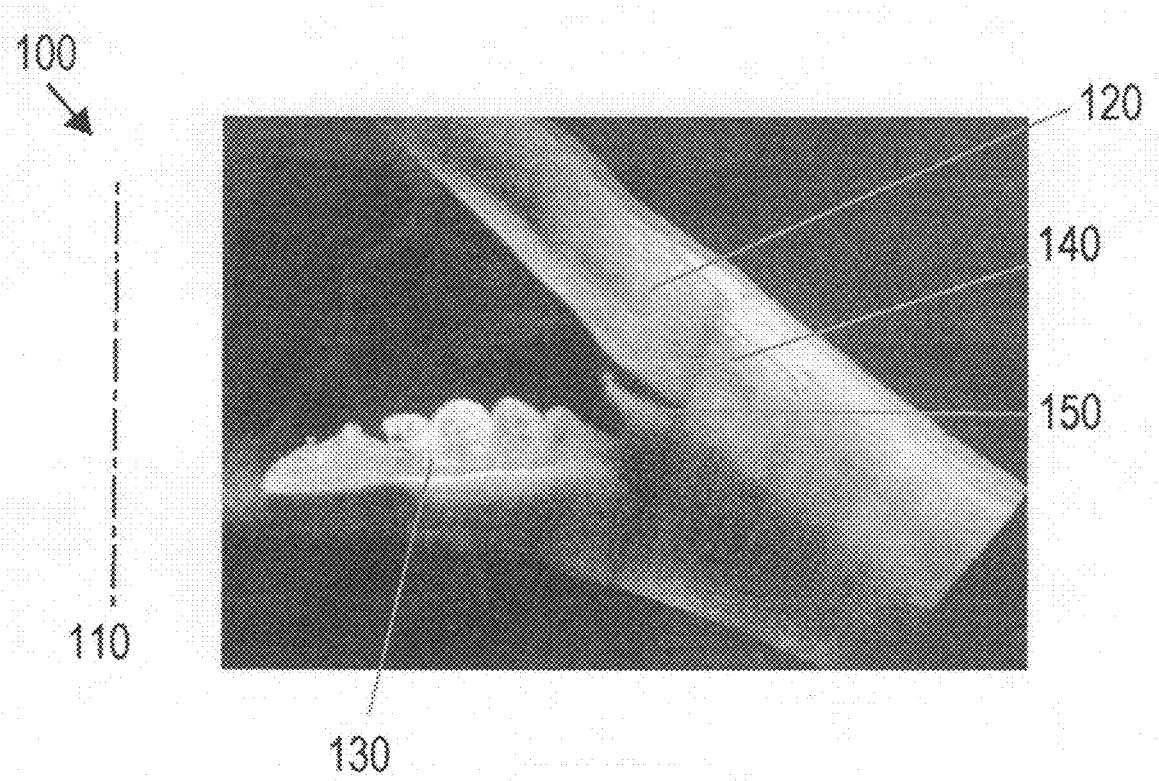
FIG. 13D is another optical coherence tomography image of an eye subsequent to an operation with an instrument according to the present invention.
Figure 14:
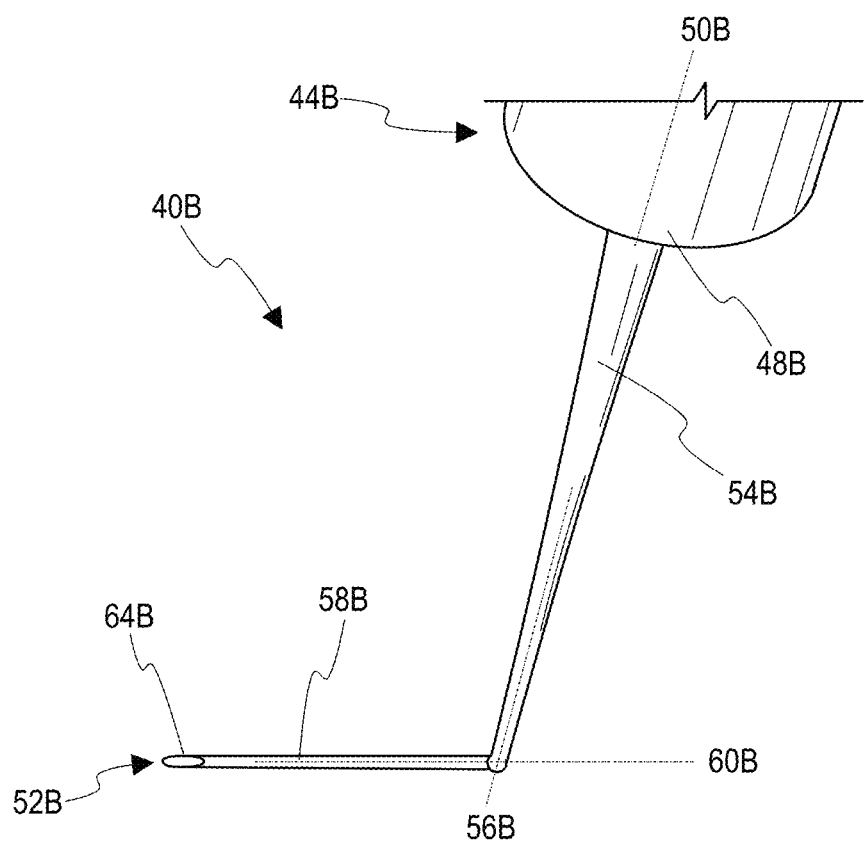
FIG. 14 is a fragmentary, front elevation view of a third embodiment of a surgical instrument according to the present invention, wherein the instrument is configured as a left-angled instrument.
Figure 20:
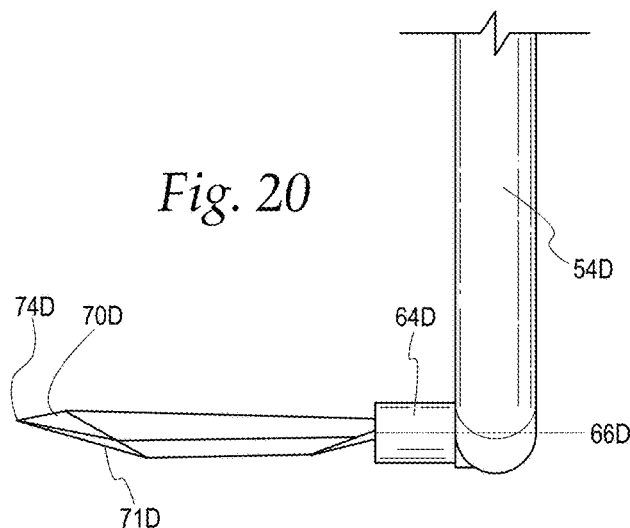
FIG. 20 is a fragmentary, front elevation view of the instrument of FIG. 19.
Figure 21:
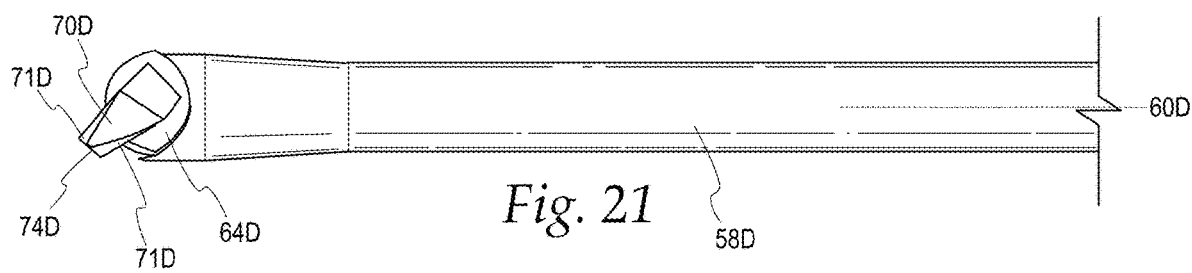
FIG. 21 is a fragmentary, left side elevation view of the instrument of FIG. 19.
Figure 22:
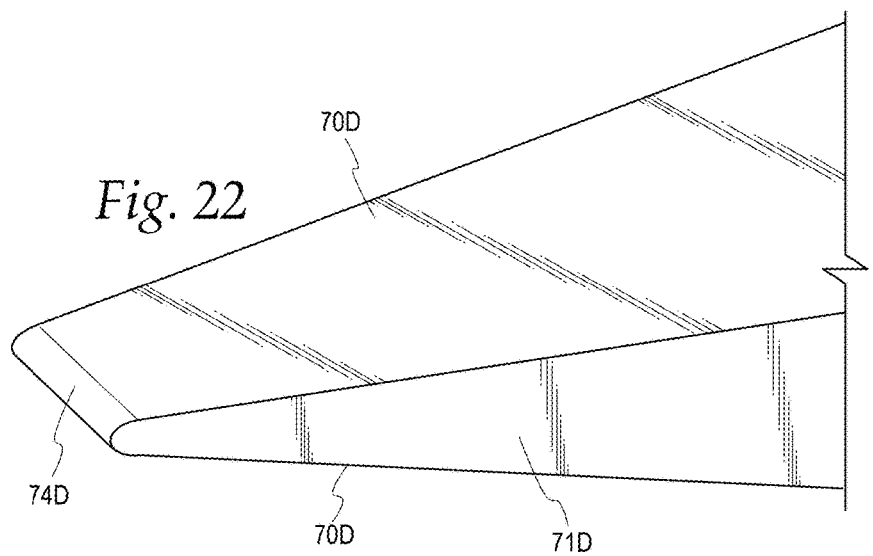
FIG. 22 is a greatly enlarged, fragmentary, isometric view, of the operative, distal tip portion of the instrument of FIG. 19.
Figure 23:
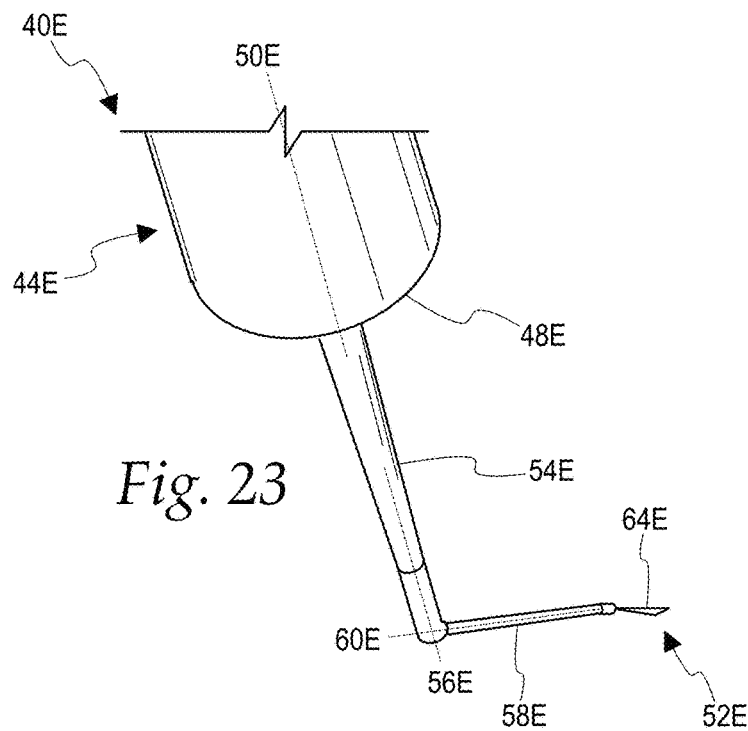
FIG. 23 is a fragmentary, isometric view of a sixth embodiment of a surgical instrument according to the present invention, wherein the instrument is configured as a right-angled instrument.
Figure 24:
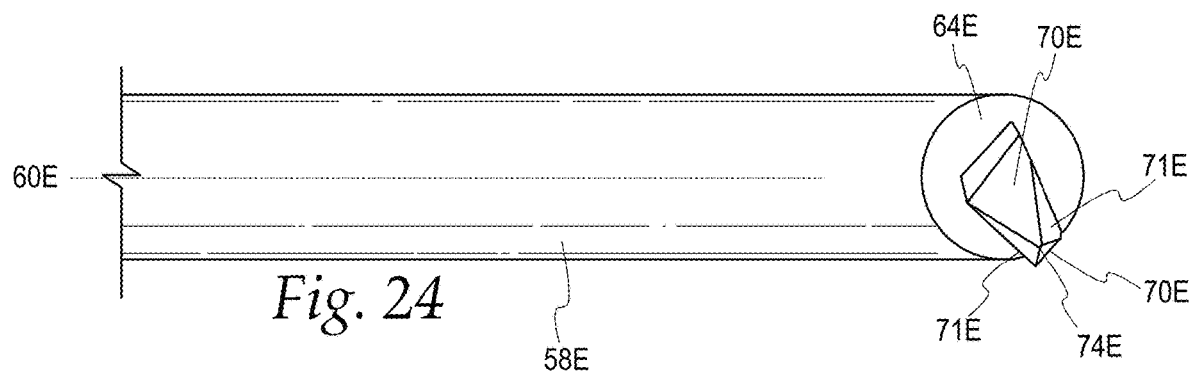
FIG. 24 is a greatly enlarged, fragmentary, right side elevation view of the instrument of FIG. 23.
Figure 25:
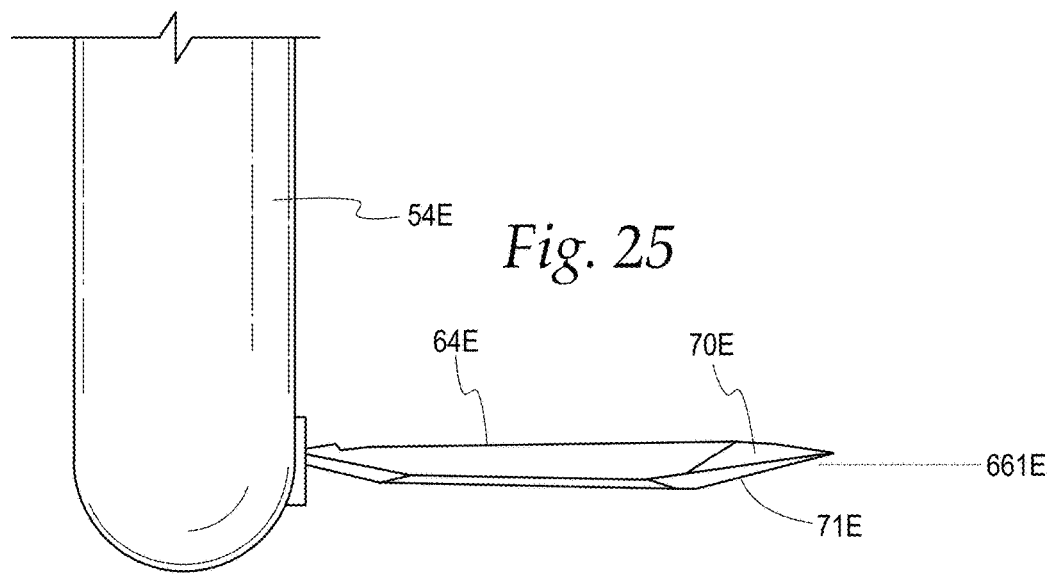
FIG. 25 is a greatly enlarged, fragmentary, front elevation view of the instrument of FIG. 23.
Figure 26:
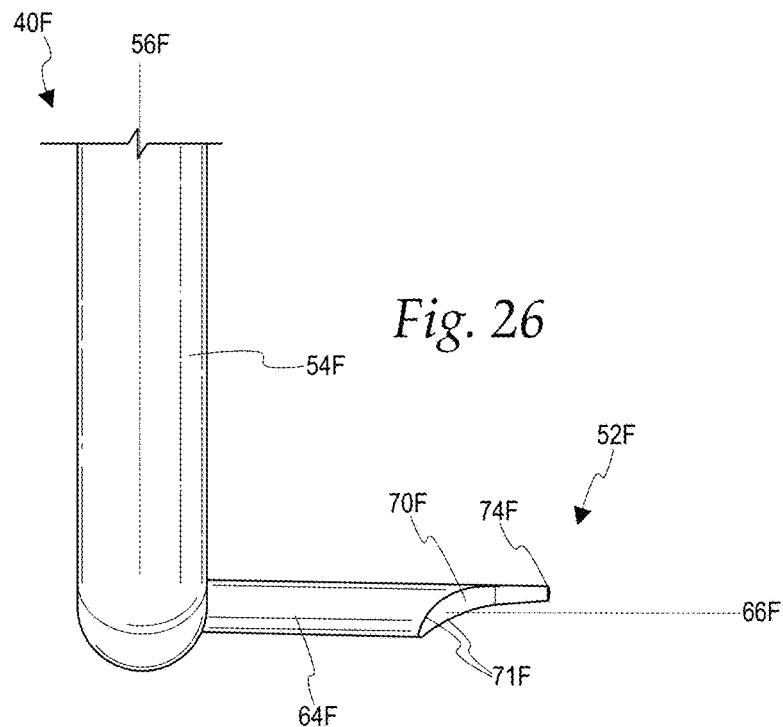
FIG. 26 is a fragmentary, front elevation view of a seventh embodiment of a surgical instrument according to the present invention, wherein the instrument is configured as a right-angled instrument and only the tip portion is visible.
Figure 27:
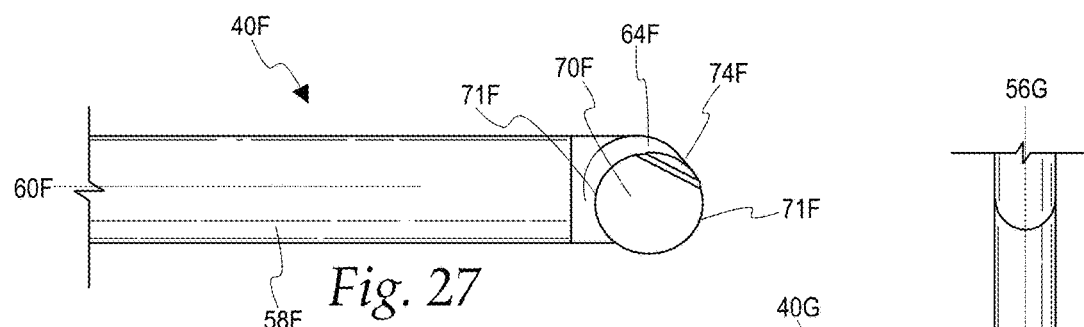
FIG. 27 is a fragmentary, right side elevation view of the instrument of FIG. 26.
Figure 28:
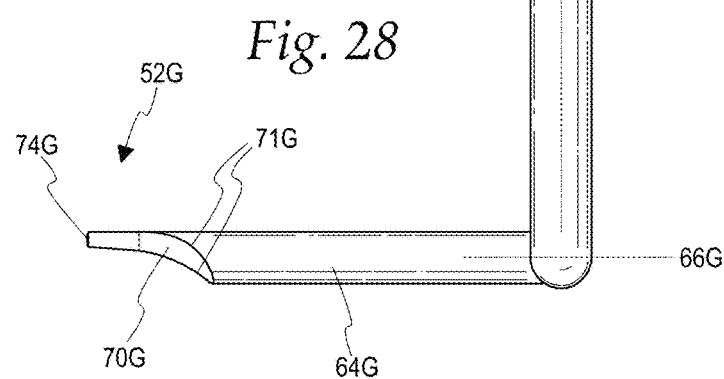
FIG. 28 is a fragmentary, front elevation view of an eighth embodiment of a surgical instrument according to the present invention, wherein the instrument is configured as a left-angled instrument and only the tip portion is visible.
Figure 34:
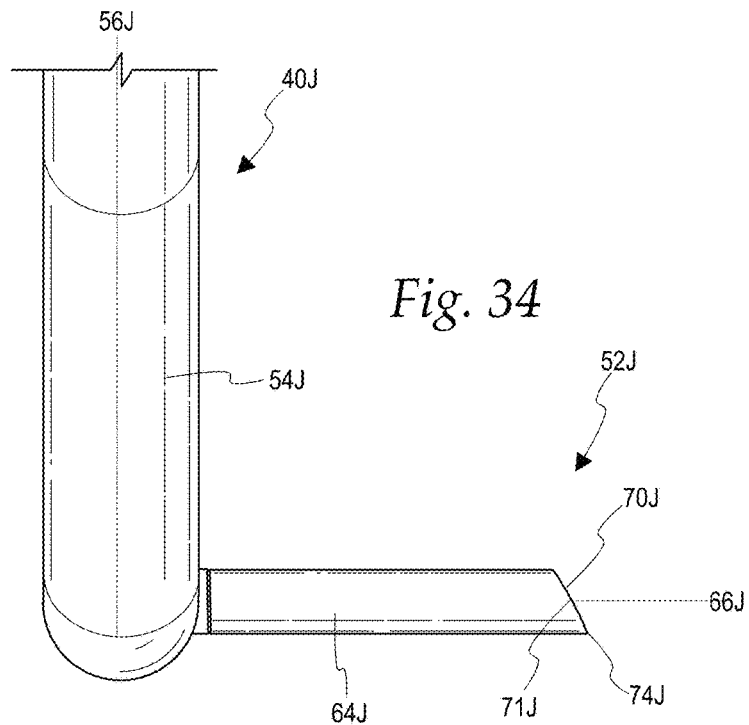
FIG. 34 is a fragmentary, front elevation view of an eleventh embodiment of a surgical instrument according to the present invention, wherein the instrument is configured as a right-angled instrument and only the tip portion is visible.
Figure 33:
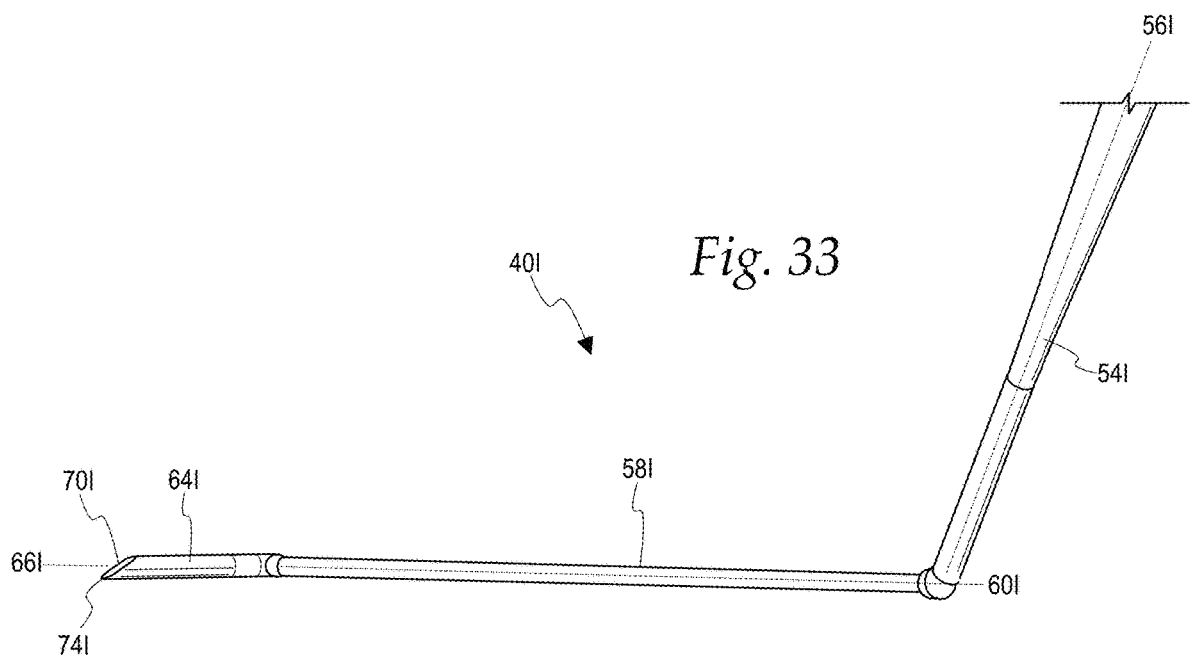
FIG. 33 is a fragmentary, isometric view from the left and front of the instrument of FIG. 32.
Figure 40:
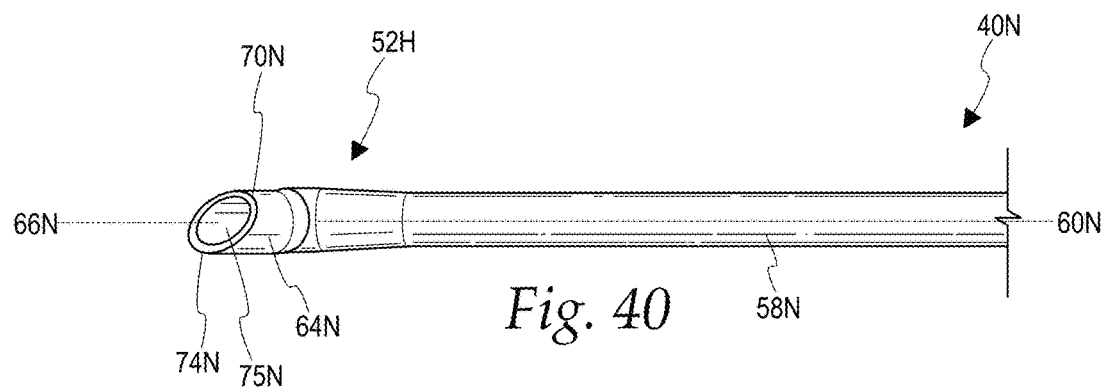
FIG. 40 is a fragmentary, isometric view of a fifteenth embodiment of a surgical instrument according to the present invention, wherein the instrument is configured as a left-angled instrument and only part of the tip portion is visible.
Figure 41:
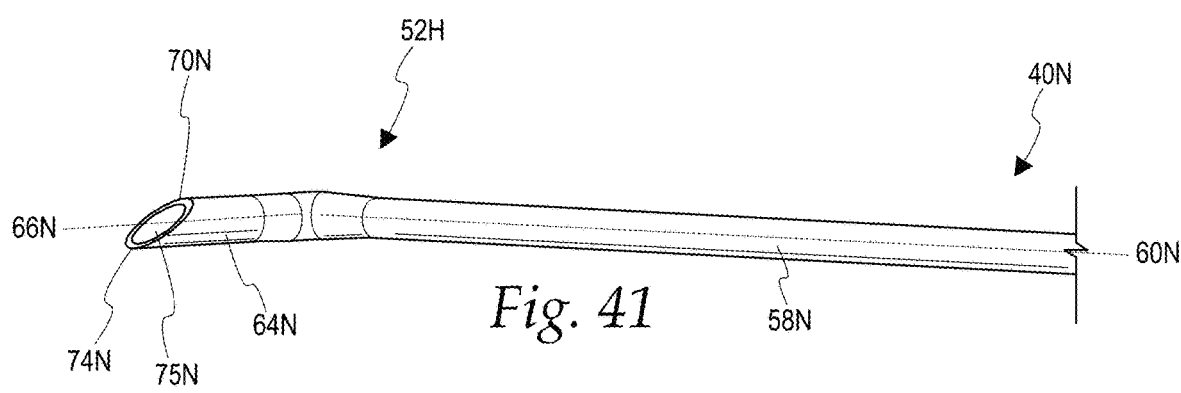
FIG. 41 is another fragmentary, isometric view of the instrument of FIG. 40.
Figure 42:
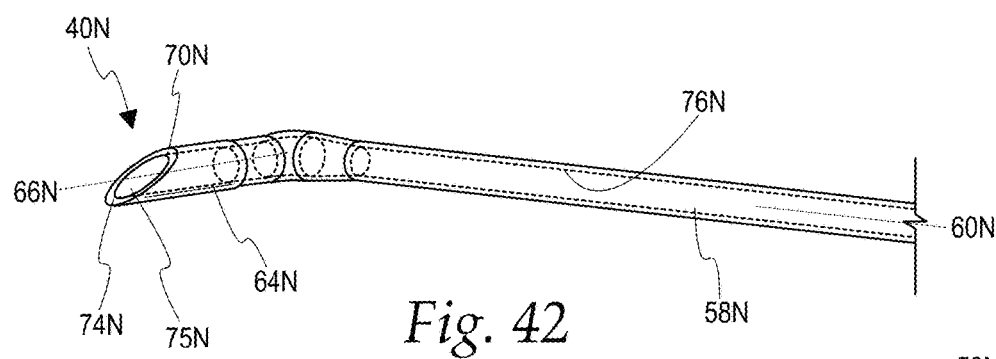
FIG. 42 is another fragmentary, isometric view of the instrument of FIG. 40 showing the interior of the instrument.
Figure 43:
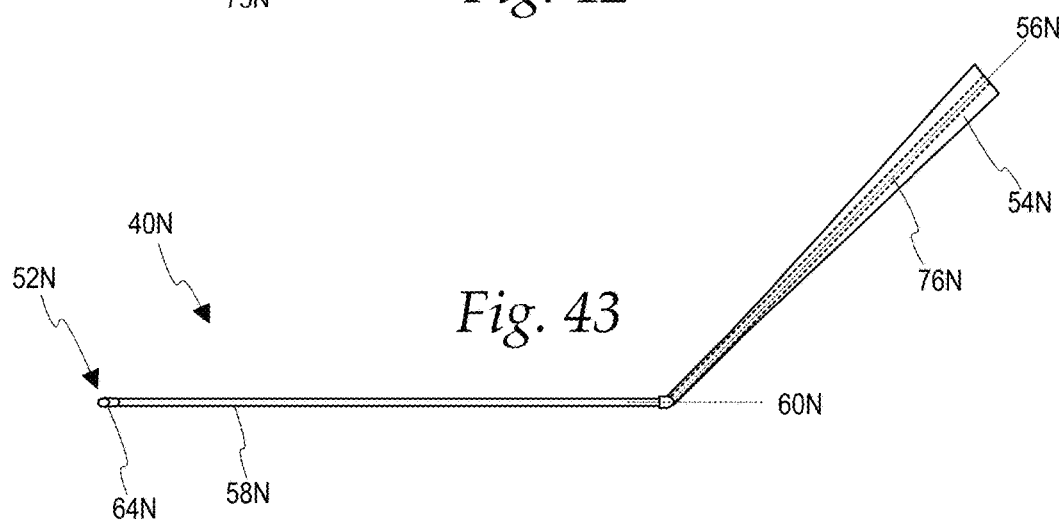
FIG. 43 is a left side elevation view of the instrument of FIG. 40.

With reference to FIGS. 13A-13D, a series of optical coherence tomography images of an eye 100 that has been operated upon by the instrument 40 is shown. Directions referenced herein are generally taken relative to the optical axis 110 (or a line parallel thereto) of such an eye 100, wherein the anterior direction is axially upwardly in FIGS. 13A-13D away from the optic or lens of the eye, and the posterior direction is axially downwardly in FIGS. 13A-13D toward the optic of the eye. FIGS. 13A-13D show the cornea 120, iris 130, and the opening of Schlemm's canal 140 of the eye 100. The inventors have found that the instrument 40 disclosed herein is advantageously configured to safely and efficiently incise the trabecular tissue directly below Schwalbe's line to allow the separated trabecular meshwork or tissue 150 to drop away from the cornea 120 in the posterior direction toward the iris 130. The trabecular leaflet or flap 150, which extends an angle or arc around the optical axis 110, may improve flow through the Schlemm's canal 140 to lower intraocular pressure and reduce the medications required by a patient with glaucoma. FIG. 13A shows the eye 100 after 1 month from the date of the surgery with the instrument 40 of the present invention, FIG. 13B shows the same eye 100 after 12 months from the date of the surgery, and FIG. 13C shows the same eye 100 after 17 months from the date of the surgery. FIG. 13D shows a classic appearance of the trabecular vent in the eye 100 following an iVent surgery with the present invention. The acute angle of the trabecular corneal angle is classic for a post operative appearance of the vent created with the inventive technique. The appearance of this trabecular vent angle is distinctly different from the appearance of angles after other forms of goniotomy, GATT, OMNI, etc.

With reference now to FIGS. 5 and 6, the preferred cutting means of the instrument 40 has the form of a pair of sloping, arcuate cutting surfaces 70 that join to define an arcuate cutting edge 74. The cutting surfaces 70 are preferably semi-circular and define a bevel terminating rearwardly to face the hand grip 44 of the instrument 40 when gripped by a user. As can be seen in FIG. 5, the instrument 40 defines a plane 68 that contains the axes 60 and 66 of the intermediate tip portion 58 and the terminal portion 64 of the tip 52. The arcuate cutting edge 74 defines a central edge axis 80 that is angled between about 30 and 50 degrees, and more preferably about 40 degrees relative to the plane 68. The distal most end of the terminal portion 64, relative to the hand grip 44, is a blunted surface 78 that is opposite the arcuate cutting edge 74. The blunted surface 78 is the furthest portion of the tip 52 away from the hand grip 44.

With reference to FIG. 5, the terminal portion 64 of the tip 52 preferably has a width of about 0.1 mm.

With reference to FIG. 6, the terminal portion 64 of the tip 52 preferably has an operative blade length of about 0.30 mm, along the terminal portion axis 66 and a blade width of about 0.15 mm in the direction normal to the axis 66.

The inventors of the present invention believe that the embodiments of the instrument discussed herein may advantageously permit the surgeon to improve flow through the outflow tissues by disinserting the trabecular meshwork from Schwalbe's line and simultaneously preserving the valve like function inherent to the outflow system. The instruments herein may lower costs for the glaucoma procedure compared to existing surgical instruments with expensive handpieces, and may improve surgical outcomes by reducing the time of the procedure compared to surgeries performed with prior art devices. The instruments disclosed herein may be easier to use by a surgeon, cost less than leading prior art devices on the market, and/or reduce or eliminate post-operative visits to the surgeon by the patient.

The present invention facilitates the creation of a unique incision into the trabecular tissue compared to all other currently know methods for opening the trabecular meshwork, including but not limited to Kahook Dual Blade, OMNI 360 Surgical System, iStent inject, Hydrus, GATT, Hemi-GATT and Tanito Goniotomy. An advantage of the present invention include the precise and selective opening of the anterior most aspect of the trabecular meshwork, essentially just posterior to Schwalbe's line. This selective incision of the trabecular meshwork allows for the cleavage of trabecular meshwork tissue with minimal disruption of the existing intracanalicular valvular system. The cleaved trabecular meshwork is detached from Schwalbe's line, but remains attached to the scleral spur. Depending on the elasticity of the leaflet and other factors including gravity and postoperative healing, the leaflet remains open to varying degrees. This selective anterior cleavage of the trabecular meshwork protects disruption of the microscopic support structures in the angle and theoretically, preserves the pump/valve function within Schlemm's canal.

A further advantage of this procedure is to minimize trauma and preserve the valve system unlike the Kahook Dual Blade, iTrack, Omni 360, GATT prior art, Tanito, Espaillat, trabeculotomy or ABiC procedures. With minimal disruption of the microscopic support structures within Schlemm's canal in the present invention, the potential for reflux of blood due to hypotony is minimized (given that the valve structures remain essentially intact). Additionally, because there is not device or instrument that rubs along or disrupts the back wall of Schlemm's canal, this device also minimizes the risk of disrupting the endothelium lining of Schlemm's canal, any associated vascularized tissue and any of the microscopic intracanalicular canal structures such as valves and microtubes. Also, depending on the degree of glaucomatous disease and valvulardys function, the specific cleavage plane created in the anterior trabecular meshwork mayallow for a stretching of the intracanalicular valve system with improvement in its function. Further, the unique design of the device allows for maintenance of the anterior chamber.

The inventors have termed the unique method of the subject invention interventional Valve Enhancing Trabeculotomy or "iVent". The iVent makes a precise cleavage in the anterior aspect of the trabecular meshwork. Care is taken to avoid the intracanalicular structures and valves when creating this cleavage plane. By specifically cleaving the anterior trabecular meshwork a vent is created.

In regard to traction, by just incising the trabecular meshwork, the anterior attachment is released, and the posterior aspect of the trabecular meshwork shifts away from the anterior insertion into the corneal/scleral inner wall. The movement of the anterior trabecular meshwork from its insertion site allows for traction on the intracanalicular structures and enhancement of canalicular valve function. By enhancing the pump/valve mechanism, the IOP is lowered through improvement of the traditional outflow pathway. This mechanism of enhancement is specifically unique to iVent.

The iVent is different from other anterior segment angle surgeries as it spares disruption of the intracanalicular structures. The enhancement of the traditional outflow pathway may be considered similar to the enhancement seen after such procedures like selective laser trabeculoplasty or SLT, which also has the potential to enhance or rejuvenate an eye's outflow pathway. The cellular stimulation created by the iVent will also improve the pump mechanism of the intracanalicular valves. Additionally, because the trabecular meshwork is being cleaved and not incised and cored out (as is other type of angle surgeries) the iVent is less disruptive and results in a lower degree of acute intraocular inflammation. A significant population of unique cells with stem cell properties reside at Schwalbe's line as shown by (1) Raviola, G. Schwalbe's line's cells: a new cell type in the trabecular meshwork of *Macaca mulatta*. Invest Ophthalmol Vis Sci.m1982: 22:45-56 and (2) Braunger B M, Ademoglu B, Koschade S E, at al., Identification of adult stem cells in Schwalbe's line region of the primate eye. IOVS 2014; 55:7499-7507, which are both incorporated herein by reference in their entireties. These adult stem cells, known as Schwalbe's line cells, may compensate for the loss of trabecular meshwork cells associated with glaucoma. These cells may be directly stimulated by iVent to provide a population of pluripotent stem cells that are capable of differentiating into outflow cells that enhance the physiology of outflow. Cytokine release and other factors related to favorable wound healing from the iVent procedure likely stimulate these stem cells to provide a population of cells to improve outflow.

Importantly, the iVent does not involve implanting a foreign body and as such, there is no concern of displacement of a stent or object. There is no concern of erosion or malfunction with the present invention as with an implant. Given the lack of an implant and the minimally traumatic nature of this technique, the iVent is minimally traumatic to the corneal endothelial cells.

It is presently believed that iVent has a lower risk of abnormal wound healing as a result of being less destructive to the trabecular meshwork, as compared to the other prior art techniques mentioned above. The iVent further does not remove valve and channels of the trabecular meshwork, nor does it obstruct or close down such channels.

The iVENT surgery has been found by the inventors to lower the intraocular pressure to the low teens when the patient is on one, or on no medications (i.e., medicated drops). The outcomes the inventors are seeing with IVENT appear to be distinctly different from the outcomes we have seen with KDB, Trabectome, OMNI, hydrus and istent or other angle based surgeries. These prior art mentioned surgeries tend to have a more modest IOP lowering that results in a postoperative IOP in the mid-teen range with the patient on 1-2 medications. The fact that the inventors are seeing significantly lower eye pressures following the iVENT surgery speaks to the novel and unique nature of this surgery and how it specifically enhances the patient's natural outflow pathway through improving the function of the intracanalicular pump/valve mechanism.

It will be understood that the instruments disclosed herein may be formed in a variety of sizes for small incision glaucoma surgery or regular glaucoma surgery.

In one presently preferred method of use of the instrument 40 may be configured for use in incising the nasal angle or temporal angle of the right eye and/or the left eye. The instrument 40 may be inserted through an incision in the cornea of the operative eye. An arc of the trabecular meshwork at (or minimally posterior of) to Schwalbe's line is then engaged by the cutting means of the instrument to create the unique cleavage plane. The trabecular meshwork drops in the posterior direction toward the iris. A gonioprism may be used to view the trabecular meshwork as it is engaged by the instrument 40. Irrigation fluid can optionally be applied on-demand by the user of the instrument 40 in a reflux burst or jet pulse.

Cutting of the anterior trabecular meshwork is achieved by incising just below or at Schwalbe's line. Based on the specific clinical case, the surgeon may selectively incise 1-5 clock hours. Additionally, the surgeon may choose to incise one area, leave an island of untreated trabecular meshwork, and incise a subsequent area, to maximize canal opening but minimize tissue disruption. This technique creates a unique anterior cleavage plane with the advantages of allowing the trabecular shelf or tissue to remain open and minimize disruption of microscopic structures within the canal. In fact, one could make a small corneal incision in the nasal quadrant and treat the temporal angle 180 degrees, thus creating a 360 degree iVent.

The design of the instrument of the present invention precisely allows for alignment to Schwalbe's line without any difficult positional maneuver for making the incision up to the 6 clock hours (when seating temporal to the patient). This is done easily with the left & right symmetrically designed instruments. If the surgeon were to sit on the opposite side, they could potentially have access to the lateral 6 clock hours and in theory treat 360 degrees if desired, although this approach is not the primary intent of this instrument however the inventors have taken this approach in certain situations.

The inventors believe that the concept that the eye outflow system is a passive filter is outdated. Indeed, Dr. Jorge A. Alvarado found that severe alterations occur in the cellular component and in the entire trabecular meshwork during primary open-angle glaucoma and ageing. The same author demonstrates that trabecular meshwork endothelial cells regulate aqueous outflow by actively releasing enzymes and cytokines that, upon binding to Schlemm's canal endothelial cells, increase transendothelial flow thereby facilitating the egress of aqueous humour. Trabecular meshwork endothelial cells secrete these factors in response to stimuli such as mechanical stretching, laser irradiation, and pro-inflammatory cytokines.

The inventors of the present invention believe that the instruments and methods of the present invention could be very effective with potential longer lasting results.

It is believed that incising the trabecular meshwork just posterior to the location of Schwalbe's line allows for the creation of a unique trabecular flap, unlike any other created by the prior art instruments. This flap is hinged posteriorly at the scleral spur, however, the angle of opening for the flap below Schwalbe's is intended to preserve and possibly enhance the intracanalicular structures (i.e., valves, tubules, etc.). These structures are disrupted when a suture, filament or catheter of the prior art techniques are threaded through Schlemm's canal or when a trabecular shelf is parallel to the iris. However, when a specifically designed spatula that is angled, beveled, and curved is used to create a selective and precise anterior incision in the trabecular meshwork, these intracanalicular structures are preserved and protected. In fact, there is a very high chance that the trabecular meshwork flap being released at its most anterior insertion will provide some tension or stretch on the intra-canalicular valves, a valvulotasis termed by the inventors, and potentially enhance their function.

Referring now to FIGS. 7-12, another embodiment of an instrument of the present invention is illustrated and designated as 40A. The numbered features of the instrument 40A are designated generally with the suffix letter "A" and are analogous to features of the aforementioned illustrated embodiment of the instrument 40 that share the same number (without the suffix letter "A"). The instrument 40A operates in an identical manner as described in detail above and has the same basic features of a hand grip 44A with a tip 52A including a base portion 54A that extends from the distal end 48A of the hand grip 44A and defines a base portion axis 56A through its geometric center. The base portion axis 56A is substantially parallel to, and coincident with, the central axis 50A of the hand grip 44A. The tip 52A further includes an intermediate portion 58A extending from the base portion 54A along an intermediate portion axis 60A that is transverse or angled relative to the base portion axis 56A. Preferably, the intermediate portion axis 60A is angled between about 130 degrees and 160 degrees relative to the base portion axis 56A, and more preferably angled about 145 degrees. It is further contemplated that this embodiment may be configured as a non-angled, straight instrument.

The tip 52A includes a terminal portion 64A extending from the intermediate portion 58A along a terminal portion axis 66A that is transverse to the intermediate portion axis 56A. Preferably, the terminal portion axis 66A is angled between about 90 degrees and about 140 degrees relative to the intermediate portion axis 60A, and more preferably is angled about 120 degrees. The terminal portion 64A includes cutting means for creating a remaining trabecular leaflet at, or just posterior of, Schwalbe's line in an eye.

The embodiment of the instrument 40A differs from the above-discussed first embodiment of the instrument 40 in that the terminal portion 64A is configured as a left-angled instrument relative to the hand grip 44A and the other portions of the tip 52A.

Figure 12B:
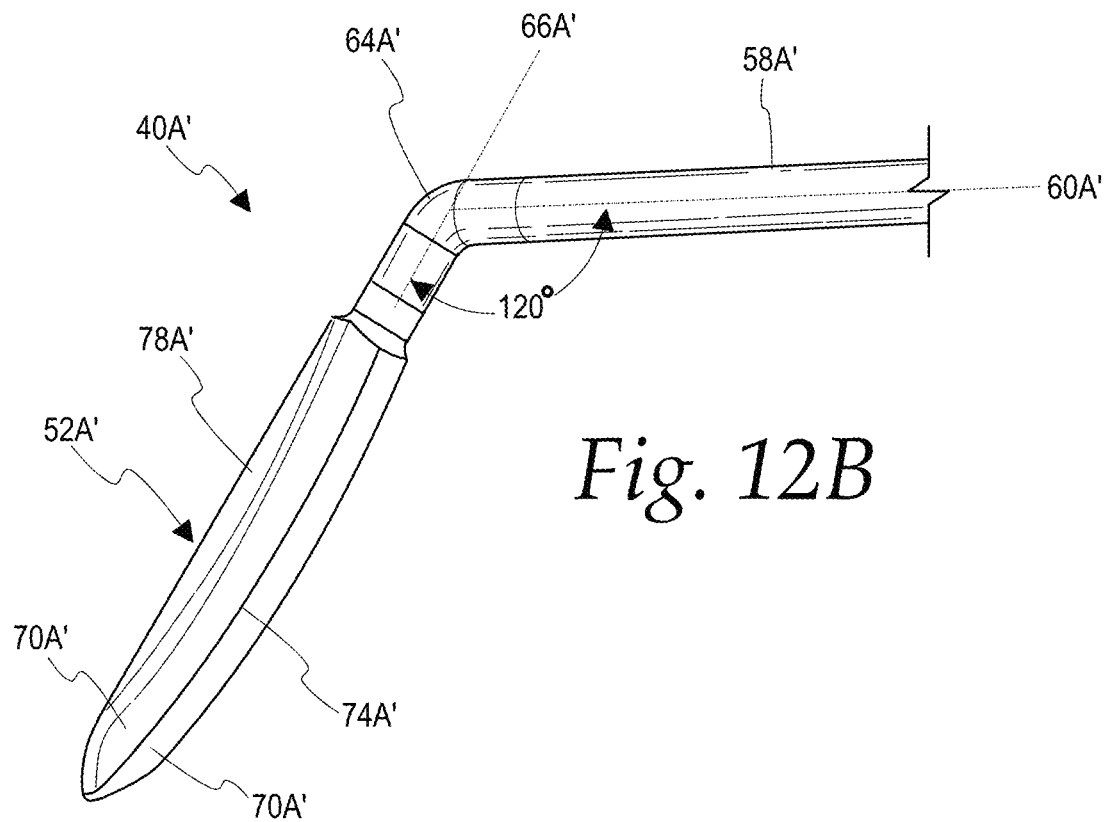
FIG. 12B is a greatly enlarged, isometric view from above, of the distal portion of the instrument shown in FIG. 12A.

Referring now to FIGS. 12A and 12B, a variation of the second illustrated embodiment of an instrument of the present invention is illustrated and designated as 40A'. The numbered features of the instrument 40A' are designated generally with the suffix "A" and are analogous to features of the aforementioned illustrated embodiment of the instrument 40A that share the same number (without the suffix letter "A'"). The instrument 40A' operates in an identical manner as described in detail above and has the same basic features of a hand grip with a tip including a base portion that extends from the distal end of the hand grip and defines a base portion axis through its geometric center. The base portion axis is substantially parallel to, and coincident with, the central axis of the hand grip. The tip further includes an intermediate portion 58A' extending from the base portion along an intermediate portion axis 60A' that is transverse or angled relative to the base portion axis. Preferably, the intermediate portion axis 60A' is angled between about 130 degrees and about 160 degrees relative to the base portion axis, and more preferably angled about 145 degrees.

The tip 52A' includes a terminal portion 64A' extending from the intermediate portion 58A' along a terminal portion axis 66A' that is transverse to the intermediate portion axis 56A'. The terminal portion 64A' includes cutting means for creating a remaining trabecular leaflet at, or just posterior of, Schwalbe's line in an eye.

The embodiment of the instrument 40A' differs from the above-discussed second embodiment of the instrument 40A in that the terminal portion axis 66A' is angled about 120 degrees to the intermediate portion axis 60A'. The inventors have found that increasing this angle greatly enhances the ability of a variety of users to create the aforementioned leaflet in a left-angled instrument (as illustrated), a right-angled instrument (e.g., as shown with embodiment of the instrument 40 in FIGS. 1-6), or a straight, non-angled instrument where the distal portion of the instrument extends in a plane containing the central axis of the hand grip.

The arcuate cutting edge 74A' is angled about between about 30 degrees and about 50 degrees out of the plane containing the axes 60A' and 66A', and more preferably about 40 degrees out of said plane.

With reference now to FIGS. 14-16 and 17-18, additional embodiments of an instrument of the present invention are illustrated and designated as 40B (left angled instrument) and 40C (right angled instrument), respectively. It is further contemplated that these embodiments may be configured as a non-angled, straight instrument. The numbered features of the instruments 40B and 40C are designated generally with the suffix letter "B" or "C" and are analogous to features of the aforementioned illustrated embodiment of the instrument 40 that share the same number (without the suffix letter "B" or "C"). The instruments 40B, 40C operate in an identical manner as described in detail above and has the same basic features of a hand grip 44B, 44C with a tip 52B, 52C including a base portion 54B, 54C that extends from the distal end 48B, 48C of the hand grip 44B, 44C and that defines a base portion axis 56B, 56C through its geometric center. The base portion axis 56B, 56C is substantially parallel to, and coincident with, the central axis 50B, 50C of the hand grip 44B, 44C. The tip 52B, 52C further includes an intermediate portion 58B, 58C extending from the base portion 54B, 54C along an intermediate portion axis 60B, 60C that is transverse or angled relative to the base portion axis 56B, 56C. Preferably, the intermediate portion axis 60B, 60C is angled between about 130 degrees and 160 degrees relative to the base portion axis 56B, 56C, and more preferably angled about 145 degrees.

The tip 52B, 52C includes a terminal portion 64B, 64C extending from the intermediate portion 58B, 58C along a terminal portion axis 66B, 66C that is transverse to the intermediate portion axis 56B, 56C. Preferably, the terminal portion axis 66B, 66C is angled between about 90 degrees and about 140 degrees relative to the intermediate portion axis 60B, 60C, and more preferably is angled about 120 degrees. The terminal portion 64B, 64C includes cutting means for creating a trabecular leaflet at, or just posterior of, Schwalbe's line in an eye.

The embodiments of the instrument 40B, 40C differ from the above-discussed first embodiment of the instrument 40 in that the terminal portion 64B, 64C is configured with an oval-shaped sloping face 70B, 70C that is angled about 45 degrees relative to the axis 66B, 66C, and that faces rearwardly toward the handle 44B, 44C when the instrument 40B, 40C is gripped by a user. The sloping face 70B, 70C defines a blunted, rounded distal edge 74B, 74C.

With reference now to FIGS. 19-22 and 23-25, additional embodiments of an instrument of the present invention are illustrated and designated as 40D (left angled instrument) and 40E (right angled instrument), respectively. It is further contemplated that these embodiments may be configured as a non-angled, straight instrument. The numbered features of the instruments 40D and 40E are designated generally with the suffix letter "D" or "E" and are analogous to features of the aforementioned illustrated embodiment of the instrument 40 that share the same number (without the suffix letter "D" or "E"). The instruments 40D, 40E operate in an identical manner as described in detail above and has the same basic features of a hand grip 44D, 44E with a tip 52D, 52E including a base portion 54D, 54E that extends from the distal end 48D, 48E of the hand grip 44D, 44E and that defines a base portion axis 56D, 56E through its geometric center. The base portion axis 56D, 56E is substantially parallel to, and coincident with, the central axis 50D, 50E of the hand grip 44D, 44E. The tip 52D, 52E further includes an intermediate portion 58D, 58E extending from the base portion 54D, 54E along an intermediate portion axis 60D, 60E that is transverse or angled relative to the base portion axis 56D, 56E. Preferably, the intermediate portion axis 60D, 60E is angled between about 130 degrees and 160 degrees relative to the base portion axis 56D, 56E, and more preferably angled about 145 degrees.

The tip 52D, 52E includes a terminal portion 64D, 64E extending from the intermediate portion 58D, 58E along a terminal portion axis 66D, 66E that is transverse to the intermediate portion axis 56D, 56E. Preferably, the terminal portion axis 66D, 66E is angled between about 90 degrees and about 140 degrees relative to the intermediate portion axis 60D, 60E, and more preferably is angled about 120 degrees. The terminal portion 64DB, 64E includes cutting means for creating a trabecular leaflet at, or just posterior of, Schwalbe's line in an eye.

Importantly, the embodiments of the instrument 40D, 40E differ from the above-discussed first embodiment of the instrument 40 in that the terminal portion 64D, 64E is configured with a tapering configuration defining a pair of opposite, trapezoidal faces 70D, 70E and a pair of opposite, triangular faces 71D, 71E which join and terminate in a blunted, rounded distal edge 74D, 74E that is angled about 45 degrees relative to the axis 66E, 66E. The edges between the faces 70D, 70E, 71D, 71E are sharpened to create the leaflet, while the edge 74D, 74E is blunted for enhanced safety.

With reference now to FIGS. 26-27 and 28-29, additional embodiments of an instrument of the present invention are illustrated and designated as 40F (right angled instrument) and 40G (left angled instrument), respectively. It is further contemplated that these embodiments may be configured as a non-angled, straight instrument. The numbered features of the instruments 40F and 40G are designated generally with the suffix letter "F" or "G" and are analogous to features of the aforementioned illustrated embodiment of the instrument 40 that share the same number (without the suffix letter "F" or "G"). The instruments 40F, 40G operate in an identical manner as described in detail above.

Importantly, the embodiments of the instrument 40F, 40G differ from the above-discussed first embodiment of the instrument 40 in that the terminal portion 64F, 64G is configured with a tapering, spatulated configuration defining a concave face 70F, 70G and a pair of opposite, concave edges 71F, 71G which join and terminate in a blunted, rounded distal edge 74F, 74G that is angled about 40 degrees relative to the axis 66F, 66G. The edges between the faces 70F, 70G, 71F, 71G are sharpened to create the leaflet, while the edge 74F, 74G is blunted for enhanced safety.

With reference now to FIGS. 30-31 and 32-33, additional embodiments of an instrument of the present invention are illustrated and designated as 40H (right angled instrument) and 40I (left angled instrument), respectively. The numbered features of the instruments 40H and 40I are designated generally with the suffix letter "H" or "I" and are analogous to features of the aforementioned illustrated embodiment of the instrument 40 that share the same number (without the suffix letter "H" or "I"). It is further contemplated that these embodiments may be configured as a non-angled, straight instrument. The instruments 40H, 40I operate in an identical manner as described in detail above with respect to the instrument 40. The embodiments of the instrument 40H, 40I differ from the above-discussed embodiments of the instruments 40B and 40C in that the terminal in that the terminal portion 64H, 64I is configured with a sloping face 70H, 70I that is angled about 30 degrees relative to the axis 66H, 66I.

With reference now to FIGS. 34-35 and 36-37, additional embodiments of an instrument of the present invention are illustrated and designated as 40J (right angled instrument) and 40K (left angled instrument), respectively. It is further contemplated that this embodiment may be configured as a non-angled, straight instrument. The numbered features of the instruments 40J and 40K are designated generally with the suffix letter "J" or "K" and are analogous to features of the aforementioned illustrated embodiment of the instrument 40 that share the same number (without the suffix letter "J" or "K"). The instruments 40J, 40K operate in an identical manner as described in detail above with respect to the instrument 40. The embodiments of the instrument 40J, 40K differ from the above-discussed embodiments of the instruments 40B and 40C in that the terminal in that the terminal portion 64J, 64K is configured with a sloping face 70J, 70K that is angled about 60 degrees relative to the axis 66J, 66K.

With reference now to FIGS. 38 and 39, additional embodiments of an instrument of the present invention are illustrated and designated as 40L (right angled instrument) and 40M (left angled instrument), respectively. The numbered features of the instruments 40L and 40M are designated generally with the suffix letter "L" or "M" and are analogous to features of the aforementioned illustrated embodiment of the instrument 40 that share the same number (without the suffix letter "L" or "M"). The instruments 40L, 40M operate in a similar manner as described in detail above with respect to the instrument 40.

Importantly, the embodiments of the instrument 40L, 40M differ from the above-discussed first embodiment of the instrument 40 in that the terminal portion 64L, 64M is configured with a tapering, conical face 70L, 70M which terminates in a pointed distal end 74L, 74M that is angled about 40 degrees relative to the axis 66L, 66M. The distal end 74L, 74M is sharpened to create the leaflet in the trabecular meshwork.

Figure 79:
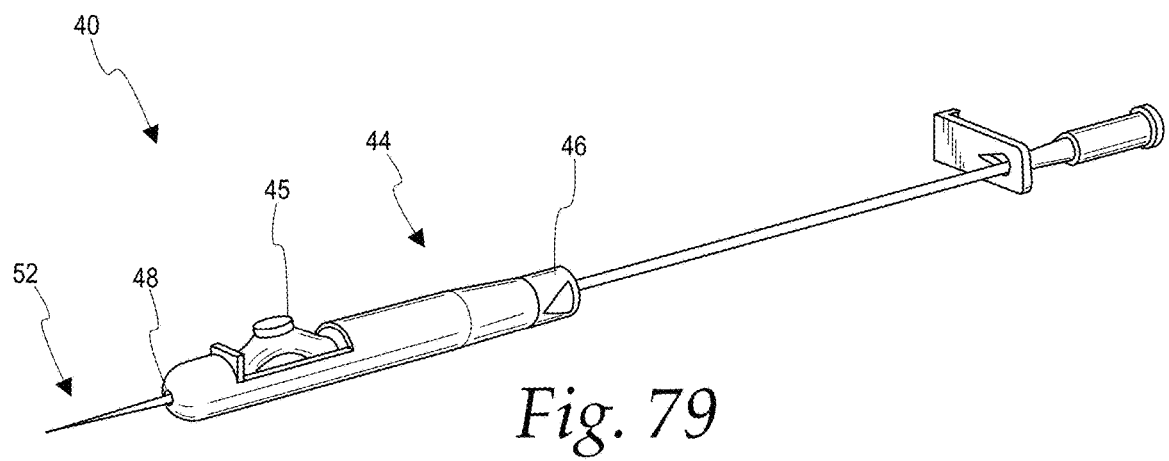
FIG. 79 is an isometric view from above of the first illustrated embodiment of the present invention coupled with an irrigation hand grip or handpiece.

Generally, the instruments illustrated and discussed herein may include one or more through passages communicating with an irrigation fluid supply source (either located in a reservoir in the hand grip, or located in an external pressurized container or machine and connected to the hand grip through tubing). With reference to FIG. 79, the hand grip 44 may include a pressure switch 45, bellows, or other means to facilitate the selective application of the irrigation fluid from the reservoir or irrigation fluid supply source to a target surgical site or location at the distal, operative end of the instrument proximate the cutting means. Such a hand grip with a reservoir and pressure switch is disclosed in International Application Publication no. WO/2023/018568 of Nallakrishnan, which is incorporated by reference herein in its entirety. Alternatively, an irrigation fluid may be supplied via a sleeve or tube situated around a portion of the instrument. There are many commercially available irrigating handpieces or systems on the market, and it will be understood that the instrument may be adapted to function with such handpieces or systems.

In another broad form of the invention, the embodiments of the instruments disclosed herein are capable of being attached or otherwise coupled with a movable hand grip portion in the form of a handpiece to assist in performing the surgical procedure. The handpiece may be, for example, a longitudinally vibrating phacoemulsification handpiece, a torsionally-vibrating phacoemulsification handpiece, an elliptically vibrating phacoemulsification handpiece, a phacoemulsification handpiece configured for vibratory movement in three dimensions, a vitrectomy handpiece, a piezo electric handpiece, an ultrasound handpiece, a solenoid valve handpiece, pneumatic, or a battery powered handpiece. Other vibratory handpieces may be used with the instruments disclosed herein.

The handpiece may be developed for the treatment of Open Angle Glaucoma, specifically at the Juxtacanalicular Space (JCS), but not limited to, or based on, combination treatments including vibrating, pulsating, oscillating, Guillotine, Piezo, Radiofrequency (RF), Neodymium-doped yttrium aluminum garnet (Nd:YAG) Laser platforms with specially designed tips and/or Laser probes. The handpiece may be a cautery or a cryo surgical handpiece.

The proximal end or portion of the instrument would not function as a hand grip, per se, when incorporated into a handpiece, and may be removably or non-removably coupled with the handpiece, such as by mating threads, luer lock, force fit, snap-fit, etc.

With reference now to FIGS. 40-43, an embodiment of a cannulated instrument of the present invention is illustrated and designated as 40N. While only the left-angled instrument 40N is illustrated, it will be understood that a mirror opposite, right-angled instrument 40N, and non-angled or straight instrument 40N, is contemplated. The numbered features of the instrument 40N are designated generally with the suffix letter "N" and are analogous to features of the aforementioned illustrated embodiment of the instruments 40B and 40C that share the same number (without the suffix letter "N"). The instrument 40N operates in a similar manner as described in detail above with respect to the instrument 40.

Importantly, the embodiment of the instrument 40N differs from the above-discussed instruments 40B and 40C in that the instrument 40N is configured with an internal passage 76N that terminates at an irrigation port 75N located in the sloping face 70N. The irrigation port 75N is configured to direct a flow of an irrigation fluid generally along the axis 66N.

With reference now to FIGS. 44 and 45, an additional embodiment of a cannulated instrument of the present invention is illustrated and designated as 40O. While only the left-angled instrument 40O is illustrated, it will be understood that a mirror opposite, right-angled instrument 40O, and non-angled or straight instrument 40O, is contemplated. The numbered features of the instrument 40O are designated generally with the suffix letter "O" and are analogous to features of the aforementioned illustrated embodiment of the instruments 40B and 40C that share the same number (without the suffix letter "O"). The instrument 40O operates in a similar manner as described in detail above with respect to the instrument 40.

Importantly, the embodiment of the instrument 40O differs from the above-discussed instruments 40B and 40C in that the instrument 40O is configured with an internal passage 76O that terminates at a pair of irrigation ports 75O located in the intermediate portion 58O and the terminal portion 64O. The irrigation ports 75O are configured to direct a first flow of an irrigation fluid generally along the axis 60O of the intermediate portion 58O and a second flow of an irrigation fluid in a direction that is orthogonal or normal to each of the axes 60O and 66O of the instrument 40O.

With reference now to FIGS. 46 and 47, an additional embodiment of a cannulated instrument of the present invention is illustrated and designated as 40P. While only the left-angled instrument 40P is illustrated, it will be understood that a mirror opposite, right-angled instrument 40P, and non-angled or straight instrument 40P, is contemplated. The numbered features of the instrument 40P are designated generally with the suffix letter "P" and are analogous to features of the aforementioned illustrated embodiment of the instruments 40B and 40C that share the same number (without the suffix letter "P"). The instrument 40P operates in a similar manner as described in detail above with respect to the instrument 40.

Importantly, the embodiment of the instrument 40P differs from the above-discussed instruments 40B and 40C in that the instrument 40P is configured with an internal passage 76P that terminates at a pair of oppositely-facing irrigation ports 75P located in the intermediate portion 58P. The irrigation ports 75P are configured to direct flows of an irrigation fluid generally along the axis 60P of the terminal portion 64P of the tip.

Figure 48:
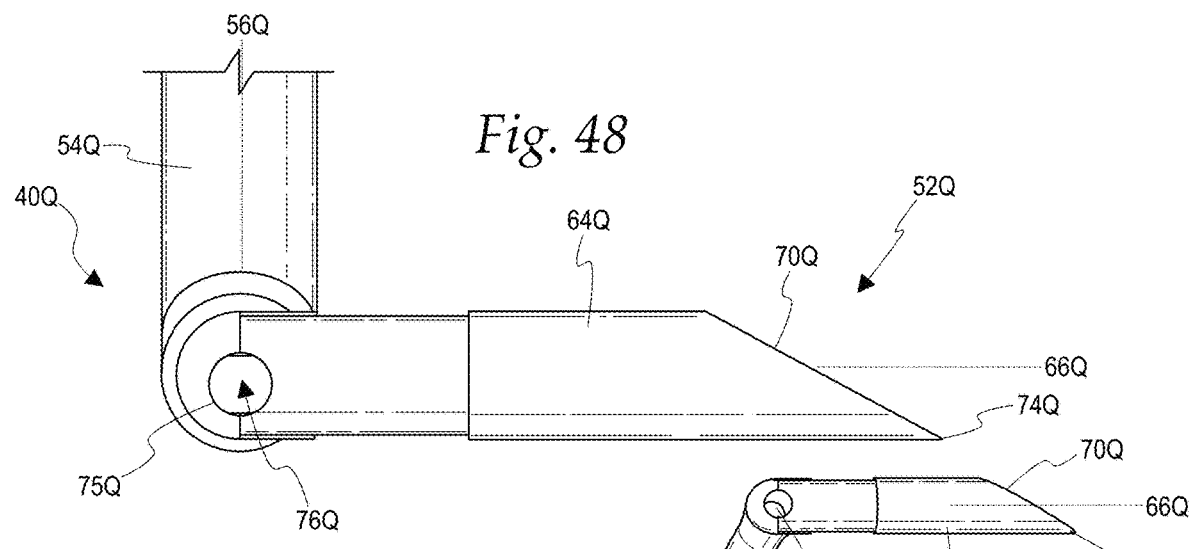
FIG. 48 is a fragmentary, rear elevation view of an eighteenth embodiment of a surgical instrument according to the present invention, wherein the instrument is configured as a left-angled instrument and only part of the tip portion is visible.
Figure 49:
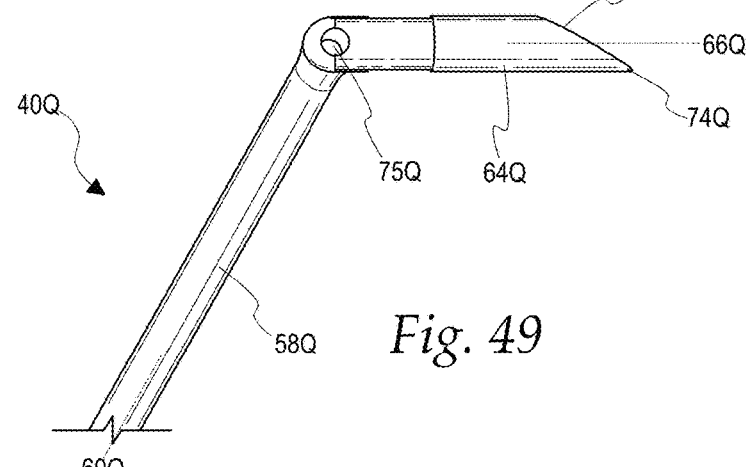
FIG. 49 is an isometric view from below of the instrument of FIG. 48.

Referring now to FIGS. 48 and 49, an additional embodiment of a cannulated instrument of the present invention is illustrated and designated as 40Q. While only the left-angled instrument 40Q is illustrated, it will be understood that a mirror opposite, right-angled instrument 40Q, and non-angled or straight instrument 40Q, is contemplated. The numbered features of the instrument 40Q are designated generally with the suffix letter "Q" and are analogous to features of the aforementioned illustrated embodiment of the instruments 40B and 40C that share the same number (without the suffix letter "Q"). The instrument 40Q operates in a similar manner as described in detail above with respect to the instrument 40.

Importantly, the embodiment of the instrument 40Q differs from the above-discussed instruments 40B and 40C in that the instrument 40Q is configured with an internal passage that terminates in a single irrigation port 75Q located in the bend between the intermediate portion 58Q and the terminal portion 64Q. The irrigation port 75Q is configured to direct a flow of an irrigation fluid generally along the axis 60Q of the tip.

Figure 50:
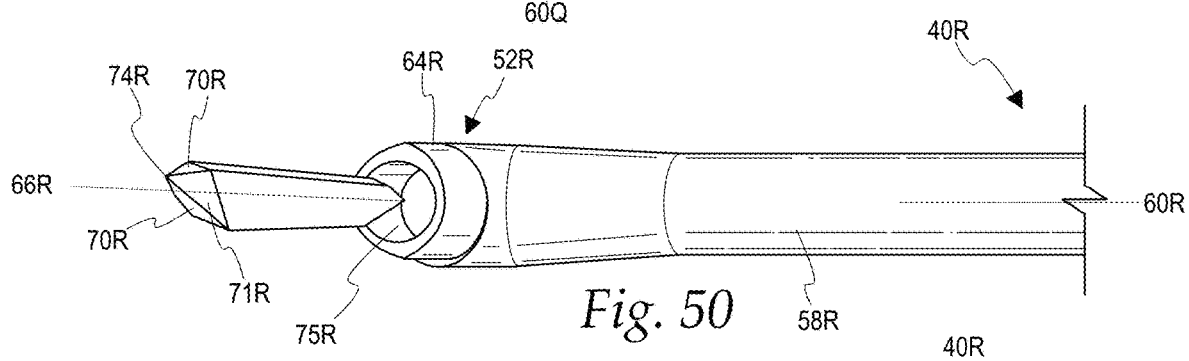
FIG. 50 is a fragmentary, isometric view from the left side of a nineteenth embodiment of a surgical instrument according to the present invention, wherein the instrument is configured as a left-angled instrument and only part of the tip portion is visible.
Figure 51:
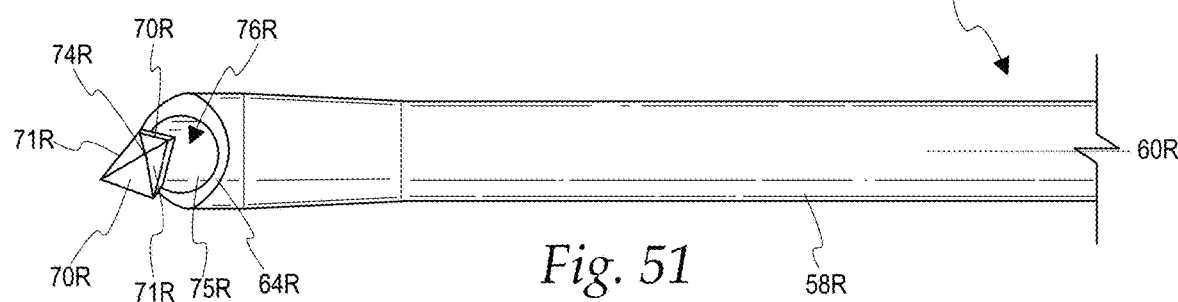
FIG. 51 is a fragmentary, left side elevation view of the instrument of FIG. 50.

Referring now to FIGS. 50 and 51, an embodiment of a cannulated instrument of the present invention is illustrated and designated as 40R. While only the left-angled instrument 40R is illustrated, it will be understood that a mirror opposite, right-angled instrument 40R, and non-angled or straight instrument 40R, is contemplated. The numbered features of the instrument 40R are designated generally with the suffix letter "R" and are analogous to features of the aforementioned illustrated embodiment of the instruments 40D and 40E that share the same number (without the suffix letter "R"). The instrument 40R operates in a similar manner as described in detail above with respect to the instrument 40.

Importantly, the embodiment of the instrument 40R differs from the above-discussed instruments 40D and 40E in that the instrument 40R is configured with an internal passage that terminates in a single irrigation port 75R located in the terminal portion 64R adjacent the cutting means. The irrigation port 75R is configured to direct a flow of an irrigation fluid generally along the axis 66R of the terminal portion 64R.

Figure 52:
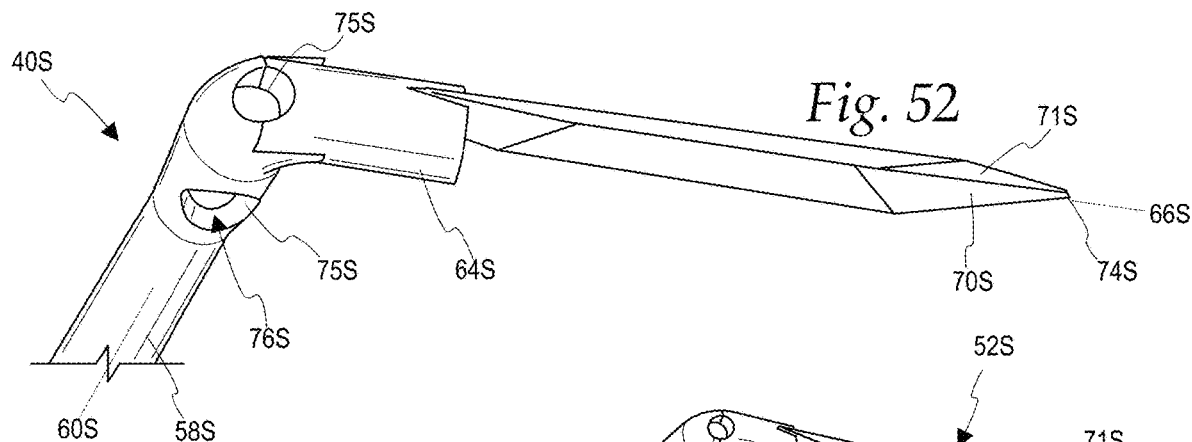
FIG. 52 is a fragmentary, isometric view from below of a twentieth embodiment of a surgical instrument according to the present invention, wherein the instrument is configured as a left-angled instrument and only part of the tip portion is visible.
Figure 53:
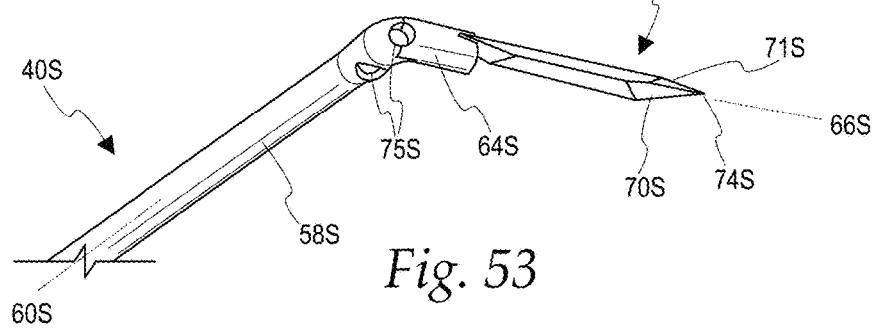
FIG. 53 is another isometric view from below of the instrument of FIG. 52.

Referring now to FIGS. 52 and 53, an embodiment of a cannulated instrument of the present invention is illustrated and designated as 40S. While only the left-angled instrument 40S is illustrated, it will be understood that a mirror opposite, right-angled instrument 40S, and non-angled or straight instrument 40S, is contemplated. The numbered features of the instrument 40S are designated generally with the suffix letter "S" and are analogous to features of the aforementioned illustrated embodiment of the instruments 40D and 40E that share the same number (without the suffix letter "S"). The instrument 40ES operates in a similar manner as described in detail above with respect to the instrument 40.

Importantly, the embodiment of the instrument 40S differs from the above-discussed instruments 40D and 40E in that the instrument 40S is configured with an internal passage that terminates at a pair of irrigation ports 75S located in the intermediate portion 58S and the terminal portion 64S. The irrigation ports 75S are configured to direct a first flow of an irrigation fluid generally along the axis 60S of the intermediate portion 58S and a second flow of an irrigation fluid in a direction that is orthogonal or normal to each of the axes 60S and 66S of the instrument 40S.

Figure 54:
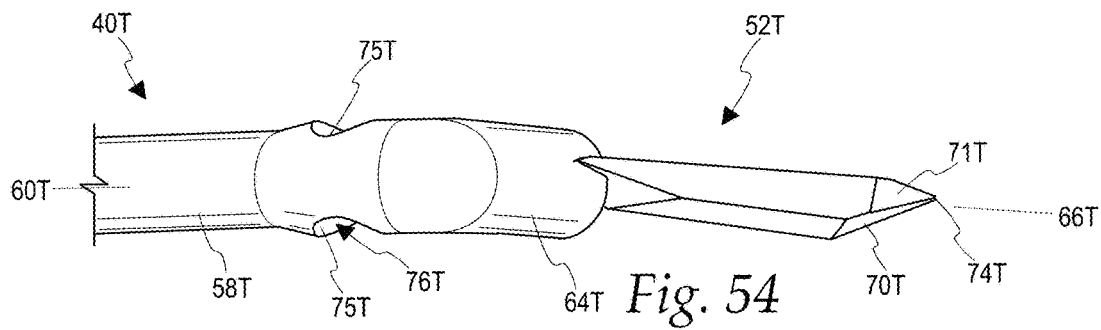
FIG. 54 is a fragmentary, isometric view from the right side of a twenty-first embodiment of a surgical instrument according to the present invention, wherein the instrument is configured as a left-angled instrument and only part of the tip portion is visible.
Figure 55:
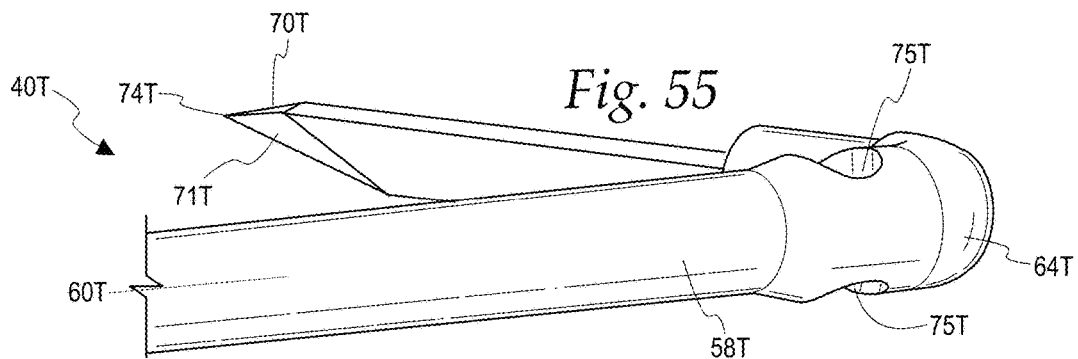
FIG. 55 is another isometric view from the right side of the instrument of FIG. 54.

Referring now to FIGS. 54 and 55, an embodiment of a cannulated instrument of the present invention is illustrated and designated as 40T. While only the left-angled instrument 40T is illustrated, it will be understood that a mirror opposite, right-angled instrument 40T, and non-angled or straight instrument 40T, is contemplated. The numbered features of the instrument 40T are designated generally with the suffix letter "T" and are analogous to features of the aforementioned illustrated embodiment of the instruments 40D and 40E that share the same number (without the suffix letter "T"). The instrument 40T operates in a similar manner as described in detail above with respect to the instrument 40.

Importantly, the embodiment of the instrument 40T differs from the above-discussed instruments 40D and 40E in that the instrument 40T is configured with an internal passage (not visible in FIGS. 54 and 55) that terminates at a pair of oppositely-facing irrigation ports 75T located in the intermediate portion 58T. The irrigation ports 75T are configured to direct flows of an irrigation fluid generally along an orthogonal direction relative to the axes 60T and 66T.

Figure 56:
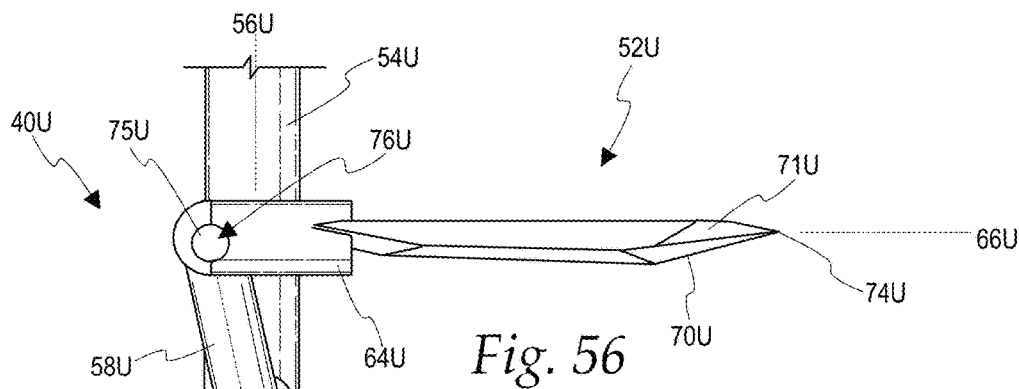
FIG. 56 is a fragmentary, isometric view from the rear of a twenty-second embodiment of a surgical instrument according to the present invention, wherein the instrument is configured as a left-angled instrument and only part of the tip portion is visible.
Figure 57:
FIG. 57 is another isometric view from the front of the instrument of FIG. 56.

Referring now to FIGS. 56 and 57, another embodiment of a cannulated instrument of the present invention is illustrated and designated as 40U. While only the left-angled instrument 40U is illustrated, it will be understood that a mirror opposite, right-angled instrument 40U, and non-angled or straight instrument 40U, is contemplated. The numbered features of the instrument 40U are designated generally with the suffix letter "U" and are analogous to features of the aforementioned illustrated embodiment of the instruments 40D and 40E that share the same number (without the suffix letter "U"). The instrument 40U operates in a similar manner as described in detail above with respect to the instrument 40.

Importantly, the embodiment of the instrument 40U differs from the above-discussed instruments 40D and 40E in that the instrument 40U is configured with an internal passage (not visible in FIGS. 56 and 55) that terminates at a single irrigation port 75U located in the bend between the terminal portion 64U and the intermediate portion 58U. The irrigation ports 75U are configured to direct flows of an irrigation fluid generally along the axis 60U of the intermediate portion 58U.

Figure 58:
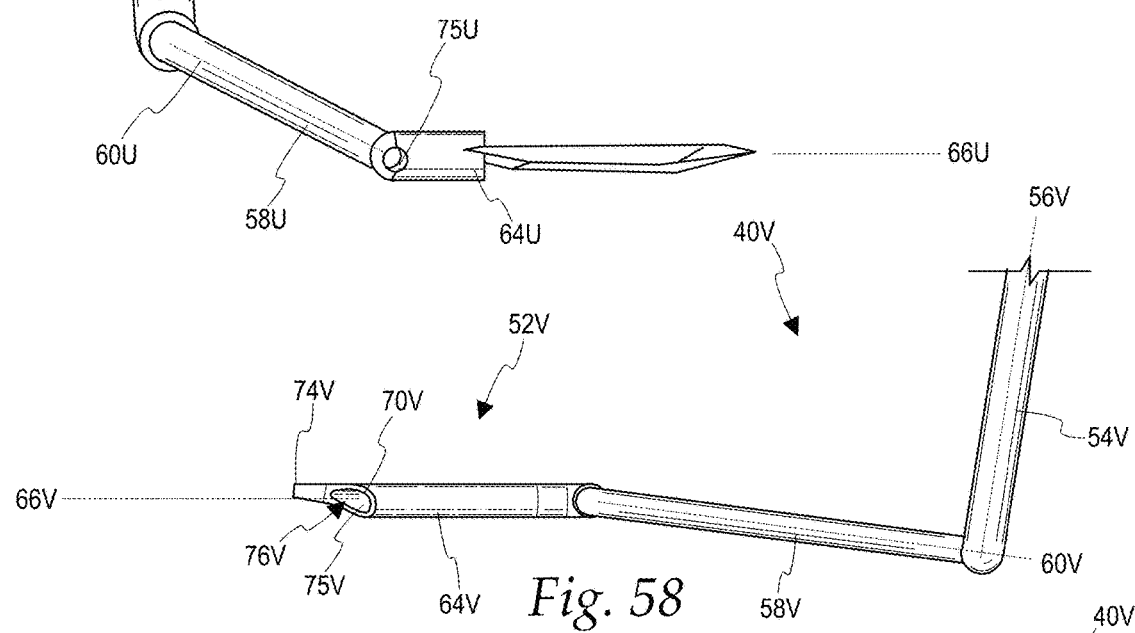
FIG. 58 is a fragmentary, isometric view from the rear of a twenty-third embodiment of a surgical instrument according to the present invention, wherein the instrument is configured as a left-angled instrument and only part of the tip portion is visible.
Figure 59:
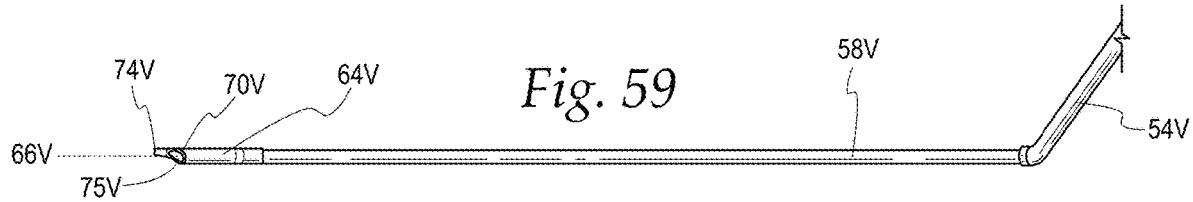
FIG. 59 is another isometric view from the left side of the instrument of FIG. 58.

Referring now to FIGS. 58 and 59, another embodiment of a cannulated instrument of the present invention is illustrated and designated as 40V. While only the left-angled instrument 40V is illustrated, it will be understood that a mirror opposite, right-angled instrument 40V, and non-angled or straight instrument 40V, is contemplated. The numbered features of the instrument 40V are designated generally with the suffix letter "V" and are analogous to features of the aforementioned illustrated embodiment of the instruments 40F and 40G that share the same number (without the suffix letter "V"). The instrument 40V operates in a similar manner as described in detail above with respect to the instrument 40.

The embodiment of the instrument 40V differs from the above-discussed instruments 40F and 40G in that the instrument 40V is configured with an internal passage (not visible in FIGS. 58 and 59) that terminates at a single irrigation port 75V located in the concave face 70V in the terminal portion 64V. The irrigation port 75V is configured to direct a flow of an irrigation fluid generally along the axis 66V of the terminal portion 64V.

Figure 60:
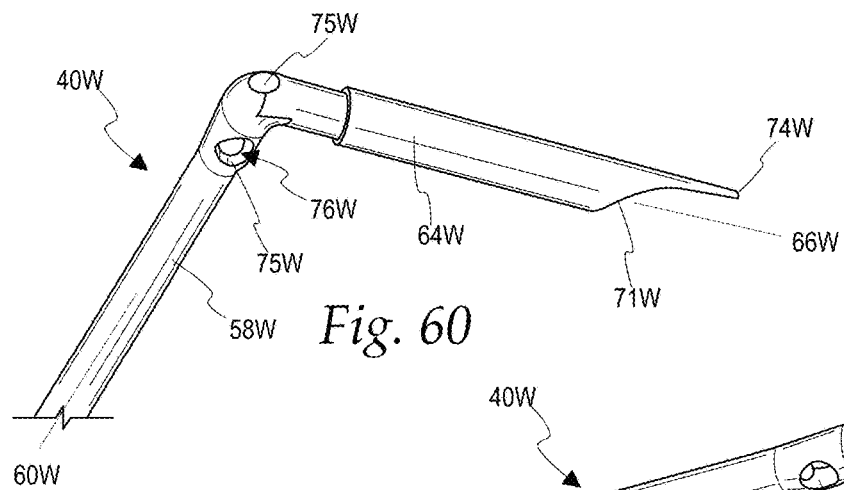
FIG. 60 is a fragmentary, isometric view from below of a twenty-fourth embodiment of a surgical instrument according to the present invention, wherein the instrument is configured as a left-angled instrument and only part of the tip portion is visible.
Figure 61:
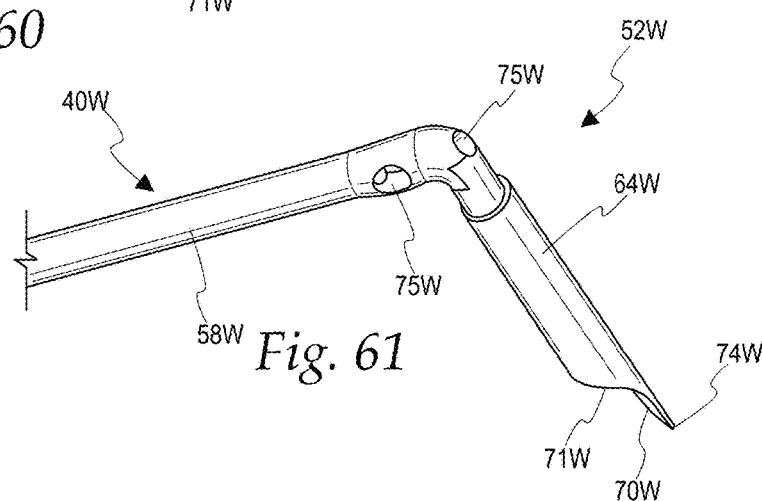
FIG. 61 is another isometric view from the right side of the instrument of FIG. 60.

Referring now to FIGS. 60 and 61, another embodiment of a cannulated instrument of the present invention is illustrated and designated as 40W. While only the left-angled instrument 40W is illustrated, it will be understood that a mirror opposite, right-angled instrument 40W, and non-angled or straight instrument 40W, is contemplated. The numbered features of the instrument 40W are designated generally with the suffix letter "W" and are analogous to features of the aforementioned illustrated embodiment of the instruments 40F and 40G that share the same number (without the suffix letter "W"). The instrument 40W operates in a similar manner as described in detail above with respect to the instrument 40.

The embodiment of the instrument 40W differs from the above-discussed instruments 40F and 40G in that the instrument 40W is configured with an internal passage (not visible in FIGS. 60 and 61) that terminates in a pair of irrigation ports 75W located in the intermediate portion 58W of the instrument tip. The irrigation ports 75W are configured to direct a first flow of an irrigation fluid generally along the axis 60W and a second flow of an irrigation fluid generally along a direction normal or orthogonal to each of the axes 66W and 60W.

Figure 62:
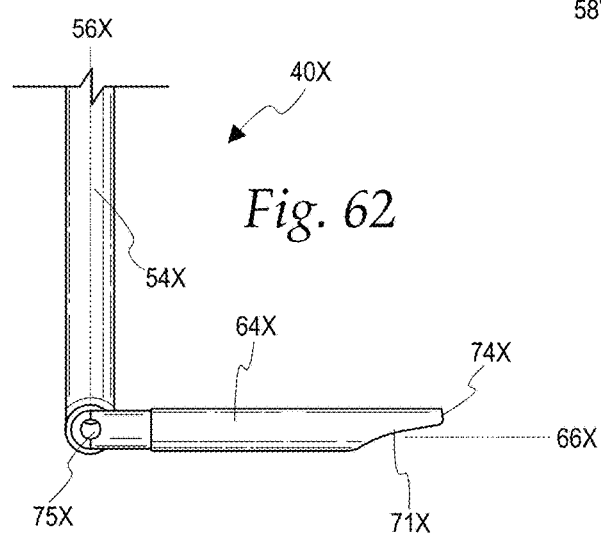
FIG. 62 is a fragmentary, rear elevation view of a twenty-fifth embodiment of a surgical instrument according to the present invention, wherein the instrument is configured as a left-angled instrument and only part of the tip portion is visible.
Figure 63:
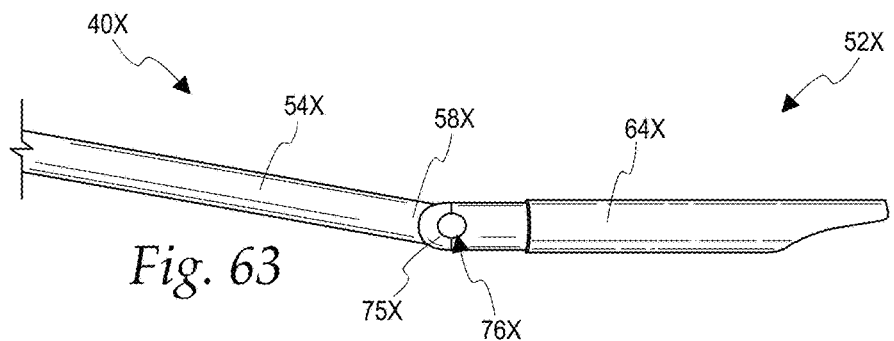
FIG. 63 is an isometric view from the right side of the instrument of FIG. 62.

Referring now to FIGS. 62 and 63, another embodiment of a cannulated instrument of the present invention is illustrated and designated as 40X. While only the left-angled instrument 40X is illustrated, it will be understood that a mirror opposite, right-angled instrument 40X, and non-angled or straight instrument 40X, is contemplated. The numbered features of the instrument 40X are designated generally with the suffix letter "X" and are analogous to features of the aforementioned illustrated embodiment of the instruments 40F and 40G that share the same number (without the suffix letter "X"). The instrument 40X operates in a similar manner as described in detail above with respect to the instrument 40.

The embodiment of the instrument 40X differs from the above-discussed instruments 40F and 40G in that the instrument 40X is configured with an internal passage (not visible in FIGS. 62 and 63) that terminates in a single irrigation port 75X located in the intermediate portion 58X of the instrument tip. The irrigation port 75X is configured to direct a flow of an irrigation fluid generally along the axis of the intermediate portion 58X.

Figure 64:
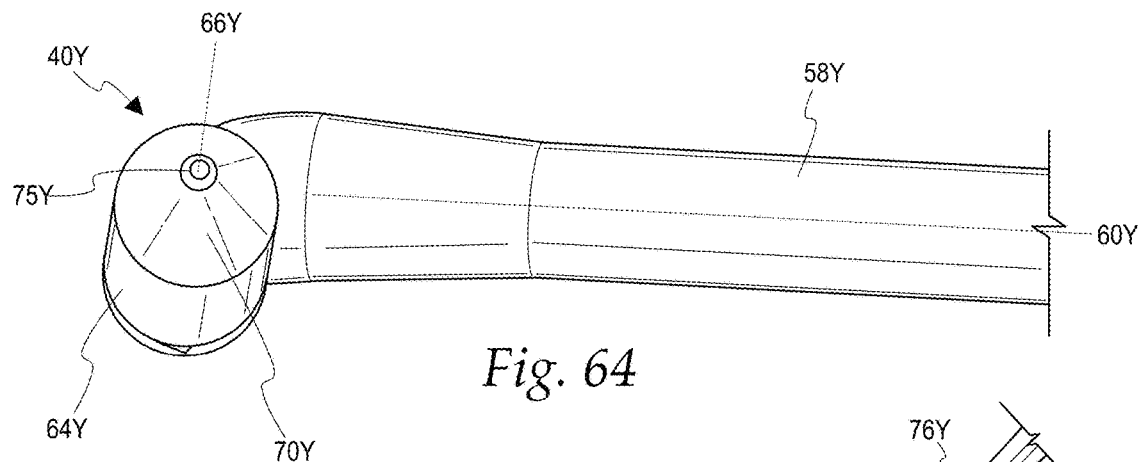
FIG. 64 is a fragmentary, isometric view of a twenty-sixth embodiment of a surgical instrument according to the present invention, wherein the instrument is configured as a left-angled instrument and only part of the tip portion is visible.
Figure 65:
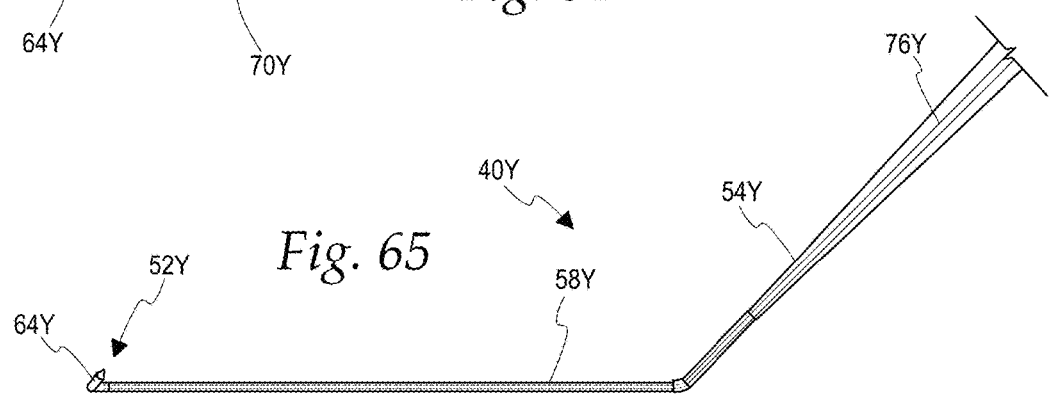
FIG. 65 is a left side elevation view of the instrument of FIG. 64.

Referring now to FIGS. 64 and 65, another embodiment of a cannulated instrument of the present invention is illustrated and designated as 40Y. While only the left-angled instrument 40Y is illustrated, it will be understood that a mirror opposite, right-angled instrument 40Y, and non-angled or straight instrument 40Y, is contemplated. The numbered features of the instrument 40Y are designated generally with the suffix letter "Y" and are analogous to features of the aforementioned illustrated embodiment of the instruments 40L and 40M that share the same number (without the suffix letter "Y"). The instrument 40Y operates in a similar manner as described in detail above with respect to the instrument 40.

The embodiment of the instrument 40Y differs from the above-discussed instruments 40L and 40M in that the instrument 40Y is configured with an internal passage 76Y that terminates in a single irrigation port 75Y located in the terminal portion 64Y of the instrument tip. The irrigation port 75Y is configured to direct a flow of an irrigation fluid generally along the axis 66Y of the terminal portion 64Y.

Figure 66:
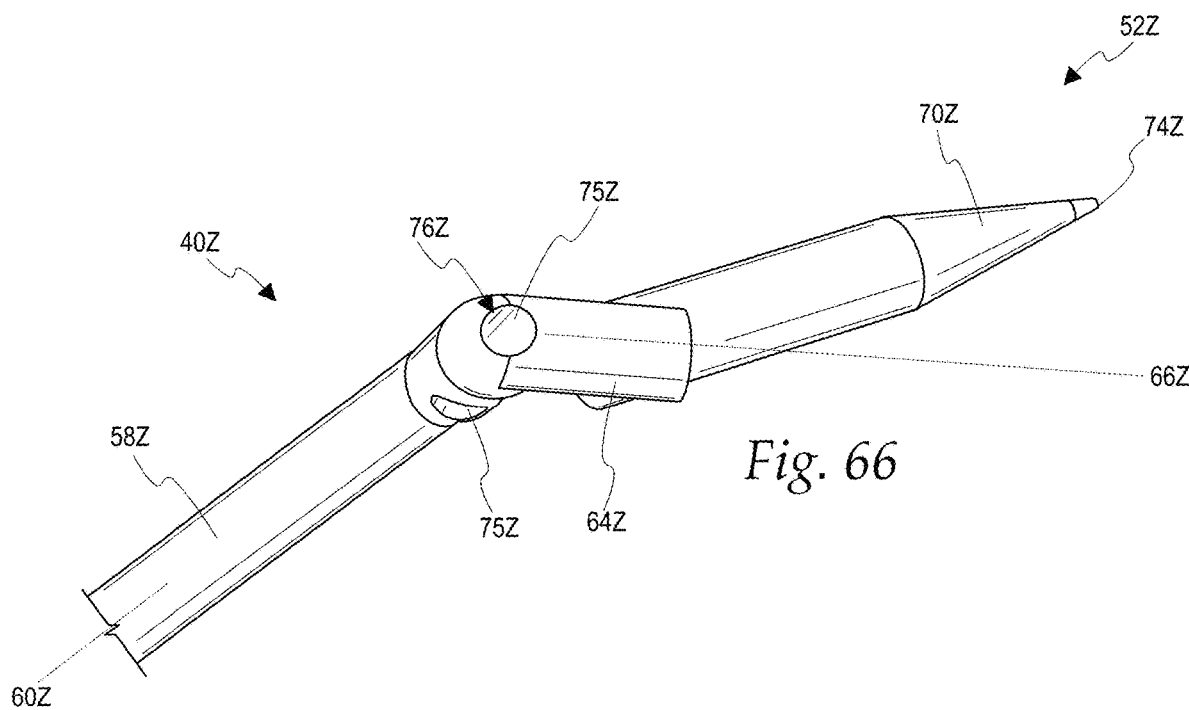
FIG. 66 is a fragmentary, isometric view from below of a twenty-seventh embodiment of a surgical instrument according to the present invention, wherein the instrument is configured as a left-angled instrument and only part of the tip portion is visible.

Referring now to FIG. 66, another embodiment of a cannulated instrument of the present invention is illustrated and designated as 40Z. While only the left-angled instrument 40Z is illustrated, it will be understood that a mirror opposite, right-angled instrument 40Z, and non-angled or straight instrument 40Z, is contemplated. The numbered features of the instrument 40Z are designated generally with the suffix letter "Z" and are analogous to features of the aforementioned illustrated embodiment of the instruments 40L and 40M that share the same number (without the suffix letter "Z"). The instrument 40Z operates in a similar manner as described in detail above with respect to the instrument 40.

The embodiment of the instrument 40Z differs from the above-discussed instruments 40L and 40M in that the instrument 40Z is configured with an internal passage (not visible in FIG. 66) that terminates in a pair of irrigation ports 75Z located in the intermediate portion 58Z of the instrument tip. The irrigation ports 75Z are configured to direct a first flow of an irrigation fluid generally along the axis 60Z of the intermediate portion 58Z and a second flow of fluid in an orthogonal direction relative to the axes 66Z and 60Z.

Figure 67:
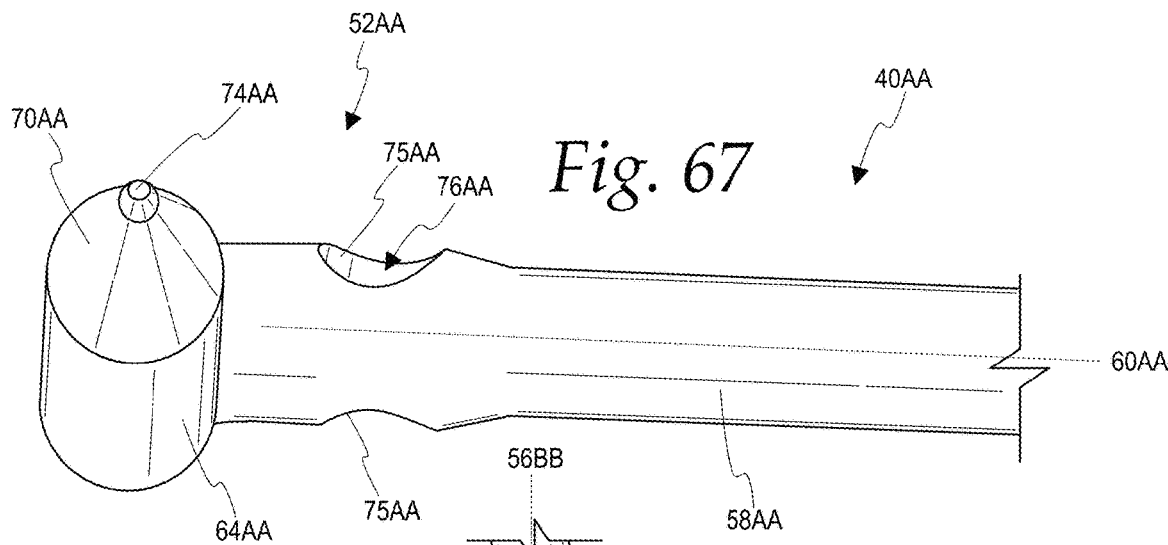
FIG. 67 is a fragmentary, isometric view of a twenty-eighth embodiment of a surgical instrument according to the present invention, wherein the instrument is configured as a left-angled instrument and only part of the tip portion is visible.

Referring now to FIG. 67, another embodiment of a cannulated instrument of the present invention is illustrated and designated as 40AA. While only the left-angled instrument 40AA is illustrated, it will be understood that a mirror opposite, right-angled instrument 40AA, and non-angled or straight instrument 40AA, is contemplated. The numbered features of the instrument 40AA are designated generally with the suffix letter "AA" and are analogous to features of the aforementioned illustrated embodiment of the instruments 40L and 40M that share the same number (without the suffix letter "AA"). The instrument 40AA operates in a similar manner as described in detail above with respect to the instrument 40.

The embodiment of the instrument 40AA differs from the above-discussed instruments 40L and 40M in that the instrument 40AA is configured with an internal passage (not visible in FIG. 67) that terminates in a pair of oppositely-facing irrigation ports 75AA located in the intermediate portion 58AA of the instrument tip. The irrigation ports 75AA are configured to direct opposite flows of an irrigation fluid generally in an orthogonal direction relative to the axis 60AA.

Figure 68:
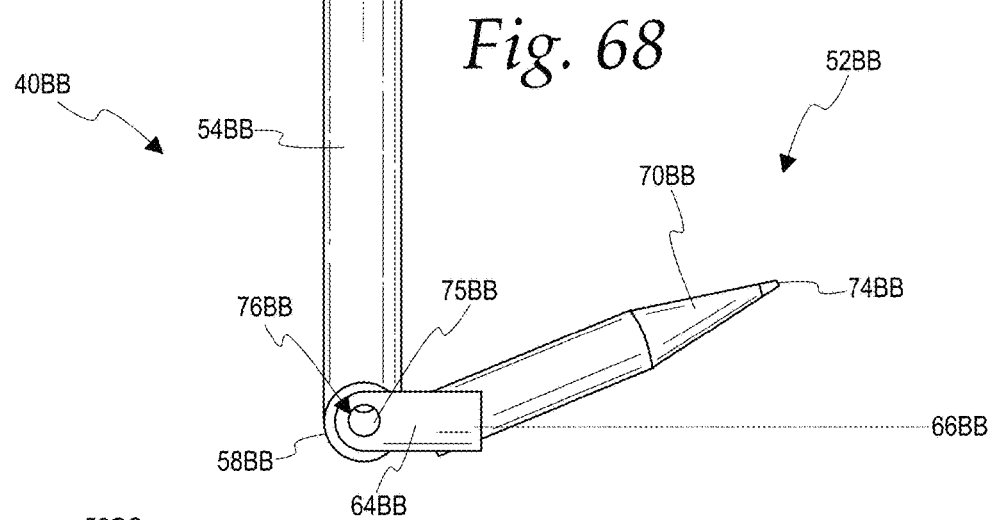
FIG. 68 is a fragmentary, rear elevation view of a twenty-ninth embodiment of a surgical instrument according to the present invention, wherein the instrument is configured as a left-angled instrument and only part of the tip portion is visible.

Referring now to FIG. 68, another embodiment of a cannulated instrument of the present invention is illustrated and designated as 40BB. While only the left-angled instrument 40BB is illustrated, it will be understood that a mirror opposite, right-angled instrument 40BB, and non-angled or straight instrument 40BB, is contemplated. The numbered features of the instrument 40BB are designated generally with the suffix letter "BB" and are analogous to features of the aforementioned illustrated embodiment of the instruments 40L and 40M that share the same number (without the suffix letter "BB"). The instrument 40BB operates in a similar manner as described in detail above with respect to the instrument 40.

The embodiment of the instrument 40BB differs from the above-discussed instruments 40L and 40M in that the instrument 40BB is configured with an internal passage (not visible in FIG. 68) that terminates in a single irrigation port 75BB located in the intermediate portion 58BB of the instrument tip. The irrigation port 75BB is configured to direct a flow of an irrigation fluid generally along the axis defined by the intermediate portion.

Figure 69:
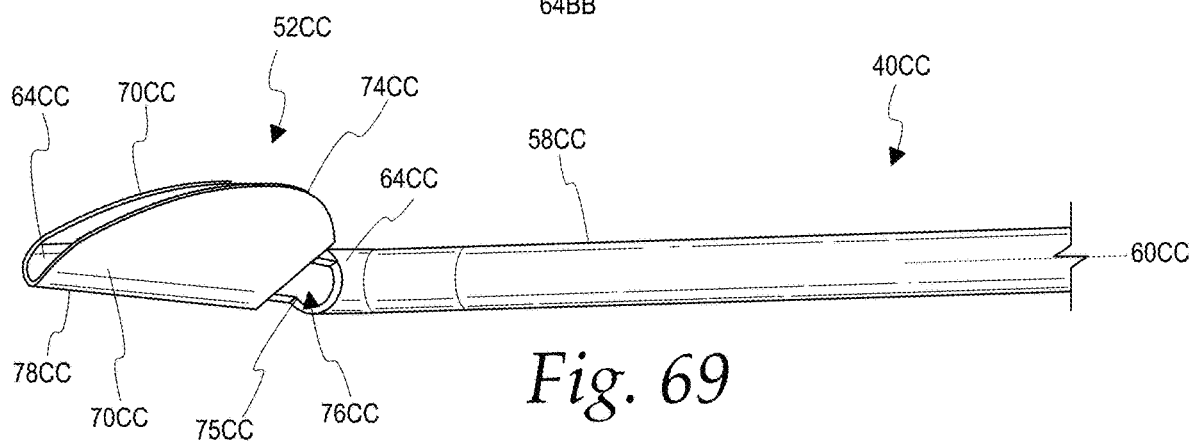
FIG. 69 is a greatly enlarged, fragmentary, isometric view of a thirtieth embodiment of a surgical instrument according to the present invention, wherein the instrument is configured as a left-angled instrument and only part of the tip portion is visible.
Figure 70:
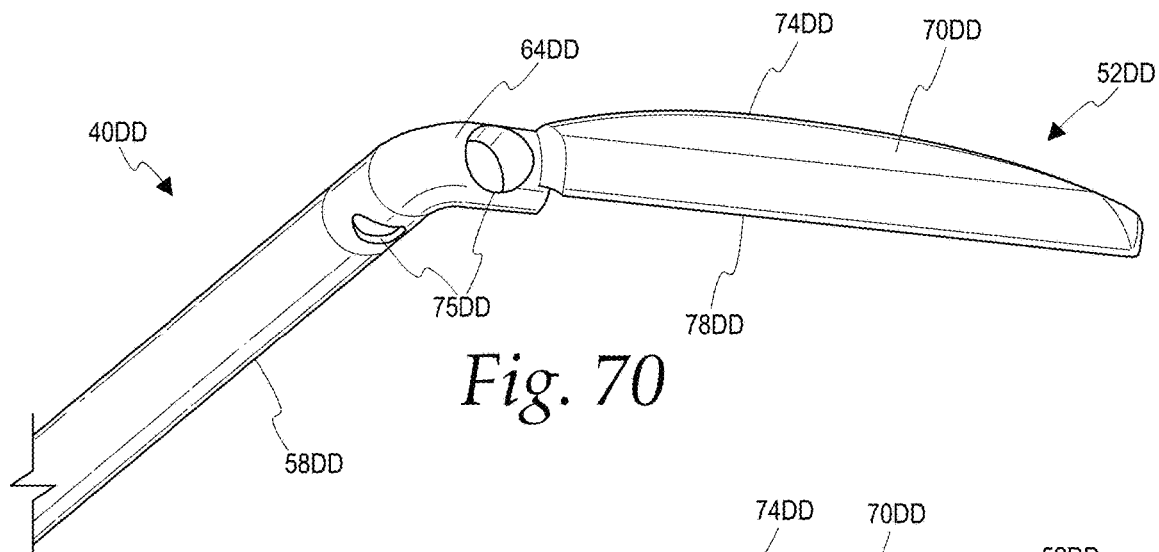
FIG. 70 is a greatly enlarged, fragmentary, isometric view of a thirty-first embodiment of a surgical instrument according to the present invention, wherein the instrument is configured as a left-angled instrument and only part of the tip portion is visible.
Figure 71:
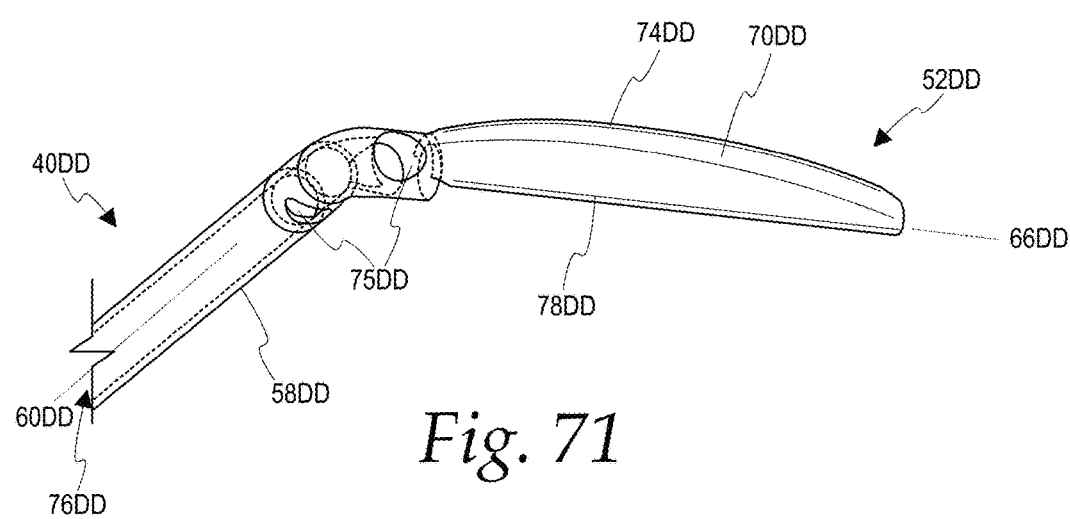
FIG. 71 is a greatly enlarged, fragmentary, isometric view of the instrument of FIG. 70.
Figure 72:
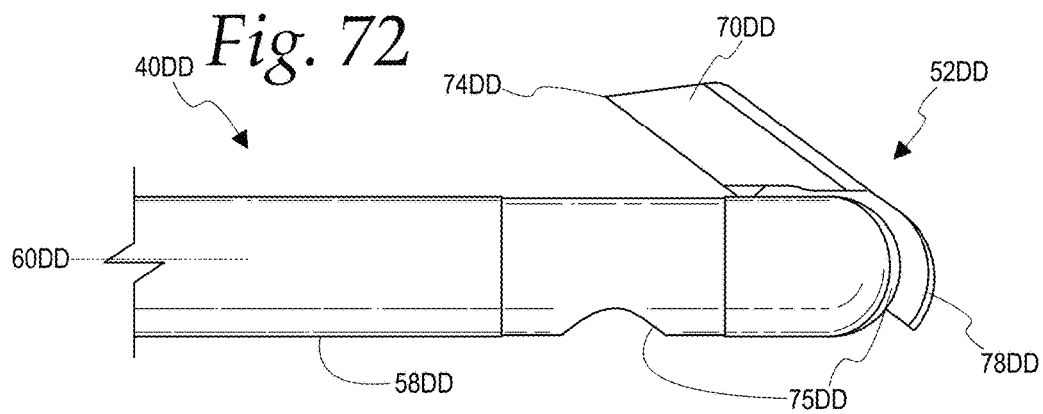
FIG. 72 is a greatly enlarged, fragmentary, right elevation view of the instrument of FIG. 70.

Referring now to FIG. 69, another embodiment of a cannulated instrument of the present invention is illustrated and designated as 40CC. While only the left-angled instrument 40CC is illustrated, it will be understood that a mirror opposite, right-angled instrument 40CC, and non-angled or straight instrument 40CC, is contemplated. The numbered features of the instrument 40CC are designated generally with the suffix letter "CC" and are analogous to features of the aforementioned illustrated embodiment of the instrument 40A that shares the same number (without the suffix letter "CC"). The instrument 40CC operates in a similar manner as described in detail above with respect to the instrument 40A.

The embodiment of the instrument 40CC differs from the above-discussed instrument 40A in that the instrument 40CC is configured with an internal passage 76CC that terminates in a single irrigation port 75CC located in the terminal portion 64CC of the instrument tip 52CC. The irrigation port 75CC is configured to direct a flow of an irrigation fluid generally along the central axis defined by the terminal portion 64CC.

Referring now to FIGS. 70-73, another embodiment of a cannulated instrument of the present invention is illustrated and designated as 40DD. While only the left-angled instrument 40DD is illustrated, it will be understood that a mirror opposite, right-angled instrument 40DD, and non-angled or straight instrument 40DD, is contemplated. The numbered features of the instrument 40DD are designated generally with the suffix letter "DD" and are analogous to features of the aforementioned illustrated embodiment of the instrument 40A that shares the same number (without the suffix letter "DD"). The instrument 40DD operates in a similar manner as described in detail above with respect to the instrument 40A.

The embodiment of the instrument 40DD differs from the above-discussed instrument 40A in that the instrument 40DD is configured with an internal flow passage 76DD that terminates in a first irrigation port 75DD located in the terminal portion 64DD of the instrument tip 52DD and a second irrigation port 75DD located in the intermediate portion 58DD of the tip 52DD. The first irrigation port 75DD is configured to direct a flow of an irrigation fluid generally along the central axis 60DD defined by the intermediate portion 58DD, while the second irrigation port 75DD is configured to direct a flow of an irrigation fluid generally orthogonal to each of the central axes 60DD and 66DD downward.

Figure 76:
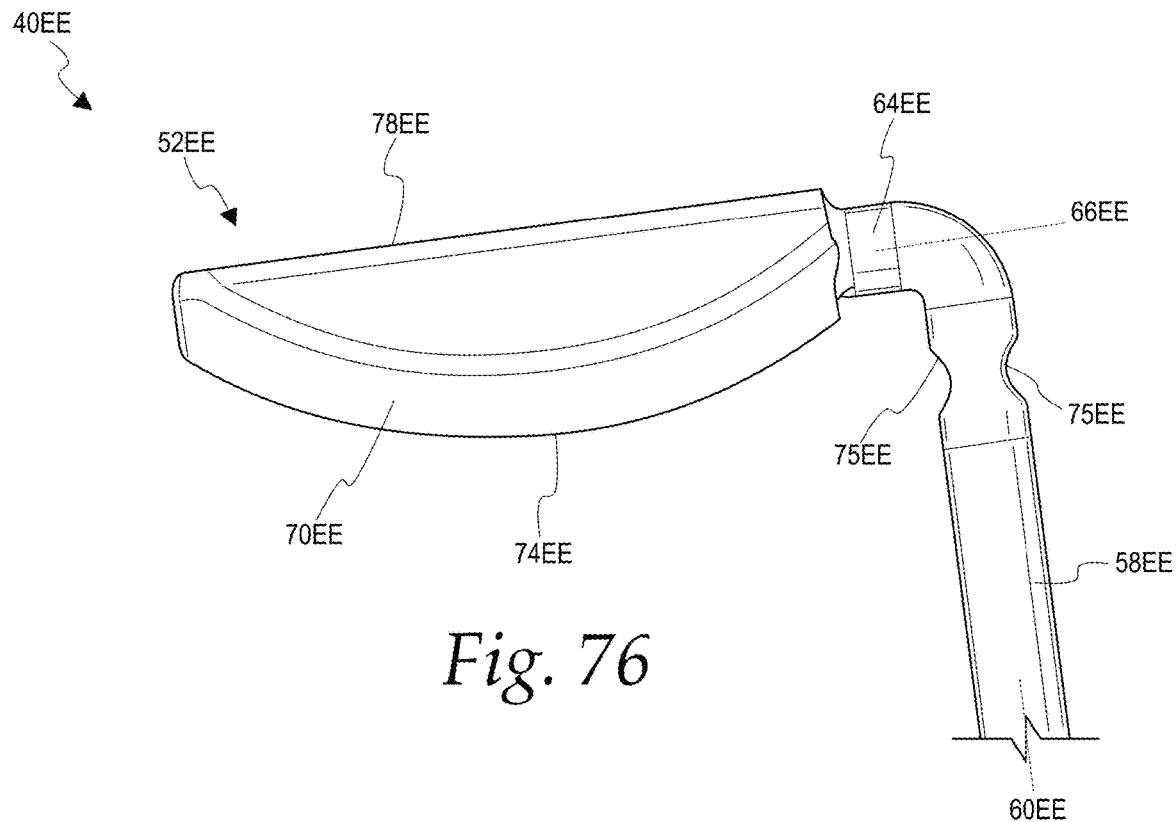
FIG. 76 is a greatly enlarged, fragmentary, isometric view from above of the instrument of FIG. 74.

Referring now to FIGS. 74-76, another embodiment of a cannulated instrument of the present invention is illustrated and designated as 40EE. While only the left-angled instrument 40EE is illustrated, it will be understood that a mirror opposite, right-angled instrument 40EE, and non-angled or straight instrument 40EE, is contemplated. The numbered features of the instrument 40EE are designated generally with the suffix letter "EE" and are analogous to features of the aforementioned illustrated embodiment of the instrument 40A that shares the same number (without the suffix letter "EE"). The instrument 40EE operates in a similar manner as described in detail above with respect to the instrument 40A.

The embodiment of the instrument 40EE differs from the above-discussed instrument 40A in that the instrument 40EE is configured with an internal flow passage 76EE that terminates in a pair of oppositely-facing irrigation ports 75EE located in the intermediate portion 58EE of the instrument tip 52EE to direct a flow of an irrigation fluid generally parallel to the central axis 66EE (left and right) defined by the terminal portion 58EE.

Figure 77:
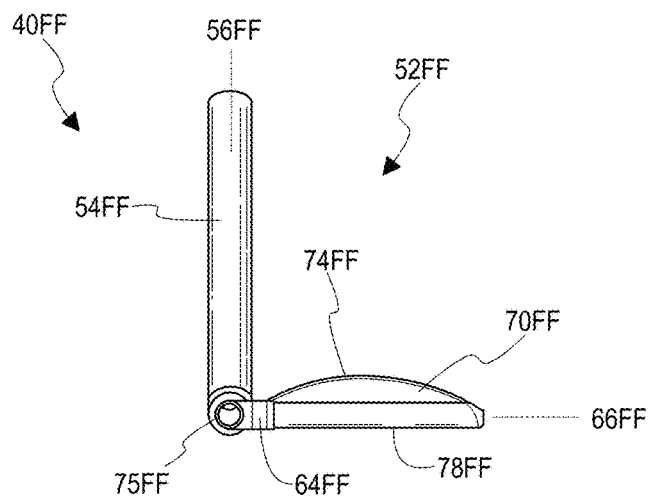
FIG. 77 is a greatly enlarged, fragmentary, rear elevation view of a thirty-third embodiment of a surgical instrument according to the present invention, wherein the instrument is configured as a left-angled instrument and only part of the tip portion is visible.
Figure 78:
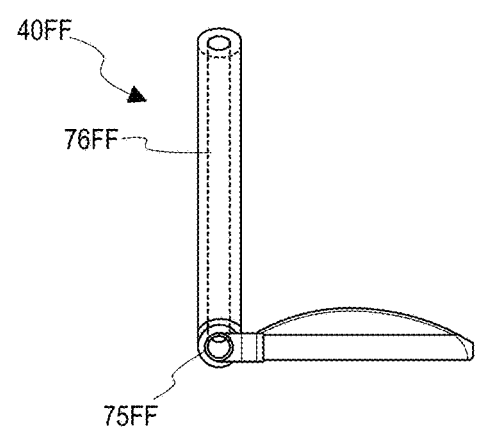
FIG. 78 is a greatly enlarged, fragmentary, rear elevation view of the instrument of FIG. 77.

Referring now to FIGS. 77 and 78, another embodiment of a cannulated instrument of the present invention is illustrated and designated as 40FF. While only the left-angled instrument 40FF is illustrated, it will be understood that a mirror opposite, right-angled instrument 40FF, and non-angled or straight instrument 40FF, is contemplated. The numbered features of the instrument 40FF are designated generally with the suffix letter "FF" and are analogous to features of the aforementioned illustrated embodiment of the instrument 40A that shares the same number (without the suffix letter "FF"). The instrument 40FF operates in a similar manner as described in detail above with respect to the instrument 40A.

The embodiment of the instrument 40FF differs from the above-discussed instrument 40A in that the instrument 40FF is configured with an internal flow passage 76FF that terminates in single irrigation port 75FF located at the junction of the intermediate portion 58FF and the terminal portion 64FF of the instrument tip 52FF to direct a flow of an irrigation fluid generally parallel to the central axis (out of the view plane in FIGS. 77 and 78 defined by the intermediate portion 58FF).

Figure 80:
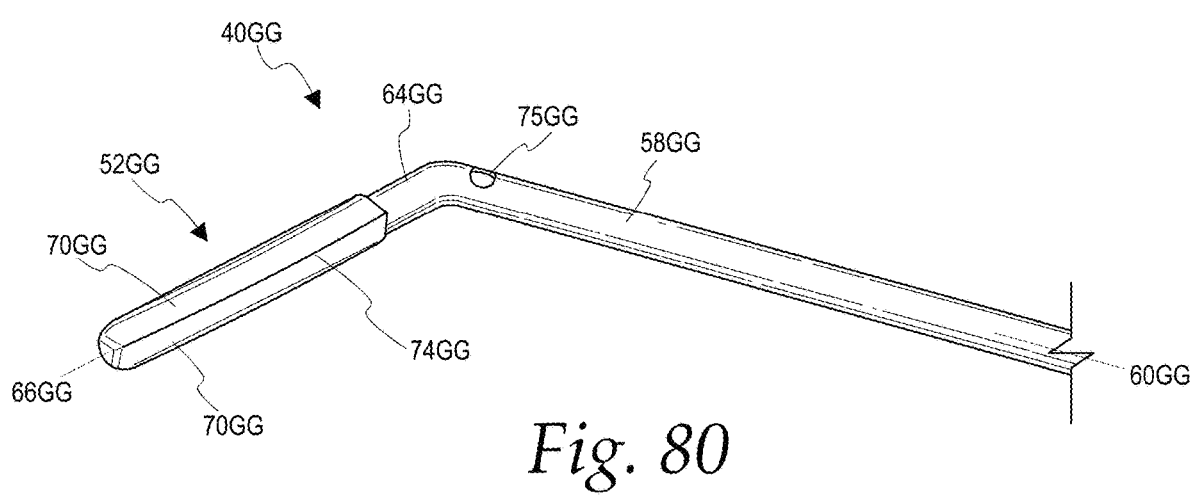
FIG. 80 is a greatly enlarged, fragmentary, isometric view from above of a thirty-fourth embodiment of a surgical instrument according to the present invention, wherein the instrument is configured as a left-angled instrument and only part of the tip portion is visible.

Referring now to FIGS. 80 and 81, another embodiment of a cannulated instrument of the present invention is illustrated and designated as 40GG. While only the left-angled instrument 40GG is illustrated, it will be understood that a mirror opposite, right-angled instrument 40GG, and non-angled or straight instrument 40GG, is contemplated. The numbered features of the instrument 40GG are designated generally with the suffix letter "GG" and are analogous to features of the aforementioned illustrated embodiment of the instrument 40A that shares the same number (without the suffix letter "GG"). The instrument 40GG operates in a similar manner as described in detail above with respect to the instrument 40A.

The embodiment of the instrument 40GG differs from the above-discussed instrument 40A in that the instrument 40GG is configured with an internal flow passage that terminates in a pair of opposing irrigation ports 75GG located just proximal to the junction of the intermediate portion 58GG and the terminal portion 64GG of the instrument tip 52GG to direct a flow of an irrigation fluid generally perpendicular or normal to the central axes 66GG and 60GG (out of the plane containing said axes).

Figure 83:
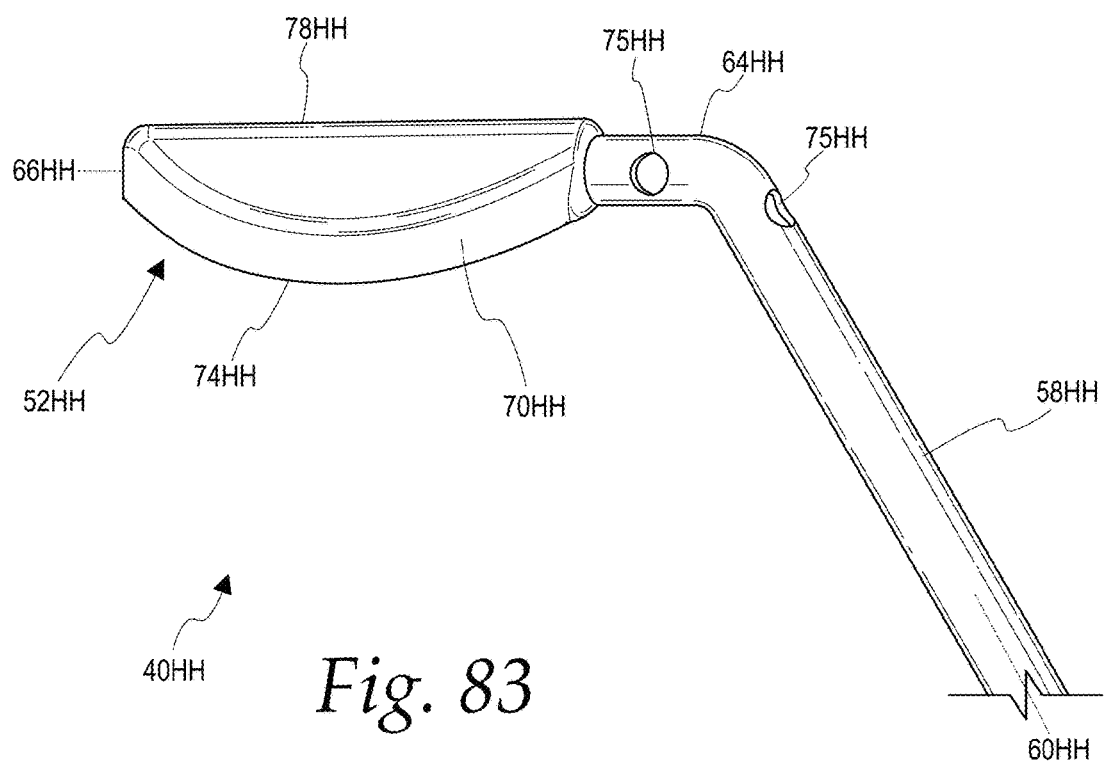
FIG. 83 is a fragmentary, isometric view from above of the portion of the instrument shown in FIG. 82.

Referring now to FIGS. 82 and 83, another embodiment of a cannulated instrument of the present invention is illustrated and designated as 40HH. While only the left-angled instrument 40HH is illustrated, it will be understood that a mirror opposite, right-angled instrument 40HH, and non-angled or straight instrument 40HH, is contemplated. The numbered features of the instrument 40HH are designated generally with the suffix letter "HH" and are analogous to features of the aforementioned illustrated embodiment of the instrument 40A that shares the same number (without the suffix letter "HH"). The instrument 40HH operates in a similar manner as described in detail above with respect to the instrument 40A.

The embodiment of the instrument 40HH differs from the above-discussed instrument 40A in that the instrument 40HH is configured with an internal flow passage that terminates in a pair of opposing irrigation ports 75HH located in the terminal portion 64HH of the instrument tip 52HH to direct a flow of an irrigation fluid generally perpendicular or normal to the central axes 66HH and 60HH (out of the plane containing said axes) and a third irrigation port 75HH located in the intermediate portion 58HH just proximal to the junction of the intermediate portion 58HH and the terminal portion 64HH to direct a flow of an irrigation fluid generally laterally and generally perpendicular or normal to the central axis 60HH and within the plain containing axes 66HH and 60HH.

Figure 84:
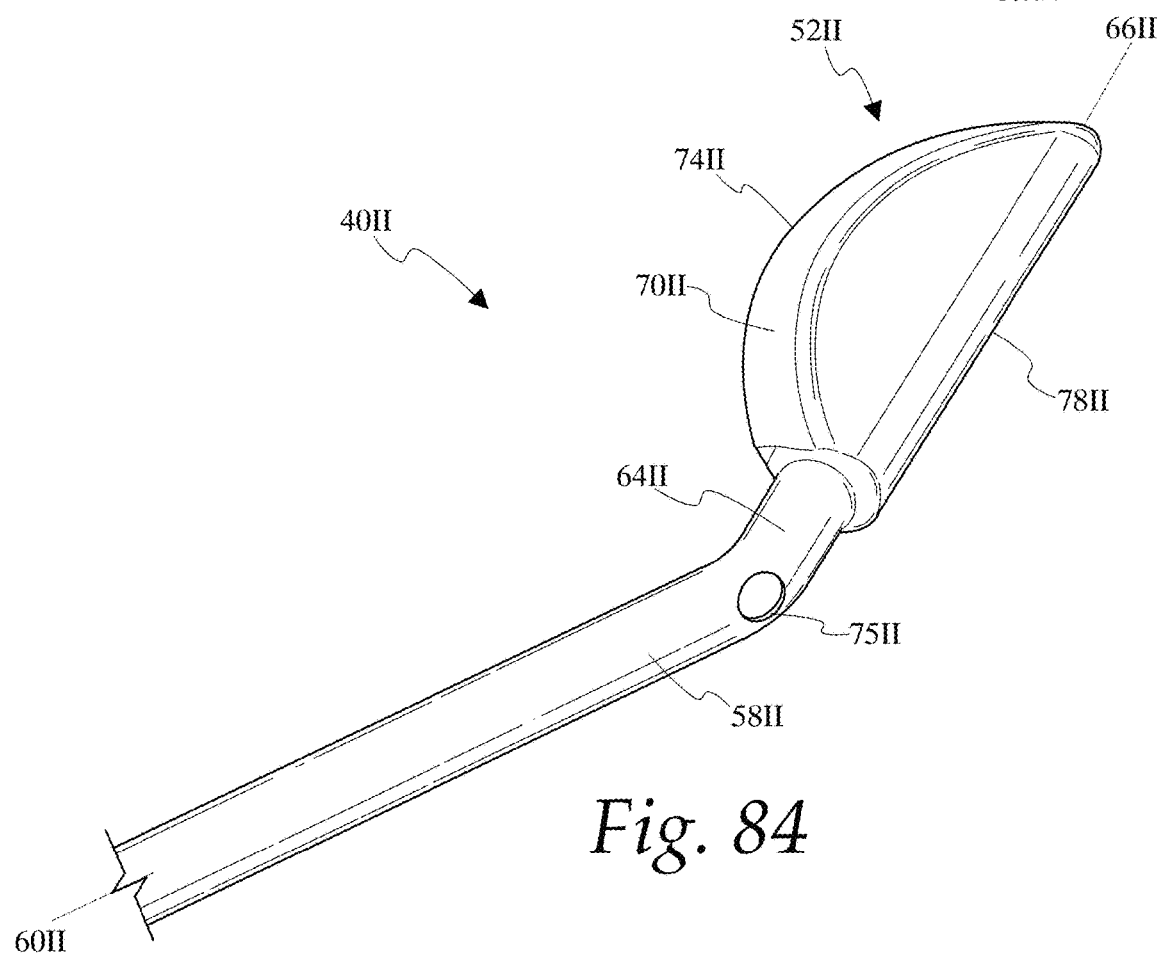
FIG. 84 is a greatly enlarged, fragmentary, isometric view from above of a thirty-sixth embodiment of a surgical instrument according to the present invention, wherein the instrument is configured as a left-angled instrument and only part of the tip portion is visible.
Figure 85:
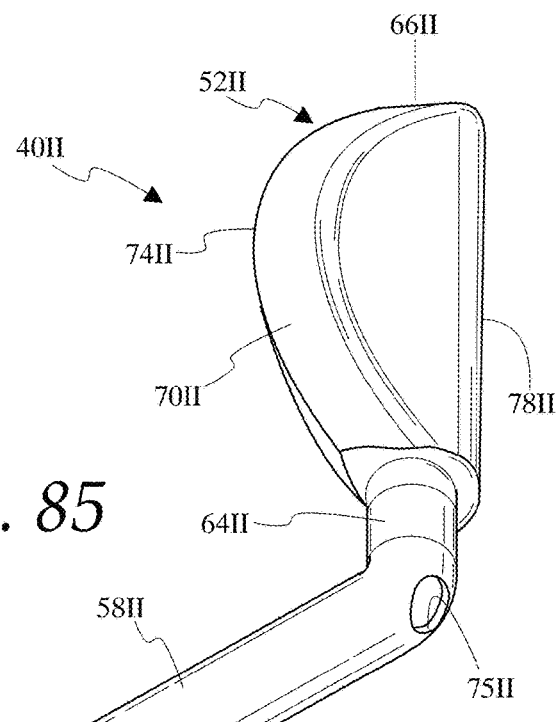
FIG. 85 is a fragmentary, isometric view from above of the portion of the instrument shown in FIG. 84.
Figure 86:
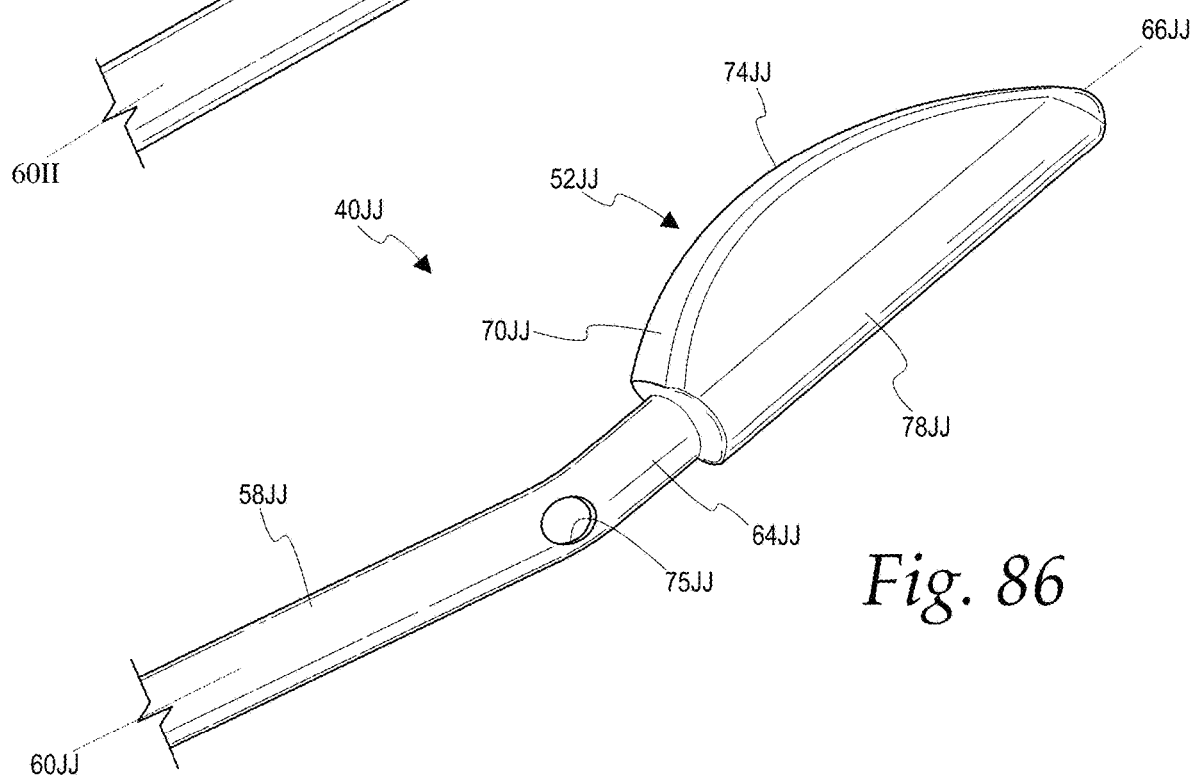
FIG. 86 is a greatly enlarged, fragmentary, isometric view from above of a thirty-seventh embodiment of a surgical instrument according to the present invention, wherein the instrument is configured as a left-angled instrument and only part of the tip portion is visible.

Referring now to FIGS. 84 and 85, two additional embodiments of a cannulated instrument of the present invention are illustrated and designated as 40II and 40JJ, respectively. While only the left-angled instruments 40II and 40JJ are illustrated, it will be understood that a mirror opposite, right-angled instruments, and non-angled or straight instruments, are contemplated herein. The numbered features of the instruments 40II and 40JJ are designated generally with the suffix letter "II" or "JJ" and are analogous to features of the aforementioned illustrated embodiment of the instrument 40A that shares the same number (without the suffix letters "II" or "JJ"). The instruments 40II and 40JJ operate in a similar manner as described in detail above with respect to the instrument 40A.

The embodiments of the instrument 40II and 40JJ differ from the above-discussed instrument 40A in that the instruments 40II and 40JJ are configured with an internal flow passage that terminates in a single irrigation port 75II and 75JJ located in junction between the intermediate portion 58II and 58JJ and the terminal portion 64II and 64JJ to direct a flow of an irrigation fluid generally in a transverse direction relative to each of the central axes 66II and 66JJ and 60II and 60JJ. The irrigation port 75II is circular in shape while the irrigation port 75JJ is oval in shape.

Various modifications and alterations to this invention will become apparent to those skilled in the art without departing from the scope and spirit of this invention. Illustrative embodiments and examples are provided as examples only and are not intended to limit the broadest scope of the present invention.

The invention claimed is:

1. A method of using a goniotomy surgical instrument to treat the trabecular meshwork of the eye, the method comprising the steps of:
   obtaining a goniotomy surgical instrument, said instrument having
      a hand grip with an elongated configuration, a proximal end and a distal end, and
      a tip connected to said distal end of said hand grip, said tip having a cutting means for creating a trabecular leaflet at Schwalbe's line in an eye;
   gripping said hand grip to bring said cutting means into contact with the trabecular meshwork of an eye directly below Schwalbe's line; and
   cutting a leaflet of the trabecular meshwork with said cutting means.

2. A goniotomy surgical instrument, comprising:
   a hand grip having an elongated configuration, having proximal end and a distal end; and
   a tip connected to said distal end of said hand grip, said tip having a cutting means for creating a trabecular leaflet at Schwalbe's line in an eye.

3. The goniotomy surgical instrument in accordance with claim 2, wherein said cutting means is a pair of sloping, arcuate cutting surfaces that join to define an arcuate cutting edge.

4. The goniotomy surgical instrument in accordance with claim 3, wherein said arcuate cutting edge defines an edge axis that is angled between about 30 degrees and about 60 degrees relative to a plane containing said terminal portion axis and said intermediate portion axis.

5. The goniotomy surgical instrument in accordance with claim 4, wherein said edge axis is angled about 40 degrees relative to said plane containing said terminal portion axis and said intermediate portion axis.

6. The goniotomy surgical instrument in accordance with claim 2, wherein said cutting means faces said hand grip.

7. The goniotomy surgical instrument in accordance with claim 2, wherein said cutting means has a beveled configuration that defines a semi-circular, arcuate cutting edge.

8. The goniotomy surgical instrument in accordance with claim 2, wherein said cutting means is an elliptical, planar, sloping surface that terminates in a distal, arcuate cutting edge.

9. The goniotomy surgical instrument in accordance with claim 2, wherein said cutting means is a conical surface that terminates in a distal, pointed cutting edge.

10. The goniotomy surgical instrument in accordance with claim 2, wherein said cutting means has a tapering configuration defining faces that terminate in a blunted, rounded distal edge.

11. The goniotomy surgical instrument in accordance with claim 2, wherein said cutting means has a tapering configuration defining a concave face that terminates in a spatulated distal edge.

* * * * *